US012703682B2

(12) United States Patent
Marubayashi et al.

(10) Patent No.: US 12,703,682 B2
(45) Date of Patent: *Aug. 11, 2026

(54) CRYSTALLINE FORM OF SOFPIRONIUM BROMIDE AND PREPARATION METHOD THEREOF

(71) Applicants: Kaken Pharmaceutical Co., Ltd., Tokyo (JP); Botanix SB, Inc., King of Prussia, PA (US)

(72) Inventors: Kazuyoshi Marubayashi, Shizuoka (JP); Masahito Watanabe, Shizuoka (JP); Herbert R. Brinkman, Fort Collins, CO (US)

(73) Assignees: Kaken Pharmaceutical Co., Ltd., Tokyo (JP); Brickell Biotech, Inc., Boulder, CO (US)

( * ) Notice: Subject to any disclaimer, the term of this patent is extended or adjusted under 35 U.S.C. 154(b) by 856 days.

This patent is subject to a terminal disclaimer.

(21) Appl. No.: 17/611,158

(22) PCT Filed: May 22, 2020

(86) PCT No.: PCT/JP2020/020210

§ 371 (c)(1),
(2) Date: Nov. 14, 2021

(87) PCT Pub. No.: WO2020/235665

PCT Pub. Date: Nov. 26, 2020

(65) Prior Publication Data

US 2022/0298108 A1 Sep. 22, 2022

Related U.S. Application Data

(60) Provisional application No. 62/851,880, filed on May 23, 2019.

(51) Int. Cl.
*C07D 207/12* (2006.01)
*A61K 9/00* (2006.01)
*C07C 59/147* (2006.01)

(52) U.S. Cl.
CPC .......... *C07D 207/12* (2013.01); *A61K 9/0014* (2013.01); *C07C 59/147* (2013.01); *C07B 2200/13* (2013.01)

(58) Field of Classification Search
None
See application file for complete search history.

(56) References Cited

FOREIGN PATENT DOCUMENTS

WO WO 2018/02869 * 2/2018 .......... C07D 207/12

* cited by examiner

*Primary Examiner* — Craig D Ricci
(74) *Attorney, Agent, or Firm* — Ted Whitlock Registered Patent Attorney PA

(57) ABSTRACT

A cocrystal containing the 1'R-diastereomer and the 1'S-diastereomer of sofpironium bromide at a ratio of 1:3 (Form CO), a crystal mixture (for example, Form B) containing Form CO and a crystalline form of the 1'R-diastereomer (Form MN), and a method for preparing sofpironium bromide, which is suitable for manufacture of the crystal mixture are provided. Form CO and a crystalline form of sofpironium bromide containing Form CO (for example, Form B) have superior stability without hygroscopic property, and accordingly they can be preferably used as a raw material of medicaments.

7 Claims, 35 Drawing Sheets

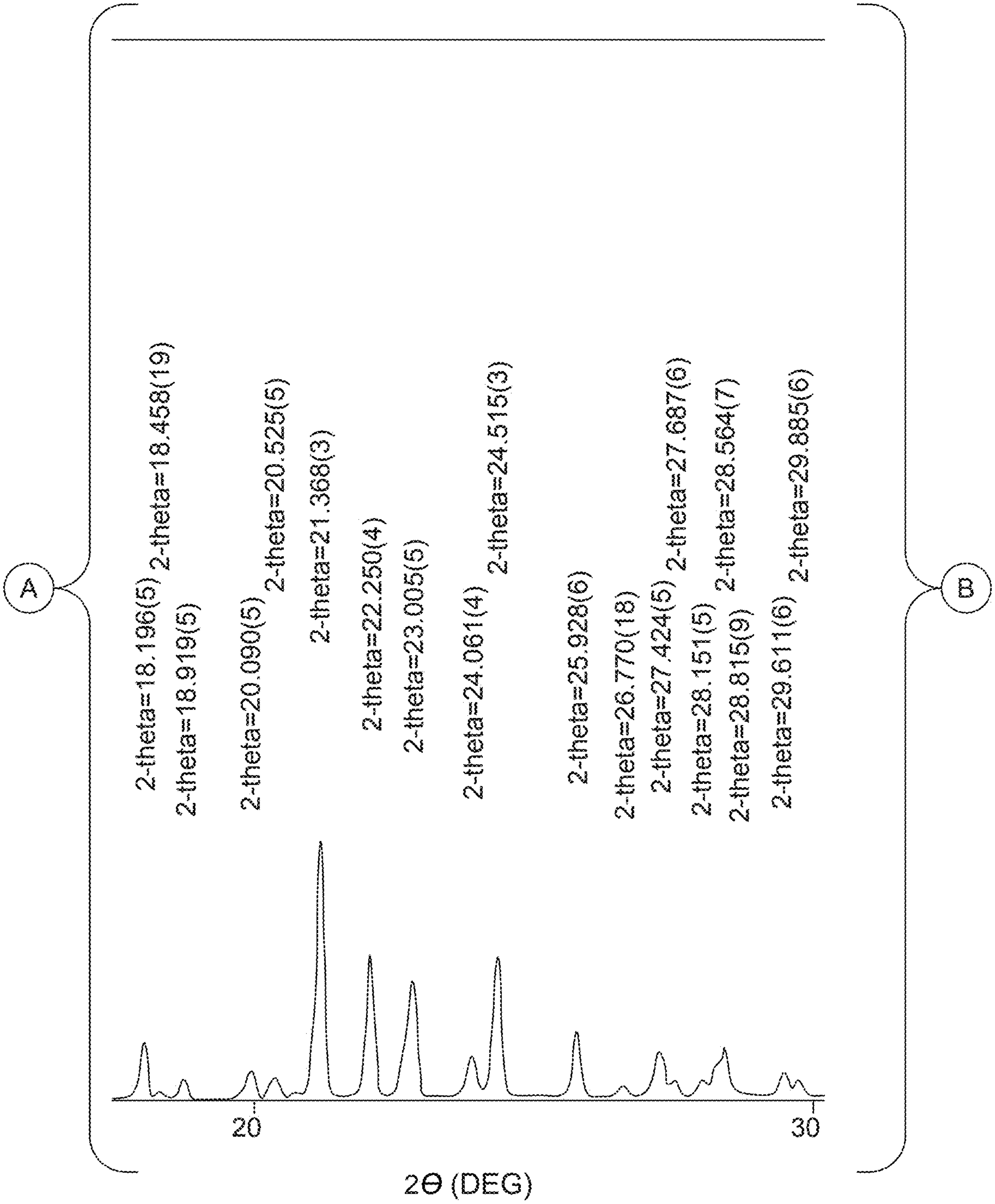
FIG. 1 (CONTINUATION)

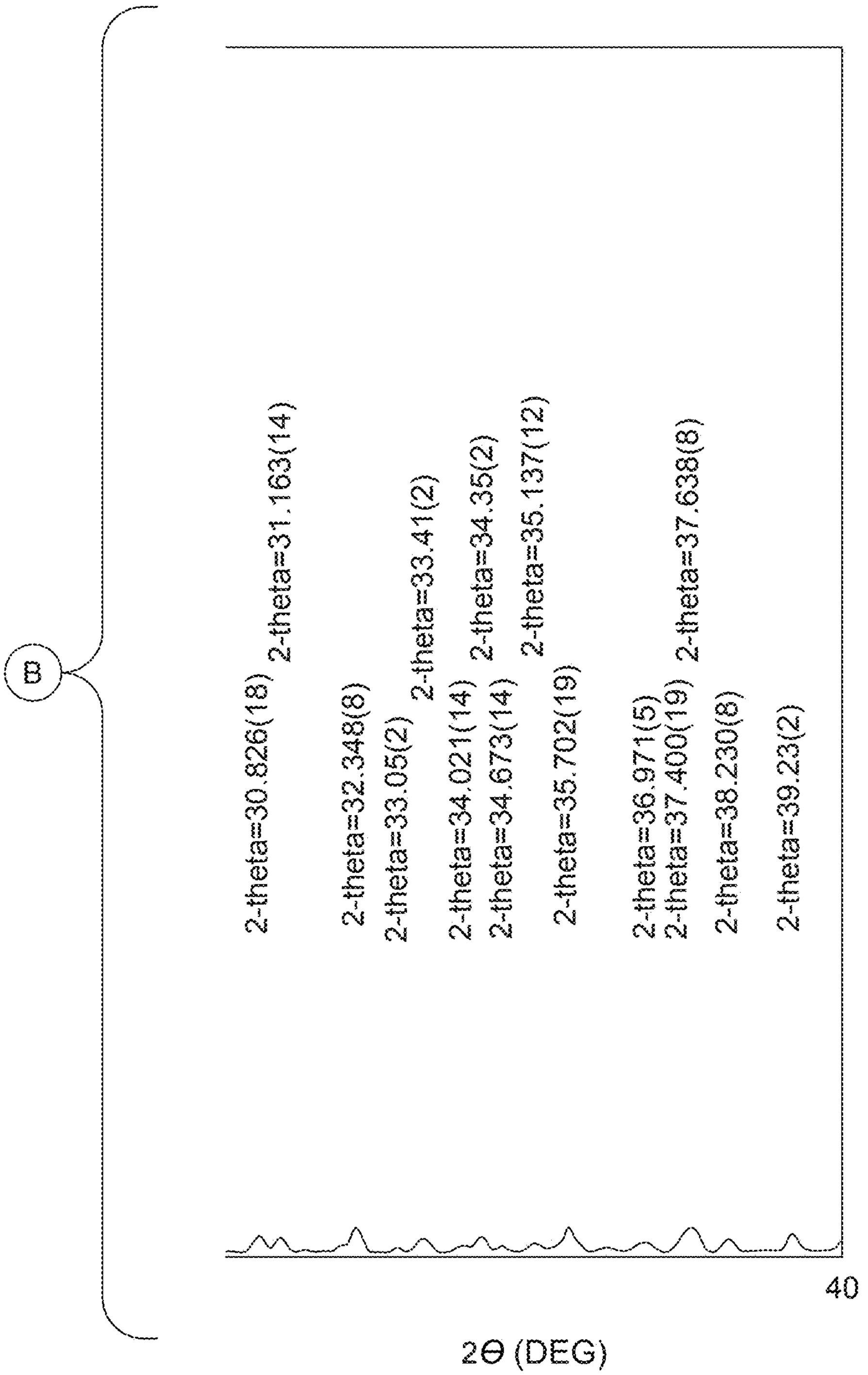
FIG. 1 (CONTINUATION)

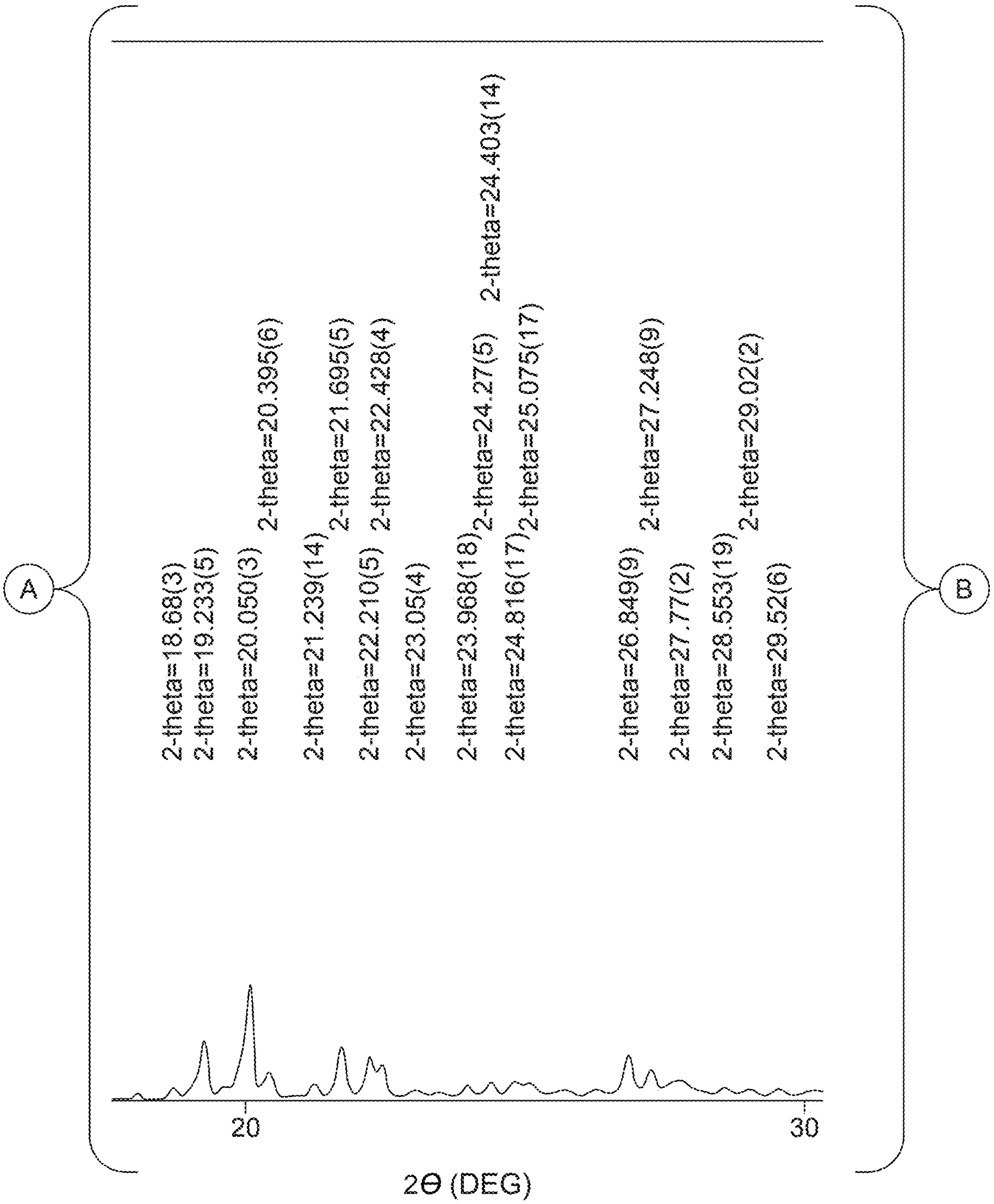
FIG. 2 (CONTINUATION)

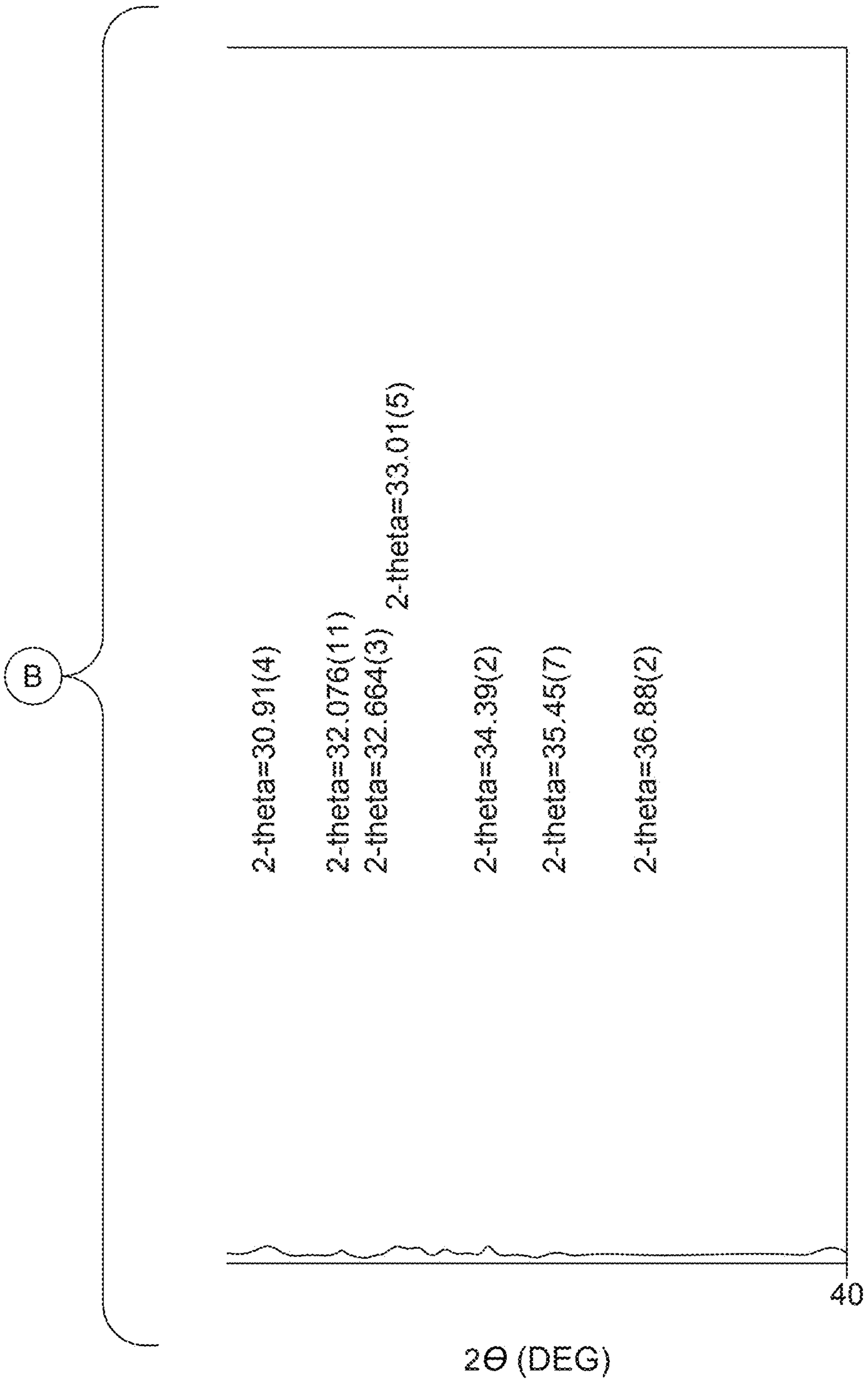
FIG. 2 (CONTINUATION)

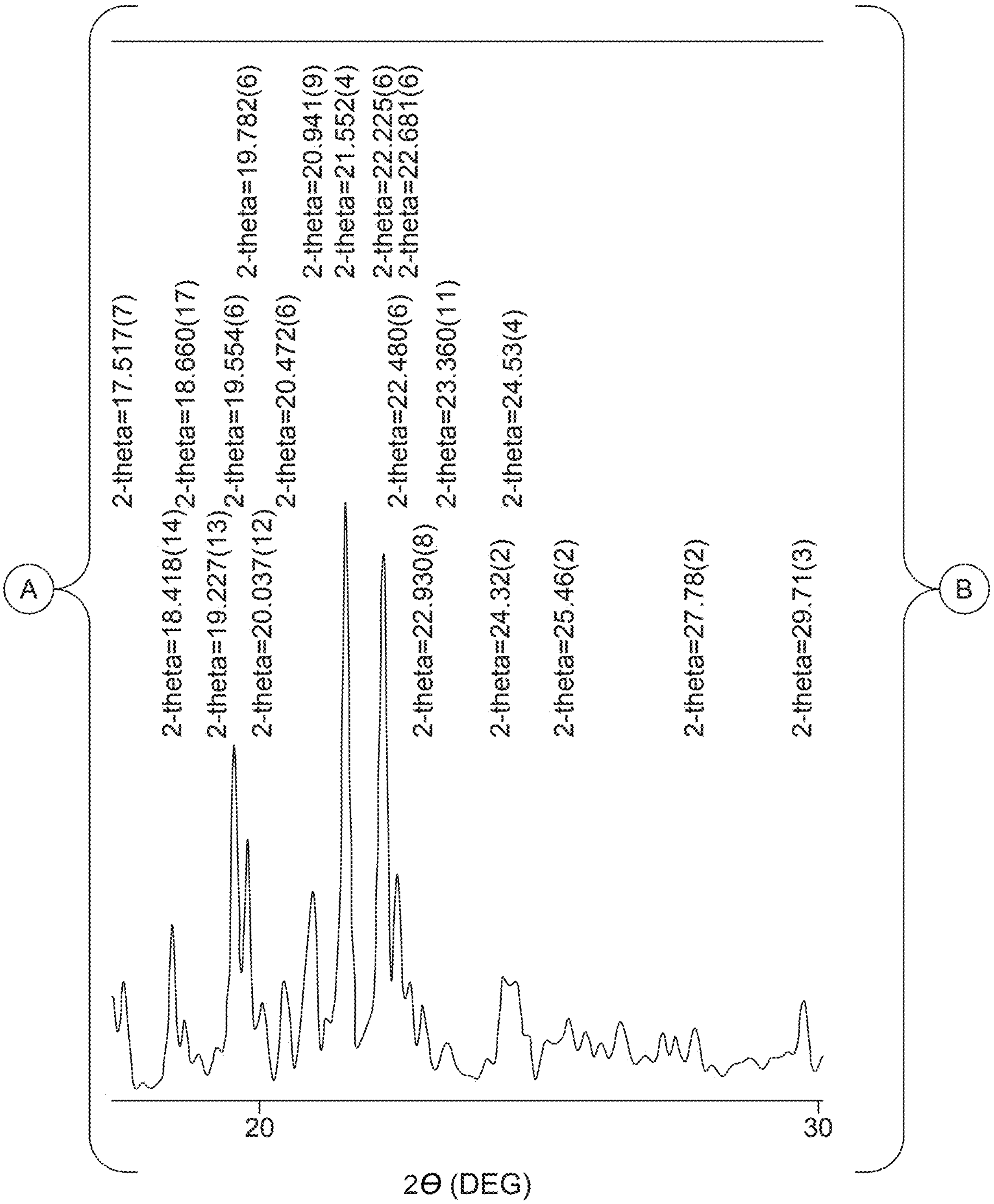
FIG. 3 (CONTINUATION)

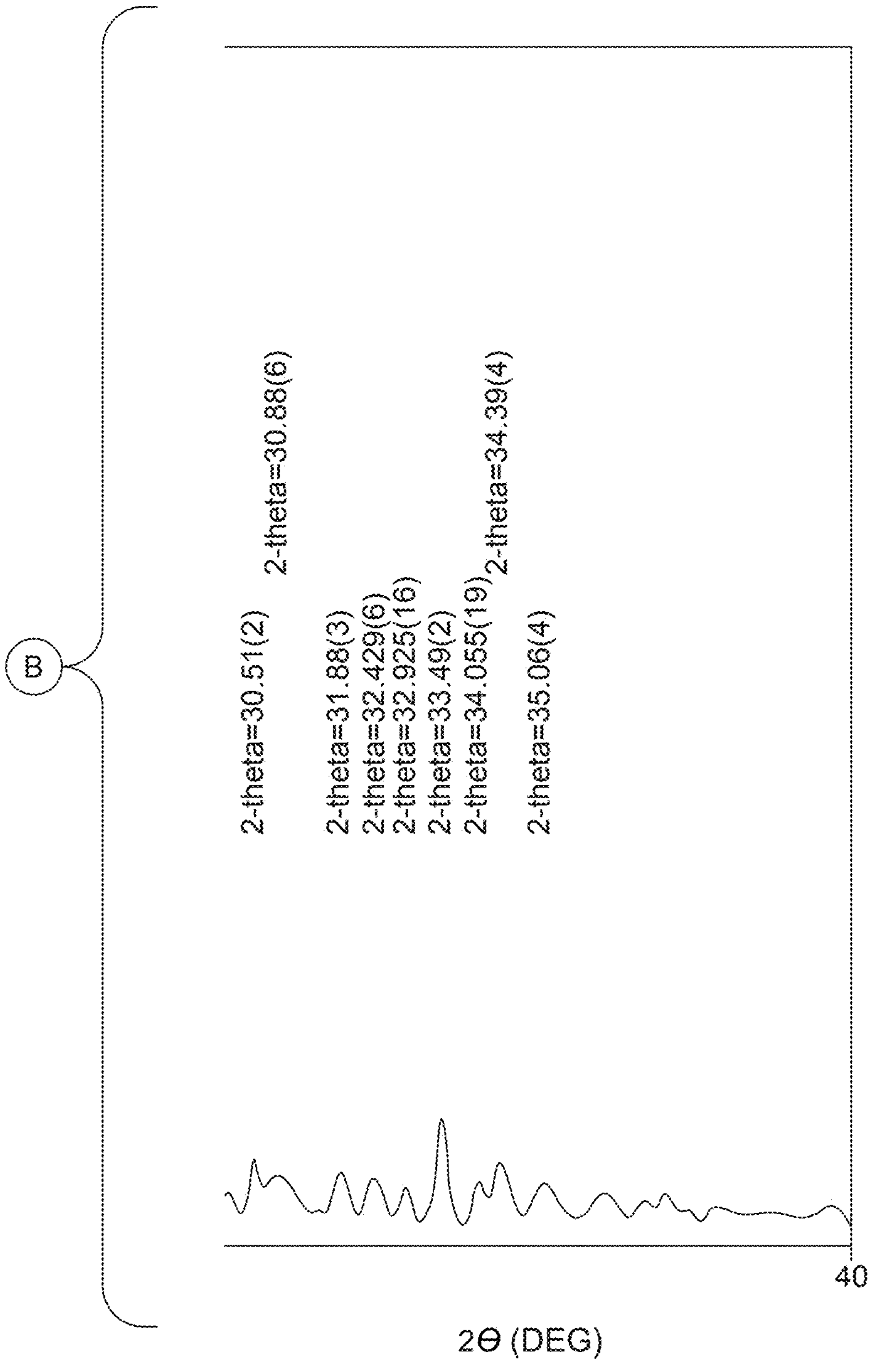
FIG. 3 (CONTINUATION)

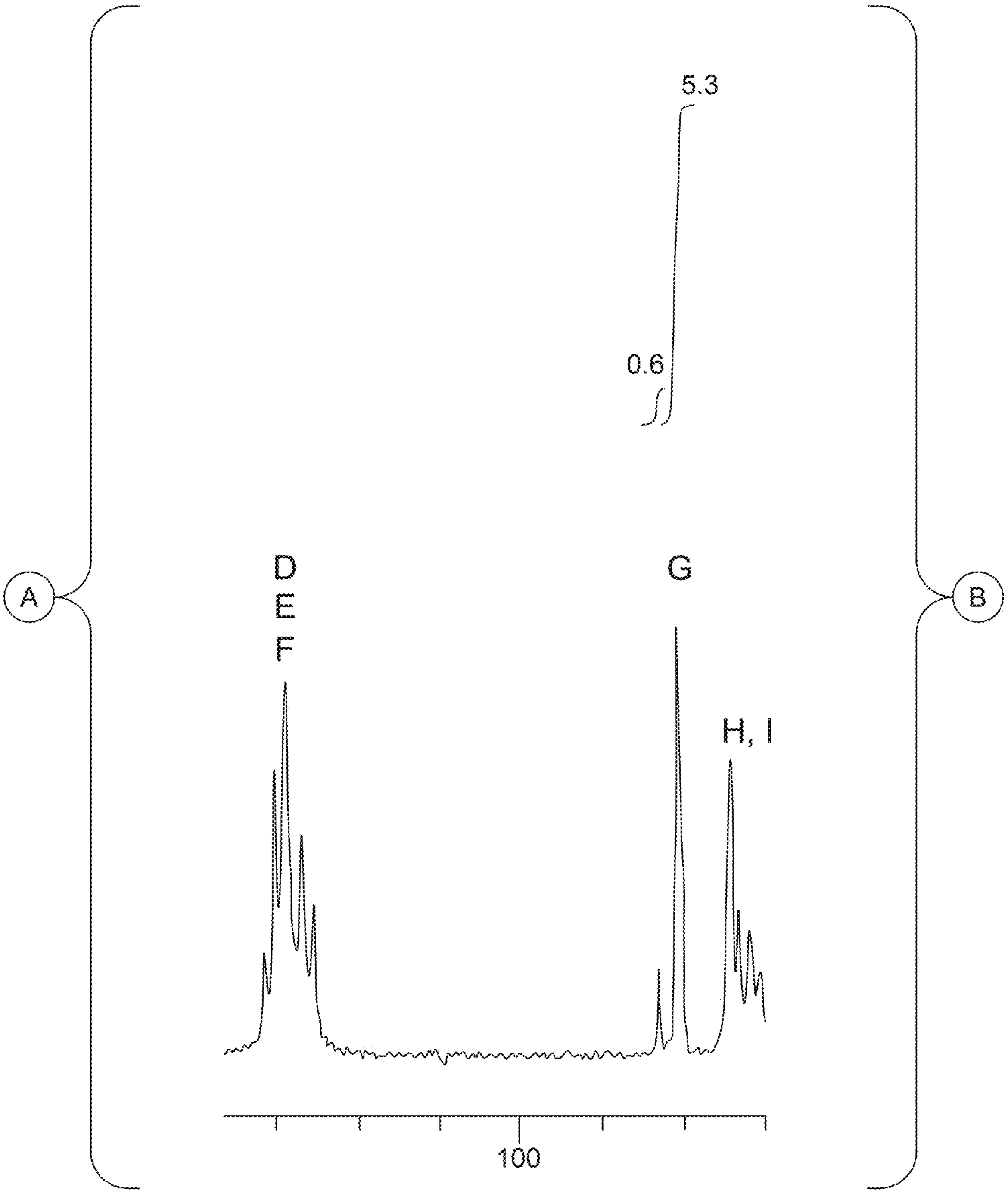
FIG. 4 (CONTINUATION)

B
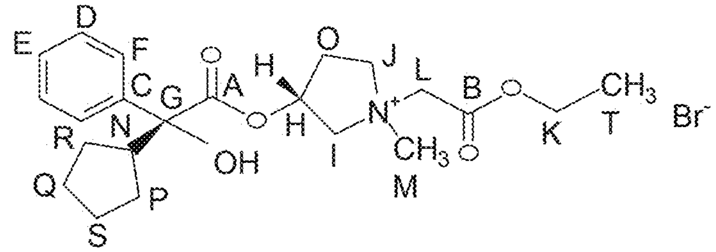
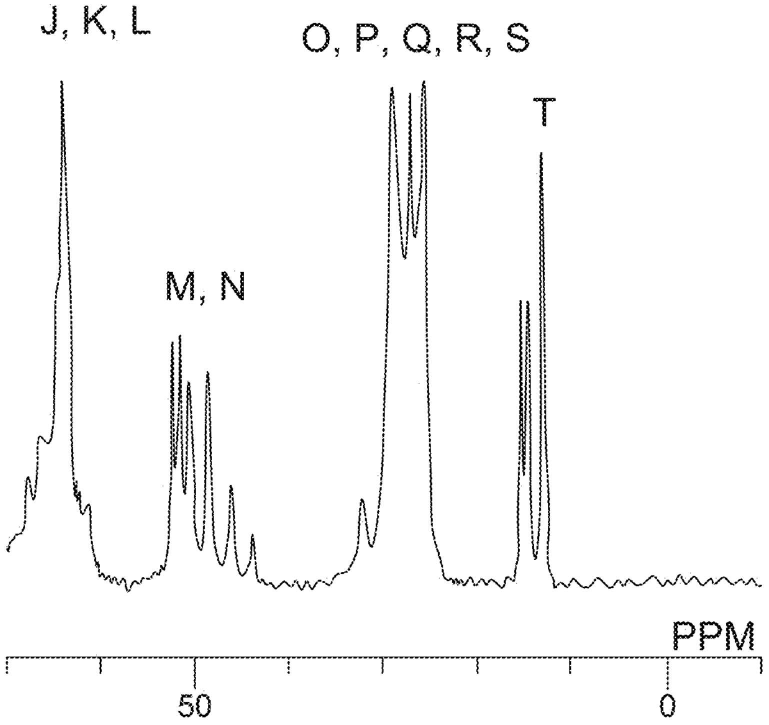
FIG. 4 (CONTINUATION)

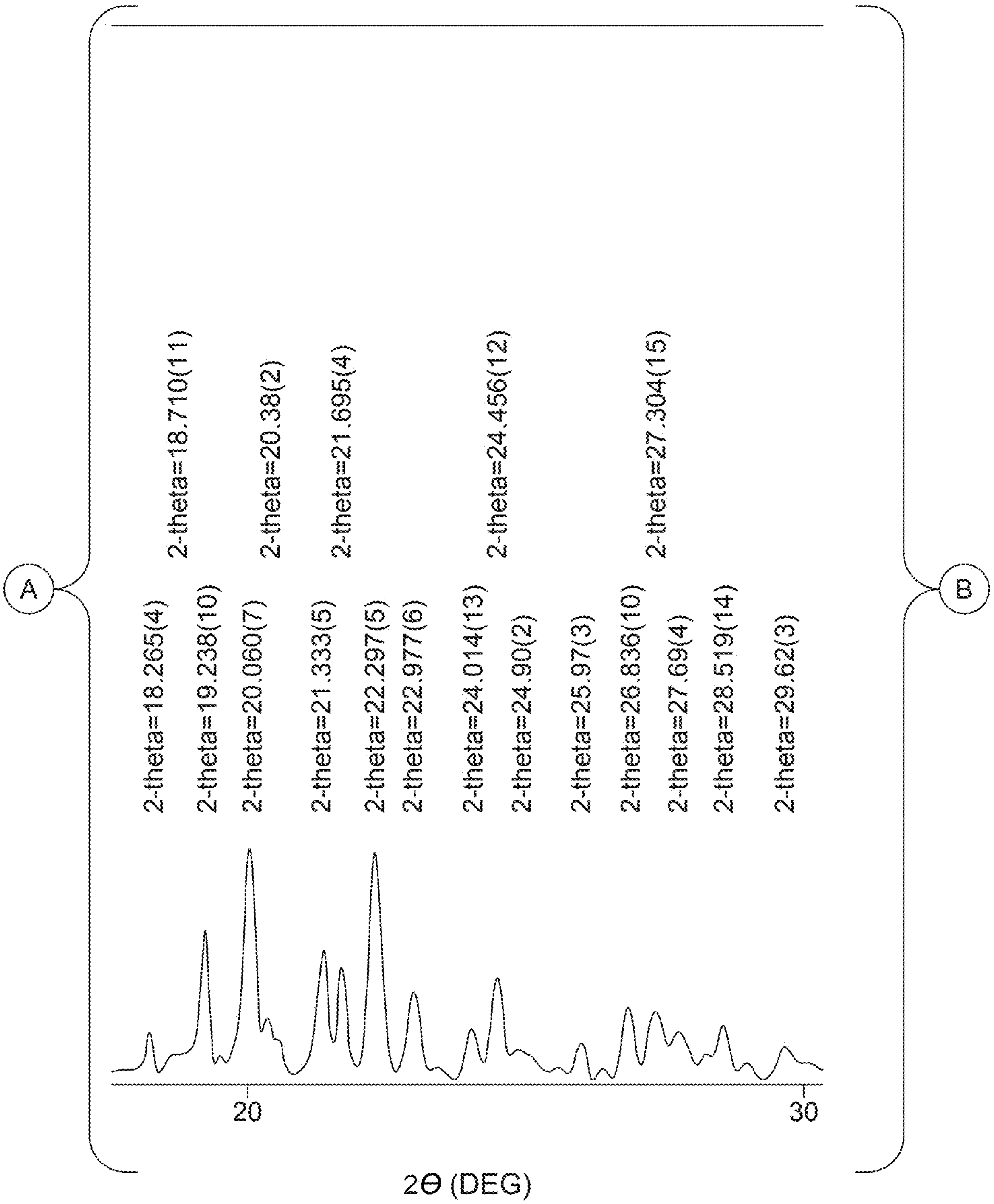
FIG. 9 (CONTINUATION)

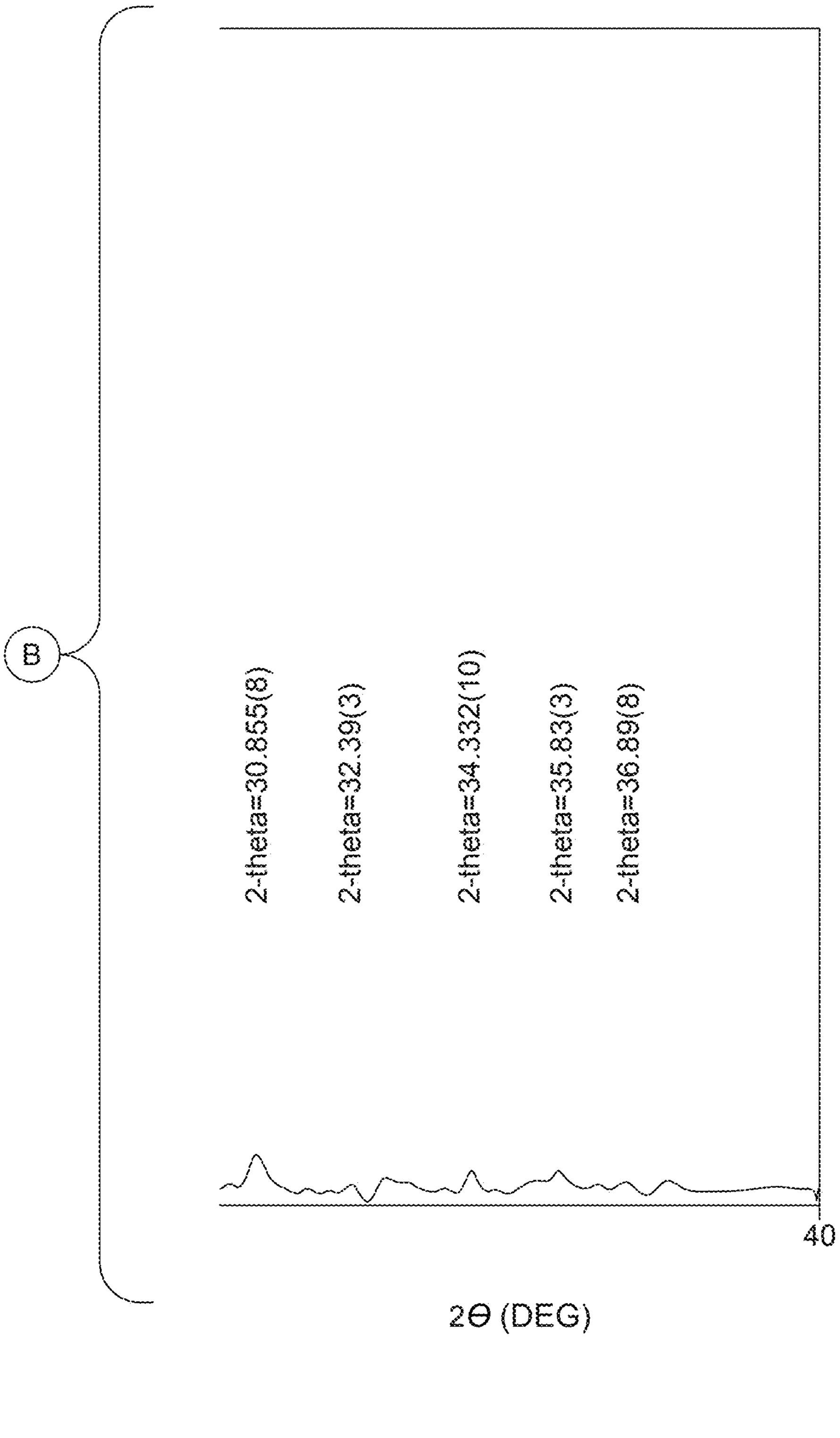
FIG. 9 (CONTINUATION)

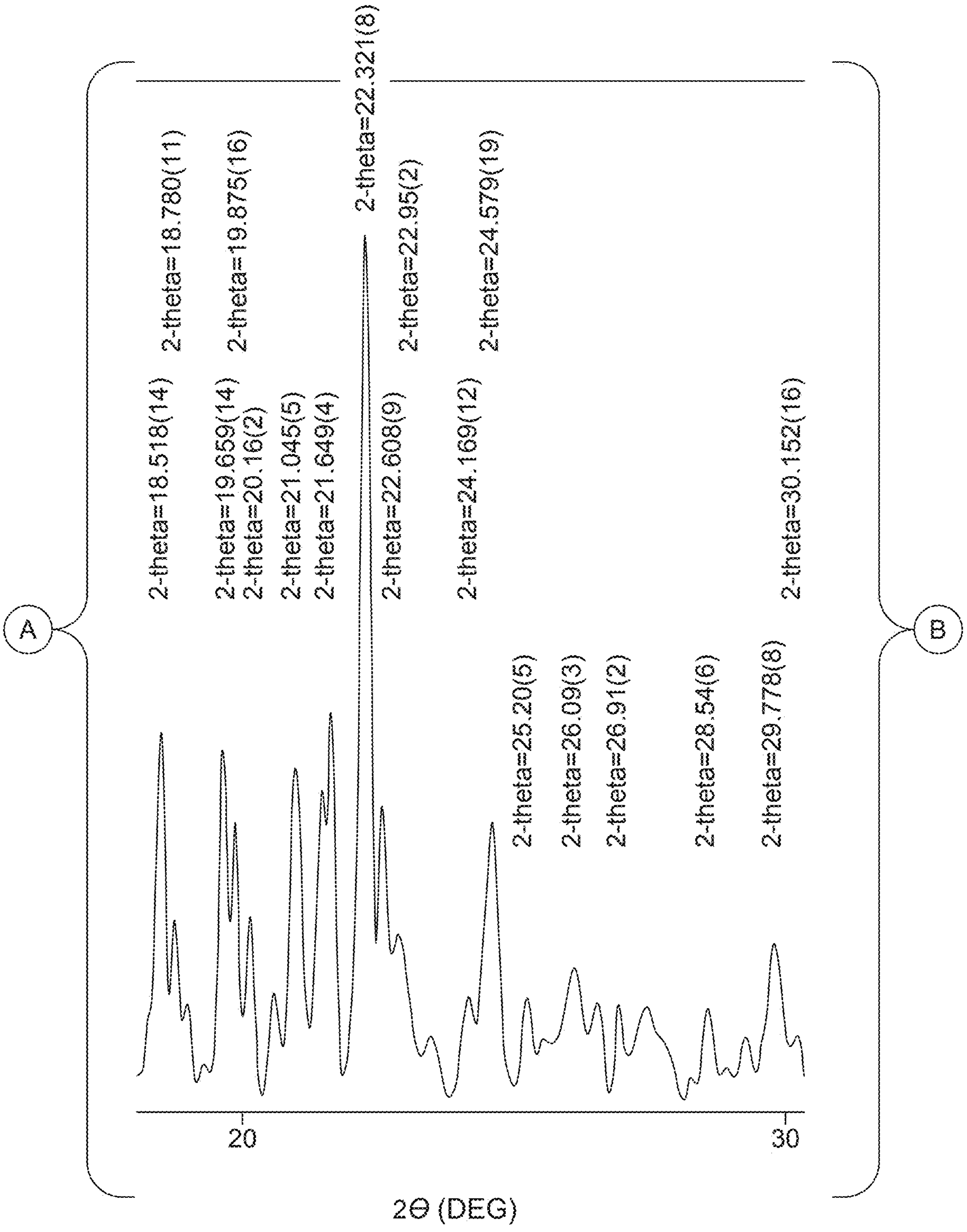
FIG. 10 (CONTINUATION)

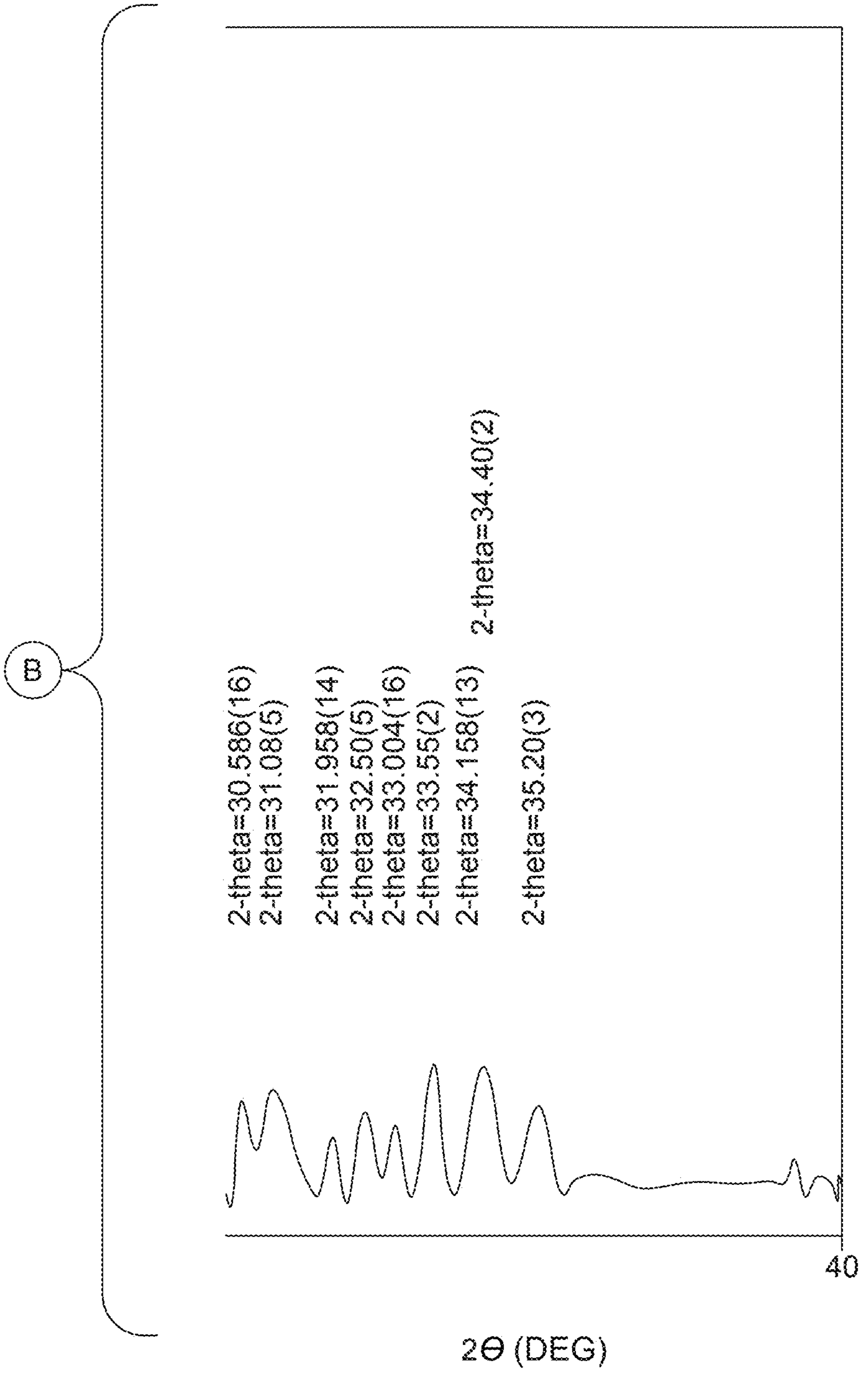
FIG. 10 (CONTINUATION)

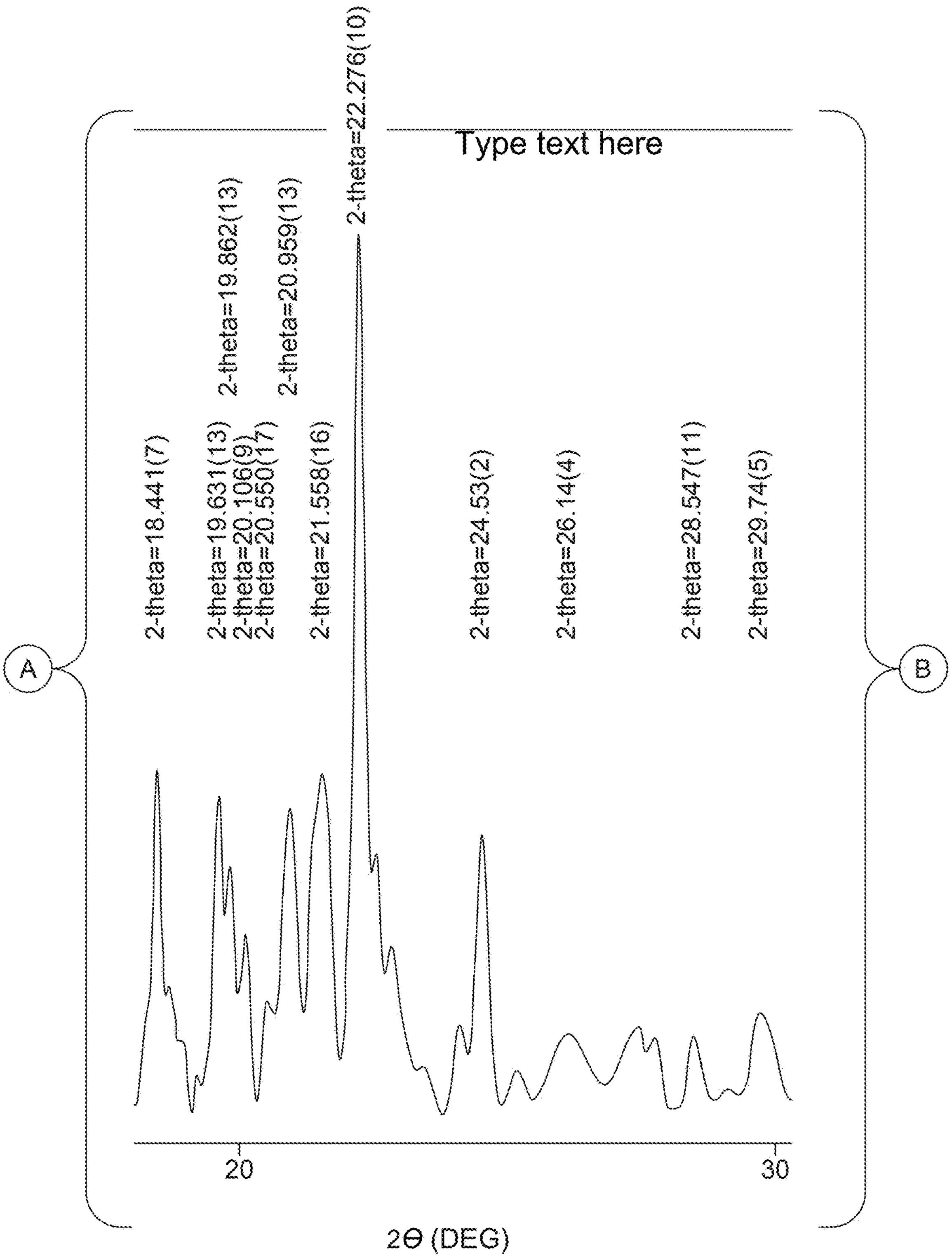
FIG. 11 (CONTINUATION)

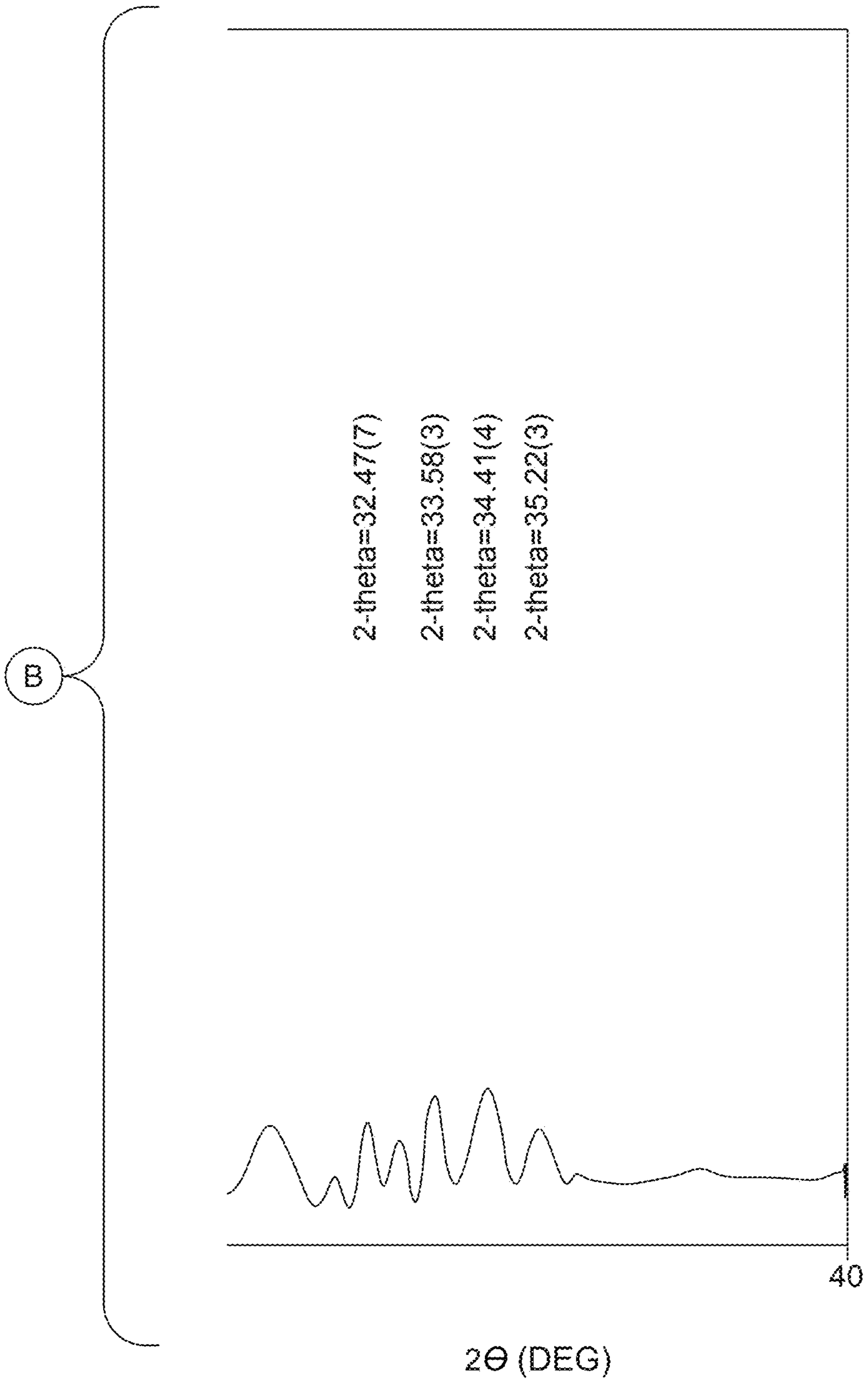
FIG. 11 (CONTINUATION)

CRYSTALLINE FORM OF SOFPIRONIUM BROMIDE AND PREPARATION METHOD THEREOF

TECHNICAL FIELD

The present invention relates to a crystalline form of sofpironium bromide, high-purity sofpironium bromide, and preparation methods thereof.

BACKGROUND ART

It is preferred that drug substances of medicaments can be industrially obtained as a high-purity and physicochemically stable form. In addition, from a viewpoint of handling or storage, it is particularly preferred to be obtained in a physicochemically stable crystalline form.

Acetylcholine is known as a major neurotransmitter of living bodies, and has various actions, and the perspiration activity based on activation of sweat glands is one of such actions. Anticholinergic agents are useful as therapeutic agents for hyperhidrosis because of inhibition of the actions of acetylcholine. BBI-4000 (Sofpironium bromide) is known as an anticholinergic agent useful for therapeutic treatment of hyperhidrosis (Patent document 1).

Sofpironium bromide is a quaternary ammonium salt compound represented by the following formula (I) (BBI-4000, (2R,3'R)-3'-(2-cyclopentyl-2-hydroxy-2-phenylacelyl)-1'-(ethoxycarbonylethyl)-1'-methylpyrrolidinium bromide).

[Chem. 1]

(I)

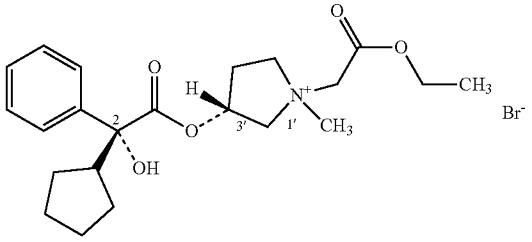

(2R, 3'R)

The stereochemistry at each of the 2- and 3'-positions of sofpironium bromide is identified as the R-configuration, but the stereochemistry of the quaternary nitrogen thereof at the 1'-position is not identified.

More specifically, sofpironium bromide is a mixture of (2R,3'R, 1'R)-3'-(2-cyclopentyl-2-hydroxy-2-phenylacetyl)-1'-(ethoxycarbonylmethyl)-1 '-methylpyrrolidinium bromide represented by the following formula (I-a):

[Chem. 2]

(I-a)

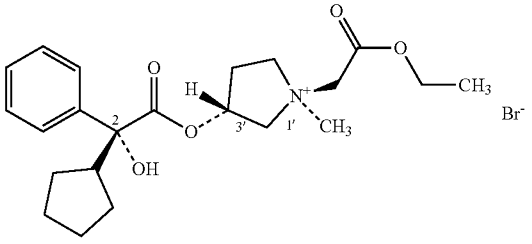

(2R, 3'R, 1'R)

(in the specification, the aforementioned 1'R-diastereomer is henceforth also referred to as "compound (I-a)"), and (2R,3'R, 1'S)-3'-(2-cyclopentyl-2-hydroxy-2-phenylacetyl)-1'-(ethoxycarbonylmethyl)-1'-methylpyrrolidinium bromide represented by the following formula (I-b):

[Chem. 3]

(I-b)

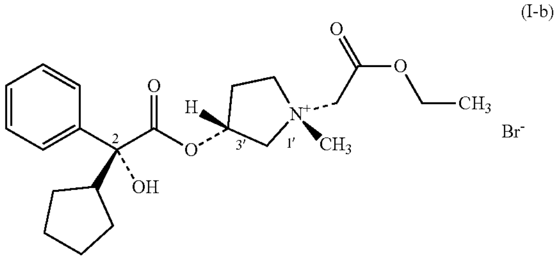

(2R, 3'R, 1'S)

(in the specification, the aforementioned 1'S-diastereomer is henceforth also referred to as "compound (I-b)").

Non-patent document 1 and Patent document 2 describe the methods of preparation of the compounds (I), and (I-a), and describe a method of performing N-alkylation reaction of an amine compound represented by the following formula (II):

[Chem. 4]

(II)

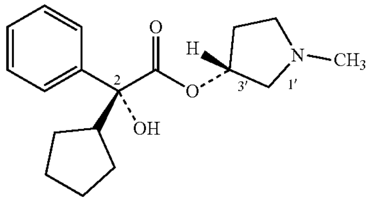

(2R, 3'R)

((2R,3'R)-3'-(2-cyclopenyl-2-hydroxy-2-phenylacetoxy)-1'-methylpyrrolidine (in the specification, the aforementioned amine compound is henceforth also referred to as "compound (II)" or "(2R,3'R)-CPMA-MP") with ethyl bromoacetate in acetonitrile to obtain a crude product of the compound (I), and then fractionating the compound (I-a) and the compound (I-b) by using column chromatography (chloroform/methanol).

The compound (I) obtained by this preparation method is a crude product. Although Non-patent document 1 does not mention a content ratio of the compound (I-a) and the compound (I-b) in the crude compound (I), it is described that the compound (I-a) was obtained in 19% yield (isolated yield), and the compound (I-b) was obtained in 28% yield (isolated yield) by column chromatography. However, in spite of the column chromatography purification, the purities of the compound (I-a) and the compound (I-b) obtained by this preparation method are low, in addition, properties and crystalline forms thereof are not described. Therefore, it is not considered that the compound (I), the compound (I-a) and the compound (I-b) obtained by this preparation have profiles suitable for a drug substance of medicaments.

Patent document 3 describes the method of performing N-alkylation reaction of the compound (II) with methyl bromoacetate in acetonitrile, and then adding a methylene chloride solution of the resulting crude compound (I) into diethyl ether to obtain precipitates. However, it is doubtful that the compound (I) can be prepared by reacting methyl bromoacetate with the compound (II). Even if the compound (I) can be prepared, Patent document 3 does not describe properties of the aforementioned precipitates of the compound (I), and it also does not describe a crystalline form and purity of the compound (I). The method of preparation described in Patent document 3 includes repetition of 3 times of the step of obtaining precipitates. Such method requiring the above procedures cannot be industrially applied, and methylene chloride and diethyl ether used therein are not industrially preferred solvents. For these reasons, it cannot be considered that the aforementioned precipitates of the compound (I) described in Patent document 3 have physicochemical properties and characteristics suitable for the drug substance of medicaments, and therefore, it is difficult to industrially prepare the compound (I) by this preparation method.

In the aforementioned prior art references, sofpironium bromide is prepared as the compound (I), i.e., a mixture of diastereomers (epimers), because the stereochemistry of the 1'-position cannot be controlled in the N-alkylation reaction. In addition, no references disclose nor suggest any crystalline form of sofpironium bromide, high-purity sofpironium bromide, and preparation methods thereof.

In general, few cases have been known where drug substances of medicaments consist of a mixture of diastereomers, and almost no general procedures or successful examples for obtaining a crystalline form having a profile suitable for drug substances of medicaments, have been known. In the aforementioned prior art references, sofpironium bromide is prepared as a mixture of diastereomers. However, the references do not disclose nor suggest the crystalline form thereof. Moreover, these references do not absolutely disclose nor suggest any crystalline form of sofpironium bromide having a profile suitable for a drug substance of medicaments, as well as preparation method for obtaining such a crystalline form.

CITATION LIST

Non Patent Literature

NPL 1: Pharmazie (2006), 61 (2), 90-96

Patent Literature

PTL 1: International. Patent Publication WO2015/138776
PTL 2: International Patent Publication WO2007/058971
PTL 3: International Patent Publication WO2018/026869

SUMMARY OF INVENTION

Technical Problem

Drug substances of medicaments are preferably supplied in a stable crystalline form, and in addition, they need to be supplied by a simple and industrially applicable, method. The aforementioned prior art references do not disclose any crystalline form of sofpironium bromide, and also do not suggest existence thereof. Accordingly, it cannot be expected whether a crystalline form of sofpironium bromide can be obtained as a single crystalline form, or as a mixture of several crystalline forms.

In view of such technical backgrounds as described above, an object to be achieved by the present invention is to provide sofpironium bromide having an optimal profile for a drug substance of medicaments.

Another object to be achieved by the present invention is to provide a crystalline form of sofpironium bromide having an optimal profile for a drug substance of medicaments.

Another object to be achieved by the present invention is to provide highly purified sofpironium bromide, in particular, a physicochemically stable crystalline form of high-purity sofpironium bromide.

Still another object to be achieved by the present invention is to provide an industrially applicable method for preparing such sofpironium bromide as mentioned above (including crystalline form thereof).

Solution to Problem

Aiming at the aforementioned objects, the inventors of the present invention variously researched with an effort to provide a crystalline form of sofpironium bromide having an optimal profile for a drug substance of medicaments.

The inventors of the present invention found that, even if the conditions of the N-alkylation reaction are variously changed in the preparation of sofpironium bromide, resulting sofpironium bromide inevitably contains the compound (I-a) and the compound (I-b), and the content ratio thereof is limited within a certain range. For example, in one embodiment of the present invention, the content ratio of the compound (I-a) and the compound (I-b) in the compound (I) obtainable by the N-alkylation reaction is from 50:50 to 10:90, and in a typical embodiment of the present invention, it is from 40:60 to 25:75.

As described above, the method of the reaction of compound (II) with ethyl bromoacetate (N-alkylation reaction) always provides sofpironium bromide containing the compound (I-a) and the compound (I-b) irrespective of the preparation conditions. Therefore, in order to supply the compound (I) as a drug substance of medicaments, the inventors of the present invention considered that supplying the compound (I-a) and the compound (I-b) after separation is not industrially practical, and it is absolutely essential to obtain the drug substance as a crystalline form of the compound (I), in a form of a mixture of the diastereomers (epimers), and use the crystalline form as a raw material of medicaments, from viewpoints of manufacturing costs and stable supply of medicaments.

In the course of researches on methods for providing a stable crystalline form of sofpironium bromide and for preparing such a crystalline form with an industrially applicable means, the inventors of the present invention succeeded in obtaining the compound (I) in a crystalline form for the first time by adding ethyl bromoacetate, which is not diluted with any solvents, into the compound (II) solution containing ethyl acetate as a solvent (the crystalline form of the compound (II) obtained by this preparation method is henceforth referred to as “Form A”.).

The inventors of the present invention then examined the profile of Form A in detail, The inventors of the present invention thus succeeded in obtaining each of them in a crystalline form using a mixed solvent of methyl t-butyl ether and ethyl acetate after separating the compound (I-a) and the compound (I-b) from the compound (I) by silica gel chromatography (the crystalline form of the compound (I-a) obtained by the aforementioned method is henceforth referred to as “Form MN”, and the crystalline form of the compound (I-b) obtained by the aforementioned method is henceforth referred to as “Form MJ”).

As a result of detailed studies, the inventors of the present invention revealed that Form MN exists as an extremely stable crystalline form and has a profile suitable for a drug substance of medicaments, whereas Form MJ causes crystal transition under humidified conditions.

The inventors of the present invention further revealed that Form A contains the compound (I-a) and the compound (I-b), and in addition, Form A is a crystal mixture of Form MN and Form MJ.

However, Form A caused crystal transition under humidified conditions, and was not considered to be most suitable for a drug substance of medicaments. Therefore, the inventors of the present invention performed further studies in order to search for a crystalline form having a profile more suitable for a drug substance of medicaments.

The compound (I) contains the compound (I-a) and the compound (I-b) at an arbitrary ratio. However, at the crystallization of the compound (I), it is absolutely unpredictable how a content ratio of the compound (I-a) and the compound (I-b) or a preparation method (crystallization method) may influence the crystalline form of the compound (I) as the product.

Therefore, the inventors of the present invention prepared the compound (I) containing the compound (I-a) and the compound (I-b) at various content ratios, and examined the influence of the content ratio thereof on the crystalline form of the compound (I).

As a result, it was surprisingly found that a novel crystalline form is formed under certain preparation conditions (crystallization conditions), which is neither Form MN nor Form MJ. As a result of examination, it was observed that this crystalline form has a cocrystal structure containing the compound (I-a) and the compound (I-b) at a ratio of 1:3 (this cocrystal is henceforth referred to as “Form CO”). Then, it was further surprisingly confirmed that Form CO has extremely superior properties as a drug substance of medicaments.

The inventors of the present invention studied the method for preparing Form CO in detail, and revealed that a step of adding methyl t-butyl ether dropwise over a long period of time, and/or a step of stirring a suspension comprising a crystalline form of the compound (I) in a solvent containing at least one of the solvents selected from ethyl acetate and methyl t-butyl ether over a long period of time is extremely important for the preparation of Form CO.

The inventors of the present invention considered that the crystalline form of the compound (I) containing Form CO can be a superior drug substance of medicaments, and further conducted researches on the preparation method thereof.

As a result, the inventors of the present invention succeeded in obtaining the crystalline form of the compound (I) containing Form CO by preparing a suspension comprising a crystalline form of the compound (I) in a solvent containing at least one of the solvents selected from ethyl acetate and methyl t-butyl ether and stirring the suspension over at least 1 hour (the crystalline form of the compound (I) obtained by this method is henceforth referred to as “Form B”).

The inventors of the present invention studied with effort to reveal the properties of Form B, and specifically analyzed by solid-state $^{13}C$ nuclear magnetic resonance spectrometry, powder X-ray crystal structure analysis, and the like. As a result, it was revealed that Form B comprises the crystal mixture of Form MN and Form CO. Further detailed studies revealed that Form B is a crystalline form having an optimal profile for a drug substance of medicaments.

It is also founded that high-purity sofpironium bromide (including crystalline form of sofpironium bromide) can be provided by the preparation method of the present invention, and thus the present invention was achieved.

As described above, the inventors of the present invention newly prepared Form CO (cocrystal containing the compound (I-a) and the compound (I-b) at a ratio of 1:3), which cannot be obtained in a single crystalline form by the method of simply treating the compound (I), and revealed that Form CO is stable without hygroscopic property, and has a superior profile for a drug substance of medicaments. It was further found that a crystalline form of the compound (I) that is a crystal mixture containing this Form CO (for example, Form B) is highly stable, and has an extremely excellent profile for a drug substance of medicaments.

Further, by the preparation method of the present invention, a highly stable crystalline form of sofpironium bromide was successfully obtained with high purity and in an industrial scale.

The inventors of the present invention thus accomplished the following inventions.

[1] A crystalline form that is a cocrystal of the compound (I) (sofpironium bromide) represented by the formula (I), comprising the compound (I-a) represented by the formula (I-a) and the compound (I-b) represented by the formula (I-b) at a ratio of 1:3.

[Chem. 5]

(I-a)

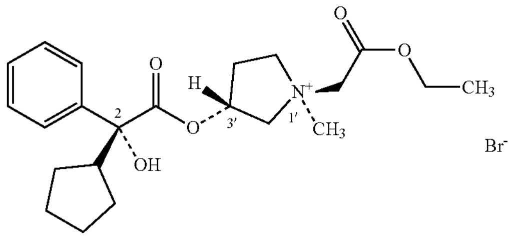

(2R, 3′R, 1′R)

-continued

[Chem. 6]

(I-b)

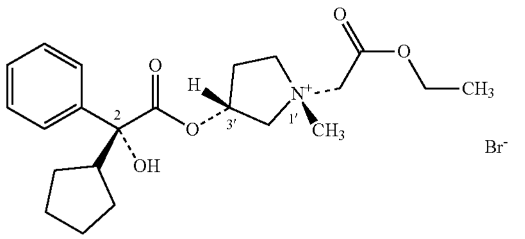

(2R, 3'R, 1'S)

[Chem. 7]

(I)

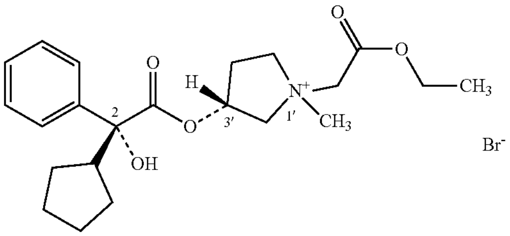

(2R, 3'R)

[2] The crystalline form according to [1], characterized by showing peaks at 5.9±0.2°, 7.6±0.2°, 11.0±0.2°, and 22.2±0.2° as diffraction angles 2θ in the powder X-ray diffraction spectrum (Form CO).

[3] A crystalline form of the compound (I), comprising the crystalline form according to [1] or [2], characterized by containing the compound (I-a) and the compound (I-b) at an arbitrary ratio.

[4] A crystalline form of the compound (I), wherein the crystalline form is a crystal mixture containing the crystalline form according to [1] or [2], and a crystalline form of the compound (I-a).

[5] A crystalline form of the compound (I), wherein the crystalline form is a crystal mixture containing the crystalline form according to [1] or [2], and a crystalline form of the compound (I-a) (Form MN) characterized by showing peaks at 7.1±0.2°, 21.4±0.2, 22.3±0.2°, and 24.5±0.2° as diffraction angles 2θ in the powder X-ray diffraction spectrum.

[6] A crystalline form of the compound (I), characterized by showing peaks at 5.9±0.2°, 7.2±0.2°, 7.7±0.2°, 11.1±0.2°, 22.3±0.2°, and 24.6±0.2° as diffraction angles 2θ in the powder X-ray diffraction spectrum (Form B).

[7] A method for preparing the crystalline form of the compound (I) according to any one of [1] to [6], comprising the following steps:

Step C: the step of preparing a suspension of the compound (I) in a solvent containing at least one of the solvents selected from ethyl acetate and methyl t-butyl ether, and stirring the suspension for at least 1 hour, and Step D: the step of filtering the aforementioned suspension of the compound (I) to obtain the crystalline form of the compound (I).

[8] A method for preparing the crystalline form of the compound (I) according to any one of [1] to [6], comprising the following steps:

Step A: the step of reacting the compound (II) represented by the formula (II):

[Chem. 8]

(II)

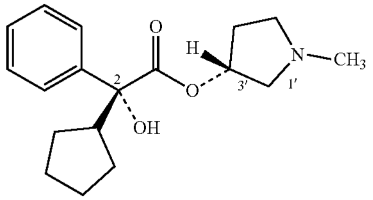

(2R, 3'R)

with ethyl bromoacetate in a solvent to prepare a reaction mixture containing the compound (I), Step B: the step of filtering the aforementioned reaction mixture to obtain a crystalline form of the compound (I), Step C': the step of preparing a suspension of the aforementioned crystalline form of the compound (I) in a solvent containing at least one of the solvents selected from ethyl acetate and methyl t-butyl ether, and stirring, the suspension for at least 1 hour, and Step D: the step of filtering the aforementioned suspension of the compound (I) to obtain the crystalline form of the compound (I).

[9] A crystalline form of the compound (I), wherein a content of the compound (III) represented by the following formula (IMI):

[Chem. 9]

(III)

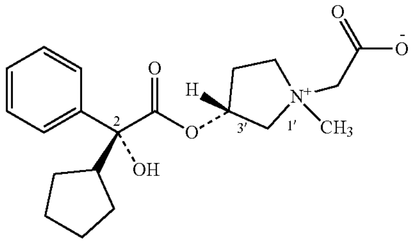

(2R, 3'R)

is not more than 0.5 w/w % based on a content of the compound (I).

[10] A crystalline form of the compound (I), wherein a content of the compound (IV) represented by the following formula (IV);

[Chem. 10]

(IV)

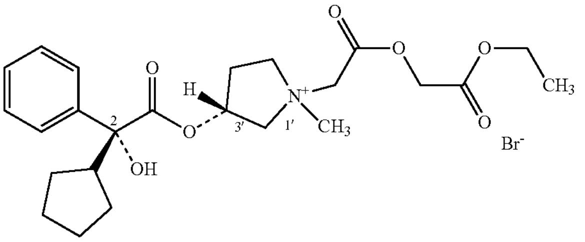

(2R, 3'R)

is not more than 0.5 w/w % based on the content of the compound (I).

[11] A crystalline form of the compound (I), wherein a content of the compound (V) represented by the following formula (V):

[Chem. 11]

(V)

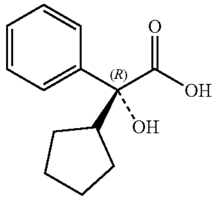

is not more than 0.5 w/w % based on the content of the compound (I).

[12] A crystalline form of the compound (I), wherein each of contents of the compounds (111), (IV), and (V) is not more than 0.5 w/w % based on the content of the compound (I), and purity of the compound (I) is not less than 98.0 w/w %.

[13] A crystalline form of the compound (I), wherein, based on the content of the compound (I), each of contents of the compounds (III), (IV), and (V) is not more than 0.5 w/w %, total content of impurities is not more than 2.0 w/w %, and purity of the compound (I) is not less than 98.0 w/w %.

[14] A crystalline form of the compound (I), wherein, based on the content of the compound (I), each of contents of the compounds (III), (IV), and (V) is not more than 0.15 w/w %, total content of impurities is not more than 1.0 w/w %, and purity of the compound (I) is not less than 99.0 w/w %.

[15] The crystalline form of the compound (I) according to any one of [9] to [14], comprising the compound (I-a) and the compound (I-b) at a content ratio of 40:60 to 20:80.

[16] A pharmaceutical composition for therapeutic and/or prophylactic treatment of a disease relating to an action of acetylcholine, wherein the composition is made by mixing the crystalline form of the compound (I) according to any one of [1] to [6], or any one of [9] to [15] and a pharmaceutically acceptable carrier.

[17] A pharmaceutical composition for therapeutic and/or prophylactic treatment of hyperhidrosis, wherein the composition is made by mixing the crystalline form of the compound (I) according to any one of [1] to [6], or any one of [9] to [15] and a pharmaceutically acceptable carrier.

[18] A pharmaceutical composition for therapeutic and/or prophylactic treatment of primary axillary hyperhidrosis or primary palm hyperhidrosis, wherein the composition is made by mixing the crystalline form of the compound (I) according to any one of [1] to [6], or any one of [9] to [15] and a pharmaceutically acceptable carrier.

[19] An anticholinergic agent that is made by mixing the crystalline form of the compound (I) according to any one of [1] to [6], or any one of [9] to [15] and a pharmaceutically acceptable carrier.

[20] A method for therapeutic and/or prophylactic treatment of a disease relating to an action of acetylcholine, comprising the step of administrating a pharmaceutical composition to a mammal including human, wherein the composition is made by mixing the crystalline form of the compound (I) according to any one of [1] to [6], or any one of [9] to [15] and a pharmaceutically acceptable carrier.

[21] A method for therapeutic and/or prophylactic treatment of hyperhidrosis, comprising the step of administrating a pharmaceutical composition to a mammal including human, wherein the composition is made by mixing the crystalline form of the compound (I) according to any one of [1] to [6], or any one of [9] to [15] and a pharmaceutically acceptable carrier.

[22] A method for therapeutic and/or prophylactic treatment of primary axillary hyperhidrosis or primary palm hyperhidrosis, comprising the step of administrating a pharmaceutical composition to a mammal including human, wherein the composition is made by mixing the crystalline form of the compound (I) according to any one of [1] to [6], or any one of [9] to [15] and a pharmaceutically acceptable carrier.

[23] Use of the crystalline form of the compound (I) according to any one of [1] to [6], or any one of [9] to [15] for preparation of an anticholinergic agent.

[24] Use of the crystalline form of the compound (I) according to any one of [1] to [6], or arty one of [9] to [15] for preparation of a pharmaceutical composition for treatment of a disease relating to an action of acetylcholine.

[25] Use of the crystalline form of the compound (I) according to any one of [1] to [6], or any one of [9] to [15] for preparation of a pharmaceutical composition for use in treatment of hyperhidrosis.

[26] Use of the crystalline form of the compound (I) according to any one of [1] to [6], or any one of [9] to [15] for preparation of a pharmaceutical composition for use in treatment of primary axillary hyperhidrosis or primary palm hyperhidrosis.

The present invention also encompasses the following inventions.

[2a] The crystalline form according to [1], characterized by showing peaks at 5.9±0.1°, 7.6±0.1°, 11.0±0.1°, and 22.2±0.1° as diffraction angles 2θ in the powder X-ray diffraction spectrum (Form CO).

[3a] A crystalline form of the compound (I), containing the crystalline form according to [2a] (Form CO), characterized by containing the compound (I-a) and the compound (I-b) at an arbitrary ratio.

[3b] The crystalline form according to [3] or [3a], containing the compound (I-a) and the compound (I-b) at a content ratio of 99:1 to 1:99.

[3c] The crystalline form according to [3] or [3a], containing the compound (I-a) and the compound (I-b) at a content ratio of 90:10 to 10:90.

[3d] The crystalline form according to [3] or [3a], containing the compound (I-a) and the compound (I-b) at a content ratio of 50:50 to 10:90.

[3e] The crystalline form according to [3] or [3a], containing the compound (I a) and the compound (I-b) at a content ratio of 40:60 to 20:80.

[3f] The crystalline form according to [3] or [3a], containing the compound (I-a) and the compound (I-b) at a content ratio of 40:60 to 25:75.

[3g] The crystalline form according to [3] or [3a], containing the compound (I-a) and the compound (I-b) at a content ratio of 40:60 to 30:70.

[4a] A crystalline form of the compound (I) according to any one of [3a] to [3g], wherein the crystalline form is a crystal mixture containing at least a crystalline form of the compound (I-a).

[4b] A crystalline form of the compound (I), containing at least the crystalline form according to [1], [2], or [2a], and wherein the crystalline form does not contain any crystalline form of only the compound (I-b).

[4c] A crystalline form of the compound (I) according to any one of [3a] to [3g] wherein the crystalline form does not contain any crystalline form of only the compound (I-b).

[4d] A crystalline form of the compound (I), wherein the crystalline four is a crystal mixture containing the crystalline form according to [1], [2] or [2a], and a crystalline form of the compound (I-a), wherein the crystalline form does not contain any crystalline form of only the compound (I-b).

[4e] A crystalline form of the compound (I) according to any one of [3a] to [3g], wherein the crystalline form is a crystal mixture containing a crystalline form of the compound (I-a) and does not contain any crystalline form of the compound (I-b).

[4f] A crystalline form of the compound (I) according to any one of [3a] to [3g], wherein the crystalline form is a crystal mixture containing the crystalline form according to [1], [2], or [2a], and a crystalline form of the compound (I-a), and does not contain any crystalline form of only the compound (I-b).

[5a] A crystalline form of the compound (I) wherein the crystalline form is a crystal mixture containing the crystalline form according to [1], [2], or [2a], and a crystalline form of the compound (I-a) (Form MN) characterized by showing peaks at 7.1±0.1°, 21.4±0.1°, 22.3±0.1°, and 24.5±0.1° as diffraction angles 2θ in the powder X-ray diffraction spectrum.

[5b] A crystalline form of the compound (I) according to any one of [3a] to [3g], containing a crystalline form of the compound (I-a) (Form MN) characterized by showing peaks at 7.1±0.1°, 21.4±0.1°, 22.3±0.1°, and 24.5±0.1° as diffraction angles 2θ in the powder X-ray diffraction spectrum.

[6a] A crystalline form of the compound (I), characterized by showing peaks at 5.9±0.2°, 7.2±0.2°, 7.7±0.2°, 11.1±0.2°, 22.3±0.2°, and 24.6±0.2° as diffraction angles 2θ in the powder X-ray diffraction spectrum, containing the compound (I-a) and the compound (I-b) at a content ratio of 99:1 to 1:99.

[6b] A crystalline form of the compound (I), characterized by showing peaks at 5.9±0.2°, 7.2±0.2°, 7.7±0.2°, 11.1±0.2°, 22.3±0.2°, and 24.6±0.2° as diffraction angles 2θ in the powder X-ray diffraction spectrum, containing the compound (I-a) and the compound (I-b) at a content ratio of 90:10 to 10:90.

[6c] A crystalline form of the compound (I), characterized by showing peaks at 5.9±0.2°, 7.2±0.2°, 7.7±0.2°, 11.1±0.2°, 22.3±0.2°, and 24.6±0.2° as diffraction angles 2θ in the powder X-ray diffraction spectrum, containing the compound (I-a) and the compound (I-b) at a content ratio of 50:50 to 10:90.

[6d] A crystalline form of the compound (I), characterized by showing peaks at 5.9±0.2°, 7.2±0.2°, 7.7±0.2°, 11.1±0.2°, 22.3±0.2°, and 24.6±0.2° as diffraction angles 2θ in the powder X-ray diffraction spectrum, containing the compound (I-a) and the compound (I-b) at a content ratio of 40:60 to 20:80.

[6e] A crystalline form of the compound (I), characterized by showing peaks at 5.9±0.2°, 7.2±0.2°, 7.7±0.2°, 11.1±0.2°, 22.3±0.2°, and 24.6±0.2° as diffraction angles 2θ in the powder X-ray diffraction spectrum, containing the compound (I-a) and the compound (I-6) at a content ratio of 40:60 to 25:75.

[6f] A crystalline form of the compound (I), characterized by showing peaks at 5.9±0.2°, 7.2±0.2°, 7.7±0.2°, 11.1±0.2°, 22.3±0.2°, and 24.6±0.2° as diffraction angles 2θ in the powder X-ray diffraction spectrum, containing the compound (I-a) and the compound (I-b) at a content ratio of 40:60 to 30:70.

[6g]A crystalline form of c compound (j), characterized by showing peaks at 5.9±0.1°, 7.2±0.1°, 7.7±0.1°, 11.1±0.1°, 22.3±0.1. °, and 24.6±0.1° as diffraction angles 2θ in the powder X-ray diffraction spectrum (Form B).

[6h] A crystalline form of the compound (I), characterized by showing peaks at 5.9±0.1°, 7.2±0.1°, 7.7±0.1°, 11.1±0.1°, 22.3±0.1°, and 24.6±0.1° as diffraction angles 2θ in the powder X-ray diffraction spectrum, containing the compound (I-a) and the compound (I-b) at a content ratio of 99:1 to 1:99.

[6i] A crystalline form of the compound (I), characterized by showing peaks at 5.9±0.1°, 7.2±0.1°, 7.7±0.1°, 11.1±0.1°, 22.3±0.1°, and 24.6±0.1° as diffraction angles 2θ in the powder X-ray diffraction spectrum, containing the compound (I-a) and the compound (I-b) at a content ratio of 90:10 to 10:90.

[6j] A crystalline form of the compound (I), characterized by showing peaks at 5.9±0.1°, 7.2±0.1°. 7.7±0.1°, 11.1±0.1°, 22.3±0.1°, and 24.6±0.1° as diffraction angles 2θ in the powder X-ray diffraction spectrum, containing the compound (I-a) and the compound (I-b) at a content ratio of 50:50 to 10:90.

[6k] A crystalline form of the compound (I), characterized by showing peaks at 5.9±0.1°, 7.2±0.1°, 7.7±0.1°, 11.1±0.1°, 22.3±0.1°, and 24.6±0.1° as diffraction angles 2θ in the powder X-ray diffraction spectrum, containing the compound (I-a) and the compound (I-b) at a content ratio of 40:60 to 20:80.

[6l] A crystalline form of the compound (I), characterized by showing peaks at 5.9±0.1°, 7.2±0.1°, 7.7±0.1°, 11.1±0.1°, 22.3±0.1°, and 24.6±0.1° as diffraction angles 2θ in the powder X-ray diffraction spectrum, containing the compound (I-a) and the compound (I-b) at a content ratio of 40:60 to 25:75.

[6m] A crystalline form of the compound (I), characterized by showing peaks at 5.9±0.1°, 7.2±0.1°, 7.7±0.1°, 11.1±0.1°, 22.3±0.1°, and 24.6±0.1° as diffraction angles 2θ in the powder X-ray diffraction spectrum, containing the compound (I-a) and the compound (I-b) at a content ratio of 40:60 to 30:70.

[6o] A crystalline form of the compound (I), containing the crystalline form according, to [1], characterized by showing peaks at 5.9±0.2°, 7.2±0.2°, 7.7±0.2°, 11.1±0.2°, 22.3±0.2°, and 24.6±0.2° as diffraction angles 2θ in the powder X-ray diffraction spectrum.

[6p] A crystalline form of the compound (I), containing the crystalline form according to [1], characterized by showing peaks at 5.9±0.1°, 7.2±0.1°, 7.7±0.1°, 11.1±0.1°, 22.3±0.1°, and 24.6±0.1° as diffraction angles 2θ in the powder X-ray diffraction spectrum.

[7a] A method for preparing the crystalline form of the compound (I) according to any one of [1] to [6], the crystalline form of the compound (I) according to any one of [2a] to [6p], or the compound (I) according to any one of [9] to [15], containing the following steps:

Step C'': the step of preparing a suspension of the compound (I) in a solvent containing ethyl acetate and methyl t-butyl ether at least, and stirring the suspension for at least 1 hour, and Step D: the step of filtering the aforementioned suspension of the compound (I) to obtain the crystalline form of the compound (I).

[8a] A method for preparing the compound (I) according to any one of [9] to [15], containing:

Step A': the step of reacting the compound (II) represented by the formula (II):

[Chem. 12]

(II)

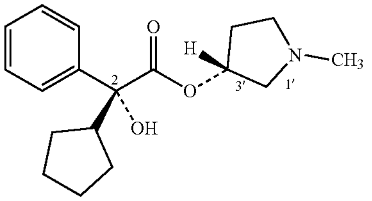

(2R, 3'R)

with ethyl bromoacetate in a solvent containing ethyl acetate to prepare a reaction mixture containing the compound (I), and Step B: the step of filtering the aforementioned reaction mixture to obtain a crystalline form of the compound (I).

[8b] A method for preparing the crystalline form of the compound (I) according to any one of [1] to [6], the crystalline form of the compound (I) according to any one of [2a] to [6p], or the compound (I) according to any one of [9] to [15], containing the following steps:

Step A': the step of reacting the compound (II) represented by the formula (II):

[Chem. 13]

(II)

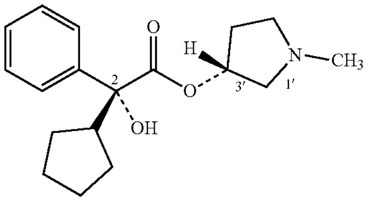

(2R, 3'R)

with ethyl bromoacetate in a solvent containing ethyl acetate to prepare a reaction mixture containing the compound (I), Step B: the step of filtering the aforementioned reaction mixture to obtain a crystalline form of the compound (I), Step C''': the step of preparing a suspension of the aforementioned crystalline farm of the compound (I) in a solvent containing at least ethyl acetate and methyl t-butyl ether, and stirring the suspension for at least 1 hour, and Step D: the step of filtering the aforementioned suspension of the compound (I) to obtain a crystalline form of the compound (I).

[9a] A compound (I), wherein the content of the compound (III) represented by the following formula (III):

[Chem. 14]

(III)

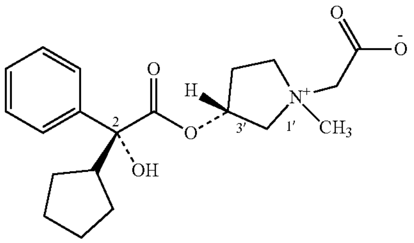

(2R, 3'R)

is not more than 0.5 w/w % based on the content of the compound (I).

[10a] A compound (T), wherein the content of the compound (IV) represented by the following formula (IV):

[Chem. 15]

(IV)

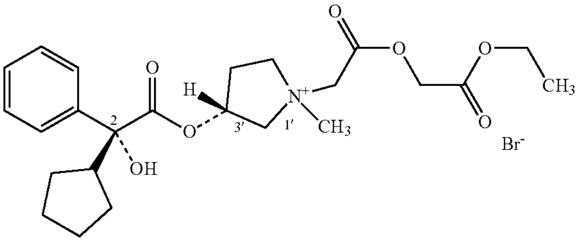

(2R, 3'R)

is not more than 0.5 w/w % based on the content of the compound (I).

[11a] A compound (I), wherein the content of the compound (V) represented by the following formula (V):

[Chem. 16]

(V)

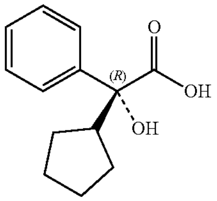

is not more than 0.5 w/w % based on the content of the compound (I).

[12a] A compound (I), wherein each of contents of the compounds (III), (IV), and (V) is not more than 0.5 w/w % based on the content of the compound (I), and purity of the compound (I) is not less than 98.0 w/w %.

[13a] A compound (I), wherein, based on the content of the compound (I), each of contents of the compounds (III), (IV), and (V) is not more than 0.5 w/w %, total content of impurities is not more than 2.0 w/w %, and parity of the compound (I) is not less than 98.0 w/w %.

[14a] A compound (I), wherein, based on the content of the compound (I), each of contents of the compounds (III), (IV), and (V) is not more than 0.15 w/w %, total content of impurities is not more than 1.0 w/w %, and purity of the compound (I) is not less than 99.0 w/w %.

[15a] The compound (I) according to any one of [9a] to [14a], containing the compound (I-a) and the compound (I-b) at a content ratio of 40:60 to 20:80.

[16a] A pharmaceutical composition for therapeutic and/or prophylactic treatment of a disease relating to an action of acetylcholine, containing the compound (I) according to any one of [9a] to [15a] as an active ingredient.

[17a] A pharmaceutical composition for therapeutic and/or prophylactic treatment of hyperhidrosis, containing the compound (I) according to any one of [9a] to [15a] as an active ingredient.

[18a] A pharmaceutical composition for therapeutic and/or prophylactic treatment of primary axillary hyperhidrosis or primary palm hyperhidrosis, containing the compound (I) according to any one of [9a] to [15a] as an active ingredient.

[19a] An anticholinergic agent, containing the compound (I) according to any one of [9a] to [15a] as an active ingredient.

[20a] A method for therapeutic and/or prophylactic treatment of a disease relating to an action of acetylcholine, containing the step of administrating a therapeutically and/or prophylactically effective amount of the compound (I) according to any one of [9a] to [15a] to a mammal including human.

[21a] A method for therapeutic and/or prophylactic treatment of hyperhidrosis, containing the step of administrating a therapeutically and/or prophylactically effective amount of the compound (I) according to any one of [9a] to [15a] to a mammal including human.

[22a] A method for therapeutic and/or prophylactic treatment of primary axillary hyperhidrosis or primary palm hyperhidrosis, containing the step of administrating a therapeutically and/car prophylactically effective amount of the compound (I) according to any one of [9a] to [15a] to a mammal including human.

[23a] Use of the compound (I) according to any one of [9a] to [15a] for preparation of an anticholinergic agent.

[24a] Use of the compound (I) according to any one of [9a] to [15a] for preparation of a pharmaceutical composition for use in treatment of a disease relating to an action of acetylcholine.

[25a] Use of the compound (I) according to any one of [9a] to [15a] for preparation of a pharmaceutical composition for use in treatment of hyperhidrosis.

[26a] Use of the compound (I) according to any one of [9a] to [15a] for preparation of a pharmaceutical composition for use in treatment of primary auxiliary hyperhidrosis or primary palm hyperhidrosis.

The present invention also encompasses the following inventions.

[9b] The crystalline form of the compound (I) according to any one of [1] to [6], wherein the content of the compound (III) represented by the following formula (III):

[Chem. 17]

(III)

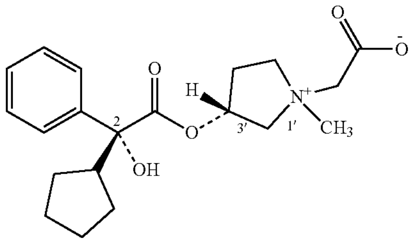

(2R, 3'R)

is not more than 0.5 w/w % based on the content of the compound (I).

[10b] The crystalline form of the compound (I) according to any one of [1] to [6], wherein the content of the compound (IV) represented by the following formula (IV):

[Chem. 18]

(IV)

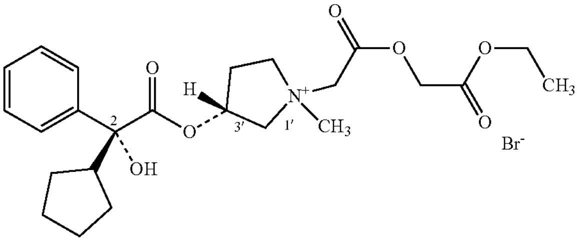

(2R, 3'R)

is not more than 0.5 w/w % based on the content of the compound (I).

[11b] The crystalline form of the compound (I) according to any one of [1] to [6], wherein the content of the compound (V) represented by the following formula (V):

[Chem. 19]

(V)

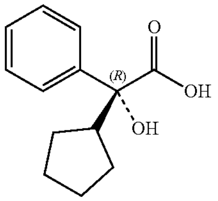

is not more than 0.5 w/w % based on the content of the compound (I).

[12b] The crystalline form of the compound (I) according to any one of [1] to [6], wherein each of contents of the compounds (III), (IV), and (V) is not more than 0.5 w/w % based on the content of the compound (I), and purity of the compound (I) is not less than 98.0 w/w %.

[13b] The crystalline form of the compound (I) according to any one of [1] to [6], wherein, based on the content of the compound (I), each of contents of the compounds (IV), and (V) is not more than 0.5 w/w %, total content of impurities is not more than 2.0 w/w %, and purity of the compound (I) is not less than 98.0 w/w %.

[14b] The crystalline form of the compound (I) according to any one of [1] to [6], wherein, based on the content of the compound (I), each of contents of the compounds (III), (IV), and (V) is not more than 0.15 w/w %, total content of impurities is not more than 1.0 w/w %, and purity of the compound (I) is not less than 99.0 w/w %.

[1.5b] The crystalline form of the compound (I) according to any one of [9b] to [14b], containing the compound (I-a) and the compound (I-b) at a content ratio of 99:1 to 1:99.

[15c] The crystalline form of the compound (I) according to any one of [9b] to [14b], containing the compound (I-a) and the compound (I-b) at a content ratio of 50:50 to 10:90.

[15d] The crystalline form of the compound (I) according to any one of [9b] to [14b], containing the compound (I-a) and the compound (I-b) at a content ratio of 40:60 to 20:80.

[15e] The crystalline form of the compound (I) according to any one of [9b] to [14b], containing the compound (I-a) and the compound (I-b) at a content ratio of 40:60 to 25:75.

[15f] The crystalline form of the compound (I) according to any one of [9b] to [14b], containing the compound (I-a) and the compound (I-b) at a content ratio of 40:60 to 30:70.

Advantageous Effects of Invention

Form CO, which is one embodiment of the crystalline form of sofpironium bromide of the present invention, does not have any hygroscopic property, and is extremely stable, and accordingly, it is preferable as a drug substance of medicaments.

Form B, which is another embodiment of the crystalline form of sofpironium bromide of the present invention, is a crystalline form containing Form (X) and Form MN, does not have any hygroscopic property, and is extremely stable, and accordingly, it can be used as a drug substance of medicaments.

The method for preparing a crystal mixture of sofpironium bromide of the present invention (for example, Form B) can be performed by simple operations suitable for industrial scale, and a crystal mixture of high-purity sofpironium bromide can be provided at a high yield.

DESCRIPTION OF EMBODIMENTS

Figure 1:
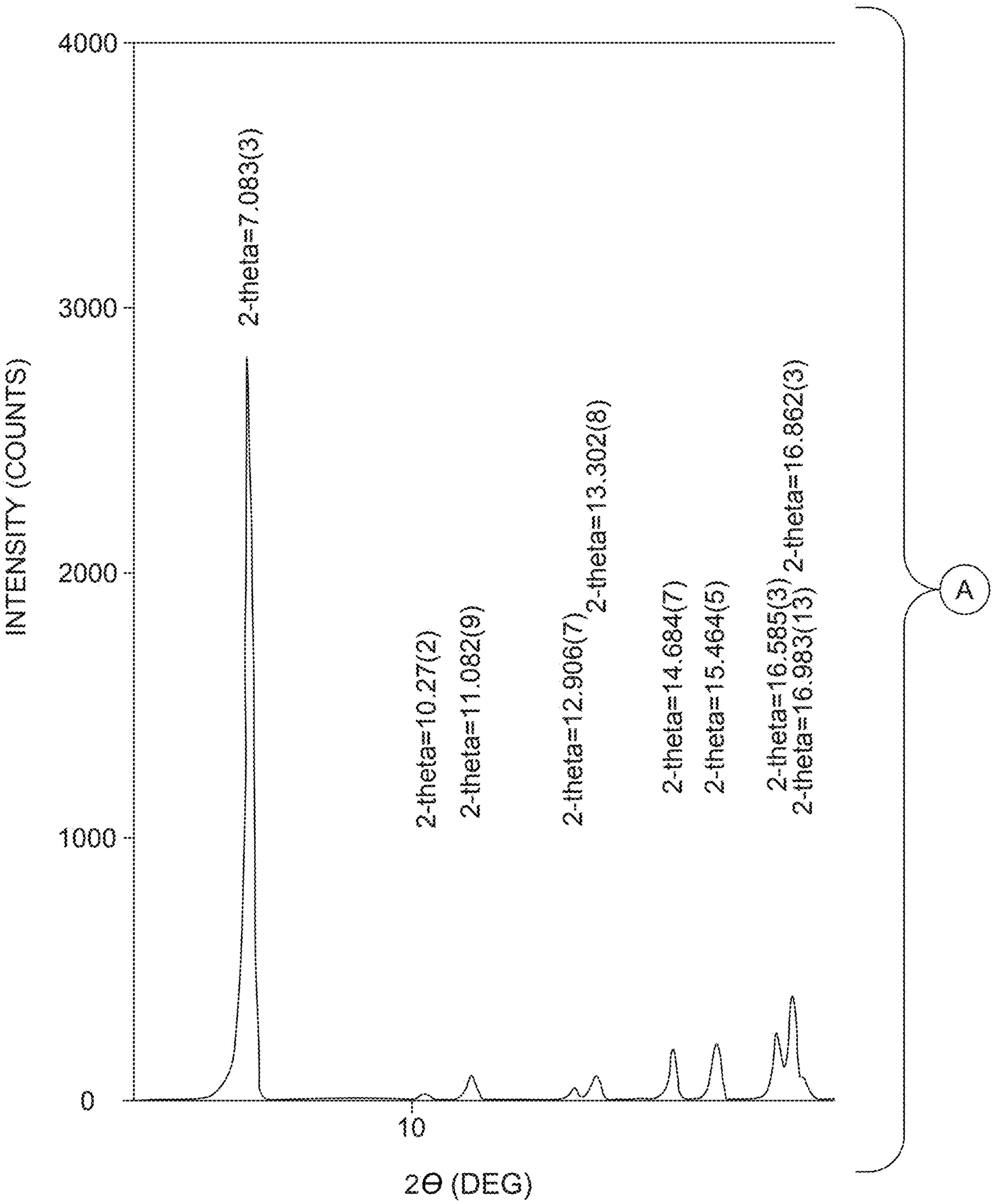
FIG. 1 Powder X-ray diffraction spectrum of the crystalline form (Form MN) of the compound (I-a) prepared in Preparation Example 4.

Hereafter, the details of the present invention are explained.

In the specification, the term "compound (I)" refers to a mixture of the compound (I-a) and the compound (I-b). The content ratio of the compound (I-a) and the compound (I-b) (the term "content ratio" henceforth means weight ratio unless especially indicated) is not particularly limited, and the content ratio can be in the range of 99:1 to 1:99, for example.

In the specification, the content ratio of the compound (I-a) and the compound (I-b) contained in the drug substance, solution, suspension, preparation, or crystalline form of the compound (I) is preferably 50:50 to 10:90, more preferably 45:55 to 20:80, further preferably 40:60 to 20:80.

In another embodiment of the present invention, the content ratio of the compound (I-a) and the compound (I-b) contained in the compound (I) is preferably 40:60 to 25:75.

In another embodiment of the present invention, the content ratio of the compound (I-a) and the compound (I-b) contained in the compound (I) is preferably 40:60 to 30:70.

In the specification, numerical ranges encompass the values defining the ranges as the maximum and minimum values unless especially indicated. For example, "1 to 99" means a range of not less than 1 and not more than 99.

In the specification, the term "crystalline form" refers to a solid in which constituting elements (molecules) form a three-dimensional repetitive structure called crystal lattice, or a mixture of such solids, and it is distinguished from amorphous (amorphous solid) that does not have such a repetitive structure.

In the specification, the term "crystalline form" encompasses various crystals, and also includes cocrystal comprising a plurality of constituents (preferably several kinds of organic compound molecules, further preferably two kinds of organic compound molecules) in a single crystal lattice, and mixture of a plurality of kinds of single crystals, Therefore, when a crystalline form is prepared from a mixture containing two or more kinds of compounds, the crystalline form may be, for example, a single crystal consisting only of a single kind of compound, a mixture of two or more kinds of crystal polymorphs of a single kind of compound, a single kind of cocrystal constituted by a plurality of kinds of compounds, a mixture of crystals containing a plurality of kinds of such crystals, and the like.

In the specification, the term "crystal mixture" means a mixture of a plurality of kinds of crystals, which is a kind of crystalline form.

In general, in most cases, a crystalline form of low molecular weight compounds such as sofpironium bromide show peaks around a specific diffraction angle (2θ) in the powder X-ray diffraction spectrum, peaks at a specific chemical shift value in solid-state $^{13}C$ nuclear magnetic resonance spectrometry (solid-state $^{13}C$-NMR), specific endothermic peaks in differential scanning calorimetry (DSC), and absorption hands at a specific wavelength in infrared absorption spectrometry (IR). However, such instrumental analyses may sometimes not be appropriately performed for crystalline forms depending on properties or quality of each crystalline form.

In the specification, the analysis based on X-ray diffraction means powder X-ray diffraction spectrometry, unless particularly indicated, and it can be performed in a conventional manner, for example, according to the "powder X-ray diffractometry method" described in Japanese Pharmacopoeia (17th Edition), Diffraction angle 2θ values of the same crystalline forms generally correspond with each other with a margin of ±0.2° or ±0.1°.

In the specification, the described peaks values of diffraction angle 2θ means to have at least the described peak values. For example, "show peaks at 5.9±0.2°, 7.6±0.2°, 11.0±0.2°, and 22.2±0.2° as diffraction angles 2θ in the powder X-ray diffraction spectrum" means to have at least 5.9±0.2°, 7.6±0.2°, 11.0±0.2°, and 22.2±0.2° and other peaks may be observed. The peak intensities of 5.9±0.2°, 7.6±0.2°, 11.0±0.2°, and 22.2±0.2° are not limited as long as it can be distinguished from the others.

In the powder X-ray diffraction spectrometry mentioned in the specification, samples obtained from the preparation process were subjected only to powderization without any pretreatment such as pulverization and sieving, and measured directly. However, samples may be pretreated, if needed.

The solid-state nuclear magnetic resonance spectrometry (solid-state $^{13}C$-NMR) mentioned in the specification was performed by the CP/MAS method, unless especially indicated. The CP/MAS method is widely used for measurement of nuclide of low natural abundance such as $^{13}C$ and $^{15}N$, and enables observation of the same chemical shifts as the spectrum of solution by the use of cross polarization (CP) (cross relaxation) method and magic angle spinning (MAS).

The analysis based on differential scanning calorimetry (DSC) mentioned in the specification can be performed in a conventional manner, for example, according to the description of Japanese Pharmacopoeia (17th Edition), "Thermal analysis", and the like. In the specification, the term "endothermic peak" means a temperature corresponding to the top of peak, and it may slightly vary depending on the measurement conditions. Although the range of measurement error that may possibly occur varies depending on the measurement conditions or test material, it can be supposed to be within a range of, for example, ±5° C. or ±2° C. This means that the "endothermic peak" values of the same crystalline forms correspond with each other with a margin within the range of ±5° C. or ±2° C.

The analysis based on infrared absorption spectrometry mentioned in the specification can be performed in a conventional manner, for example, according to the "Infrared absorption spectrometry method" described in Japanese Pharmacopoeia (17th Edition), and the like. The wave number at which absorption is observed and intensity thereof may slightly vary depending on the measurement conditions, and the like. The range of measurement error that may occur for an absorption band ($cm^{-1}$) is supposed to be usually in the range of ±0.5%, or ±5 $cm^1$. In such a case, the values of the absorption band ($cm^{-1}$) of the same crystalline forms correspond with each other with a margin of ±0.5% or ±5 $cm^1$.

Hereafter, the details of the crystalline forms of the compound (I), compound (I-a), and compound (I-b) described in the specification are explained.

The compound (I) is a mixture of the compound (La) and the compound (I-b). And the crystalline form of the compound (I) varies depending on the content ratio thereof and preparation method (for example, crystallization method) as shown in the test examples mentioned later.

Form CO is one of the crystalline forms of the compound (I), and is a cocrystal comprising the compound (I-a) and the compound (I-b) at a content ratio of 1:3. The compound (I-a) and the compound (I-b) are epimers with each other. In general, a single cocrystal formed by such two kinds of epimers is extremely rare, and there is almost no report of such a cocrystal.

Fortin CO is thermally stable, in particular, it does not show crystal transition under humidification, and thus is an extremely stably crystalline form. Form CO is the form of white solid, has a non-hygroscopic property, and is easy for handling such as in filtration from a suspension.

Form CO has such properties as described above, and therefore Form CO is one of the preferred crystalline forms of the compound (I).

Form CO can be prepared by, for example, the method comprising the following steps, using the compound (I) having a content ratio of the compound (I-a) and the compound (I-b) of 1:3 as a raw material:

Step C: the step of preparing a suspension of the compound (I) in a solvent containing at least one of the solvents selected from ethyl acetate and methyl t-butyl ether, and stirring the suspension for at least 1 hour, and Step D: the step of filtering the aforementioned suspension of the compound (I) to obtain the crystalline form of the compound (I), However, the method for preparing Form CO is not limited to the aforementioned specific method.

The compound (I) is a mixture of the compound (I-a) and the compound (I-b) mixed at an arbitrary ratio, for this reason, it is usually difficult to obtain only Form CO by preparing a crystalline form according to the aforementioned preparation method using the compound (I) as a raw material, and such preparation results in a crystal mixture of Form CO and another crystalline form.

Form CO has a profile extremely superior for a drug substance of medicaments. Accordingly, a crystalline form of the compound (I) containing a large amount of Form CO has a profile suitable for a drug substance of medicaments. For example, a crystalline form of the compound (I) containing not less than 50% of Form CO as the weight ratio in the compound (I) is preferred, a crystalline form of the compound (I) containing not less than 60% of Form CO is more preferred, and a crystalline form of the compound (I) containing not less than 80% of Form CO is further preferred.

Form MN is a crystalline form of the compound (I-a), Form MN is thermally stable, in particular, it does not show crystal transition under humidification, and is an extremely stably crystalline form, Form MN is the form of white solid, has a non-hygroscopic property, and is easy for handling such as in filtration from a suspension.

Form MN has the above properties, and therefore Form MN has a superior profile for a drug substance of medicaments.

Form MJ is a crystalline form of the compound (I-b). Form MJ is the form of white solid, and is easy for handling such as in filtration from a suspension. However, Form MJ shows crystal transition under humidification, and there arc many crystal polymorphs thereof.

Form MJ has the above properties, and therefore it is not considered that Form MJ has an optimal profile for a drug substance of medicaments.

Form A is one of the crystalline forms of the compound (I). Form A is a crystal mixture comprising of Form MN and Form MT, The compound (I-a) in the compound (I) forms Form MN, and the compound (I-b) in the compound (I) forms Form MJ, and accordingly, the content ratio of Form MN and Form MJ constituting Form A depends on the content ratio of the compound (I-a) and the compound (I-b). For example, when the content ratio of the compound (I-a) and the compound (I-b) is 1:2, the content ratio of Form MN and Form NJ also becomes about 1:2.

Form A shows crystal transition under humidified conditions, because the crystalline form includes Form MJ, and it is not considered that Form A has an optimal profile for a drug substance of medicaments.

Form B is one of the crystalline forms of the compound (I). Form B is a crystal mixture comprising of Form CO and Form MN.

The content ratios (weight ratio) of Form CO and Form MN constituting Form B is 99:1 to 50:50, preferably 96:4 to 60:40, further preferably 92:8 to 80:20.

The content ratio of Form CO and Form MN constituting Form B is determined depending on the content ratio of the compound (I-a) and the compound (I-b) contained in the compound (I) used as a raw material. For example, when the content ratio of the compound (I-a) and the compound (I-b) is 1:2, the content ratio of Form CO and Form MN contained in Form B is about 89:11.

Since Form CO and Form MN have a superior profile for a drug substance of medicaments as described above. Form B, which is a mixture of them, has the best profile for a drug substance of medicaments. This means that Form B is thermally stable, in particular, it does not show crystal transition under humidification, and is an extremely stably crystalline form. Further. Form B is the form of white solid, has a non-hygroscopic property, and is easy for handling such as in filtration from a suspension.

Form B not containing Form 141.1 is a particularly preferred embodiment,

Form B is prepared by using the aforementioned method for preparing Form CO.

Form B not substantially containing Form MJ is prepared by the aforementioned method for preparing Form CO using the compound (I) as a raw material in which a content of the compound (I-a) is not less than 25%.

High-purity Form B can be prepared in an industrial scale by using the preparation method of the present invention.

Form B has such characteristics and properties as mentioned above, and therefore Form B is a preferred crystalline form for industrially preparing and providing a crystalline form of sofpironium bromide, and Form B not containing Form MJ is a particularly preferred crystalline form.

In the specification, the term "crystalline form of the compound (I)" encompasses the aforementioned crystalline forms and mixtures thereof, for example, a mixture of Form MJ and Form MN (for example, Form A), a mixture of Form CO and Form MN (for example, Form B), and a mixture of Form CO and Form MJ.

In the specification, the term "crystalline form of the compound (I-a)" refers to a crystalline form comprising substantially and solely of the compound (I-a) (for example, Form MN).

In the specification, the term "crystalline form of the compound (I-b)" refers to a crystalline form comprising substantially and solely of the compound (I-b) (for example, Form MJ).

In the specification, the term "crystalline form of the present invention" refers to a crystalline form containing Form CO, for example, Form B, among the crystalline forms of the compound (I).

In the present invention, a preferred crystalline form of the compound (I) is a crystalline form containing Form CO, a more preferred crystalline form of the compound (I) is a crystal mixture containing Form CO and Form MN, and a still more preferred crystalline form of the compound (I) is a crystal mixture containing Form CO and Form MN, and not substantially containing Form MJ.

Hereafter, the details of the method for preparing sofpironium bromide according to one embodiment of the present invention are explained for each of the steps described in [7], and the like, mentioned above. By using the preparation method of the present invention, the crystalline form of the present invention (for example, Form B) can be obtained at a high purity. This preparation method can be applied in an industrial scale.

According to one embodiment of the present invention, the preparation method of the present invention comprises:

Step C: the step of preparing a suspension of the compound (I) in a solvent containing at least one of the solvents selected from ethyl acetate and methyl t-butyl ether, and stirring the suspension for at least 1 hour, and Step D: the step of filtering the aforementioned suspension of the compound (I) to obtain a crystalline form of the compound (I).

In Step C mentioned above, the compound (I) used as a raw material is preferably, but not limited to, a crystalline form of sofpironium bromide.

Step C encompasses both a recrystallization step and a slurry-washing step. After a solution of the compound (I) is prepared, recrystallization may be performed, or only slurry-washing may be performed.

The "solvent containing at least one of the solvents selected from ethyl acetate and methyl t-butyl ether" used in Step C may be a solvent comprising any one of only ethyl acetate, a solvent consisting of only methyl t-butyl ether, a mixed solvent of ethyl acetate and methyl t-butyl ether, a mixed solvent of ethyl acetate or methyl t-butyl ether and another solvent, a mixed solvent of ethyl acetate, methyl t-butyl ether, and another solvent, and the like.

Preferred solvent used in Step C comprises any one of only ethyl acetate, a mixed solvent of ethyl acetate anal acetonitrile, a mixed solvent of ethyl acetate and methyl t-butyl ether, and a mixed solvent of ethyl acetate, acetonitrile, and methyl t-butyl ether. A more preferred example of the solvent is a mixed solvent of ethyl acetate, methyl t-butyl ether, and acetonitrile.

Although the amount of the solvent containing at least one of the solvents selected from ethyl acetate and methyl t-butyl ether is not particularly limited, the amount is preferably a volume (L) of 3 to 40 times, more preferably a volume (L) of 5 to 30 times (L), further preferably a volume (L) of 8 to 20 times (L), still further preferably a volume (L) of 10 to 15 times (L), of the weight (kg) of the compound (I).

In the specification, the term "suspension" or "slurry" refers to a dispersion system in which solid particles exist in a liquid, and the both terms are used synonymously.

In Step C, the stirring time refers to the period of time for which the suspension of the compound (I) is stirred, and specifically the period of time from generation of solid particles of the compound (I) in the solution to the end of the stirring. For example, when seed crystals are added to a solution of the compound (I), the aforementioned stirring time means the period of time from the time point of adding the seed crystals to the end of stirring. When ethyl acetate or methyl t-butyl ether is added to a solution of the compound (I) (including the case of adding dropwise) without adding seed crystals, the stirring time of Step C means the period of time from veneration of solid particles of the compound (I) in the solution to the end of stifling. When a solution of the compound (I) is not used in Step C (i.e., when only slurry-washing is performed) the stirring time of Step C is the period of time from the time point of mixing the compound (I) and a solvent containing ethyl acetate or methyl t-butyl ether to the end of stirring.

The stirring time of Step C is not less than 1 hour, preferably not less than 2 hours, more preferably not less than 3 hours, still more preferably not less than 4 hours, further preferably not less than 5 hours.

In another embodiment of the present invention, the mixing time in Step C is preferably not less than 1 hour and not more than 72 hours, more preferably not less than 1 hour and not more than 48 hours, still more preferably not less than 1 hour and not more than 24 hours.

When ethyl acetate or methyl t-butyl ether is added dropwise, although dropping time is not particularly limited, it is preferably not less than 30 minutes, more preferably not less than 1 hour, further preferably not less than 3 hours, still further preferably not less than 4 hours and not more than 72 hours, particularly preferably not less than 5 hours and not more than 72 hours.

In another embodiment of the present invention, the preparation method of the present invention may comprise, instead of Step C.

Step C-1: the step of dissolving the compound (I) in a solvent containing acetonitrile to obtain a solution of the compound (I), and Step C-2: the step of mixing the solution of the compound (I) and a poor solvent containing at least one of the solvents selected from ethyl acetate and methyl t-butyl ether to prepare a suspension of the compound (I), and stirring the suspension for at least 1 hour.

In the aforementioned Step C-1, the compound (I) is preferably completely dissolved in a solvent containing acetonitrile. The expression "completely dissolve" means that dissolve the compound (I) to the extent of visually unobserved, and generally a colorless or colored clear solution of the compound (I) is obtained.

The "solvent containing acetonitrile" used in Step C-1 encompasses a solvent consisting only of acetonitrile, and a mixed solvent of acetonitrile and another solvent. The "solvent containing acetonitrile" is preferably a mixed solvent of acetonitrile and ethyl acetate. When a mixed solvent of acetonitrile and ethyl acetate, is used, the ratio thereof is preferably in the range of 90:10 to 10:90, more preferably in the range of 60:40 to 40:60, although the ratio can be appropriately changed in the range of 99:1 to 1:99. Another solvent may be optionally added to a mixed solvent of acetonitrile and ethyl acetate.

When a mixed solvent of acetonitrile and ethyl acetate is used as the "solvent, containing acetonitrile", ethyl acetate may be added stepwise so that an acetonitrile solution of the compound (I) is obtained, if needed. For example, the compound (I) may be dissolved in acetonitrile, and then ethyl acetate may be added, or the compound (I) may be dissolved in a mixed solvent of acetonitrile and ethyl acetate, and then ethyl acetate may be further added.

In order to completely dissolve the compound (I) in the "solvent containing acetonitrile" in Step C-1, the solution of the compound (I) may be warmed, as required. For example, the compound (I) may be suspended in a mixed solvent of acetonitrile and ethyl acetate, and then the suspension rimy be warmed to completely dissolve the compound (I).

Although the volume of the "solvent containing acetonitrile" used in Step C-1 is not particularly limited so long as the compound (I) can be dissolved, the solvent can be used in a volume (L) of, for example, 2 to 10 times of the crystalline form of the compound (I) (kg) used as the raw material. The volume (L) of the solvent, is preferably 3 to 8 times, more preferably 4 to 5 times, of the crystalline form (kg) of the compound (I).

Step C-2 is a step of mixing the solution of the compound (I) and a poor solvent containing at least one of the solvents selected from ethyl acetate and methyl t-butyl ether to prepare a suspension of the compound (I), and stirring the suspension for at least 1 hour.

The starting point and the end point of the mixing time of Step C-2 are the same as the starting point and the end point of the mixing time mentioned for the afore-mentioned Step C.

In one embodiment of the resent invention, Step C-2 may be:

Step C-2 (a): the step of adding a poor solvent containing at least one of the solvents selected from ethyl acetate and methyl t-butyl ether to the solution of the compound (I) to prepare a suspension of the compound (I), and stirring the suspension for at least 1 hour, or Step C-2 (b): the step of adding the solution of the compound (I) to a poor solvent containing at least one of the solvents selected from ethyl acetate and methyl t-butyl ether to prepare a suspension of the compound (I), and stirring the suspension for at least 1 hour.

The poor solvent used in Step C-2 (hereinafter, encompassing Step C-2 (a) and Step C-2 (b)) contains at least one of the solvents selected from ethyl acetate and methyl t-butyl ether. A solvent comprising any one of only ethyl acetate, a solvent consisting of only methyl t-butyl ether, a mixed solvent of ethyl acetate and methyl t-butyl ether, a mixed solvent of ethyl acetate or methyl t-butyl ether, and another solvent, and a mixed solvent of ethyl acetate, methyl t-butyl ether, and another solvent is preferred. More preferred poor solvent comprises any one of only ethyl acetate, only methyl t-butyl ether, and a mixed solvent of ethyl acetate and methyl t-butyl ether.

Although the volume of the poor solvent used in Step C-2 is not particularly limited, it can be used in a volume (L) of, for example, 1.0 to 2.5 times, preferably 1.0 to 2.0 times, more preferably 1.0 to 1.5 times, of the volume (L) of the solvent containing acetonitrile, added in Step C-1.

Step C-2 is preferably Step C-2 (a). That is, by adding the poor solvent to the solution of the compound (I), the both are mixed. In this case, the poor solvent is preferably added stepwise or dropwise. For example, after the poor solvent is added dropwise in a volume of 0.1 to 0.25 time of the volume of the solvent containing acetonitrile added in Step C-1, the remaining poor solvent may be additionally added. When the poor solvent is added dropwise, it is preferable to add the solvent dropwise over a certain time of period or longer. When the poor solvent is added dropwise, although the dropping time is not particularly limited, it is preferably not less than 30 minutes, more preferably not less than 1 hour, still more preferably not less than 3 hours, further preferably not less than 4 hours and not more than 72 hours. In this case, the poor solvent may be added after the solution of the compound (I) is warmed. The solution may be gradually cooled after the poor solvent is added, as required.

Step L) is a step of filtering the suspension of the compound (I) prepared in Step C to obtain a crystalline form of the compound (I).

The crystalline form of the compound (I), for example Form B, obtained after Step D contains Form CO.

In one embodiment of the present invention, a content ratio of the compound (I-a) and the compound (I-b) in the compound (I) of the present invention obtained after Step C and Step D is 99:1 to 1:99.

In another embodiment of the present invention, a content ratio of the compound (I-a) and the compound (I-b) in the compound (I) of the present invention obtained after Step C and Step D is 90:10 to 10:90.

In another embodiment of the present invention, a content ratio of the compound (I-a) and the compound (I-b) in the compound (I) of the present invention obtained after Step C and Step D is 50:50 to 10:90.

In another embodiment of the present invention, a content ratio of the compound (I-a) and the compound (I-b) in the compound (I) of the present invention obtained after Step C and Step D is 40:60 to 20:80.

In another embodiment of the present invention, a content ratio of the compound (I-a) and the compound (I-b) in the compound (I) of the present invention obtained after Step C and Step D is 40:60 to 25:75.

In another embodiment of the present invention, a content ratio of the compound (I-a) and the compound (I-b) in the compound (I) of the present invention obtained after Step C and Step L) is 40:60 to 30:70.

Hereafter, the details of the method for preparing sofpironium bromide according to another embodiment of the present invention are explained for each of the steps described in [8], and the like, mentioned above. By using the preparation method of the present invention, the crystalline form of the present invention (for example, Form B) can be obtained with high purity via a crystalline form of sofpironium bromide (for example, Form A). This preparation method can be applied in an industrial scale.

In another embodiment of the present invention, the preparation method of the present invention comprises:

Step A: the step of reacting the compound (H) represented by the formula (II):

[Chem. 20]

(II)

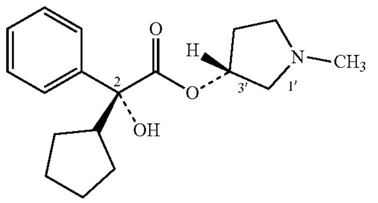

(2R, 3'R)

with ethyl bromoacetate in a solvent to prepare a reaction mixture containing the compound (I), Step B: the step of filtering the aforementioned reaction mixture to obtain a crystalline form of the compound (I), Step C': the step of preparing a suspension of the aforementioned crystalline form of the compound (I) in a solvent containing at least one of the solvents selected from ethyl acetate and methyl t-butyl ether, and stirring the suspension for at least 1 hour, and Step D: the step of filtering the aforementioned suspension of the compound (I) to obtain a crystalline form of the compound (I).

The compound (I) can be prepared by reacting the compound (II) and ethyl bromoacetate. However, the preparation methods described in Non-patent document 1, and the like, cannot be applied to industrial preparation as described above, since only acetonitrile is used as the solvent.

By using the suitable solvent in Step A, sofpironium bromide produced can be precipitated as the crystalline form in the reaction mixture. Therefore, only by filtering the reaction mixture in the following Step B, a crystalline form of sofpironium bromide can be obtained, and therefore the preparation method of the present invention is industrially preferred.

When "Step A" is simply described in the specification, a step according Step A or a step similar to Step A is also included, for example, Step A' and so on are included. Hereinafter, similarly, Step C includes Step C' and the like.

The "solvent" used in Step A is not particularly limited as long as the resulting sofpironium bromide can be precipitated as a crystalline form in the reaction mixture.

A preferred solvent used in Step A is a solvent comprising ethyl acetate and a more preferred solvent is a solvent solely comprising ethyl acetate.

Although the volume of the solvent used in Step A is not particularly limited so long as the reaction advances, it is preferably a volume (L) of 3 to 40 times, more preferably a volume (L) of 5 to 20 times (L), further preferably a volume (L) of 8 to 16 times (L), still further preferably a volume (L) of 11 to 13 times (L), of the weight (kg) of the compound (II).

The reaction temperature of Step A is not particularly limited so long as the reaction advances. For example, the reaction temperature of Step A may be room temperature to not higher than 80° C. According to one embodiment of the present invention, the reaction temperature of Step A is preferably not lower than 50° C. and not higher than 60° C.

Although the reaction time of Step A is not particularly limited, so long as the reaction advances, it is preferably 0.5 to 72 hours, more preferably 1 to 24 hours.

Although the equivalent amount of ethyl bromoacetate used in Step A is not particularly limited so long as the reaction advances, it is preferably 1.0 to 30 equivalents, more preferably 1.0 to 5.0 equivalents, further preferably 1.0 to 2.0 equivalents, still further preferably 1.0 to 1.5 equivalents, particularly preferably, 1.0 to 1.1 equivalents, based on the compound (II).

In one embodiment of Step A, an ethyl bromoacetate solution dissolving ethyl bromoacetate in any solvent in advance may be used. For example, an ethyl acetate solution of ethyl bromoacetate may be added into a solution of compound (II) to be prepared separately. A volume of solvent, reaction temperature, reaction time, and equivalent of ethyl bromoacetate are not particularly limited as long as a reaction can be proceeded. Preferably, the above values are applied.

After Step A, and before performing Step B, the reaction mixture may be warmed or cooled to precipitate a crystalline form of sofpironium bromide. For example, the reaction mixture may be warmed to not lower than 40° C. and not higher than 80° C., stirred for a certain period of time, and then gradually cooled to room temperature. Although the time for cooling is not particularly limited so long as the high-purity crystalline form can be obtained at a high yield, it is preferable to gradually cool the reaction mixture to room temperature over, for example, 1 hour or longer.

Step B is to filter the reaction mixture obtained in Step A to obtain a crystalline form of the compound (I). An example of the crystalline form of the compound (I) obtained by Step B includes Form A, but the crystalline form is not limited to this particular form. The crystalline form of the compound (I) obtained after successive Step A and Step B has high purity.

In one embodiment of the present invention, a content ratio of the compound (I-a) and the compound (I-b) in the compound (I) of the present invention obtained after Step A and Step B is 99:1 to 1:99.

In another embodiment of the present invention, a content ratio of the compound (I-a) and the compound I-b) in the compound (I) of the present invention obtained after Step A and Step B is 90:10 to 10:90.

In another embodiment of the present invention, a content ratio of the compound (I-a) and the compound (I-b) in the compound (I) of the present invention obtained after Step A and Step B is 50:50 to 10:90.

In another embodiment of the present invention, a content ratio of the compound (I-a) and the compound (I-b) in the compound (I) of the present invention obtained after Step A and Step B is 40:60 to 20:80.

In another embodiment of the present invention, a content ratio of the compound (I-a) and the compound (I-b) in the compound (I) of the present invention obtained after Step A and Step B is 40:60 to 25:75.

In another embodiment of the present invention, a content ratio of the compound (I-a) and the compound (I-b) in the compound (I) of the present invention obtained after Step A and Step B is 40:60 to 30:70.

Form A is a mixture of crystals of Form MN and Form MJ, and may cause crystal transition. Therefore, it is desirable to obtain a crystalline form having a more suitable profile for a drug substance of medicaments (for example, Form B).

In another embodiment of the present invention, a crystalline form of sofpironium bromide having a more suitable profile for a drug substance of medicaments (for example, Form B) is obtained by Step A and Step B, and the following Step C' and Step D.

The definitions of the terms used for Step C' of the preparation method of the present invention described in [8], and the like, are the same as those of Step C described in [7].

The definitions of the terms used for Step D of the preparation method of the present invention described in [8], and the like, are the same as those of Step D described in [7].

Hereafter, purity and impurities of the compound (I) of the present invention are explained.

The compound (I) of the present invention (including the crystalline form of the present invention) contains extremely little impurities, and shows high purity, and therefore it has quality suitable for a drug substance of medicaments.

In the specification, the term "impurities" is a generic term for referring to substances other than the chemical substances defined as drug substance or pharmaceutical additives among the substances contained in the drug substance or pharmaceutical preparation, and encompasses analogous substances, reaction products, decomposition products, and the like.

In the specification, the term "compound (I) of the present invention" refers to the high-purity compound (I) obtained by the aforementioned methods for preparing a crystalline form of the present invention (for example, those of [8a] and [8b]), and encompasses the crystalline form of the present invention.

In the specification, the term "high-purity compound (I)" refers to the compound (I) of which purity is not less than 98.0 w/w %. For example, according to one embodiment of the present invention, the "high-purity compound (I)" is the compound (I) of which purity is not less than 99.0 w/w %, and according to another embodiment of the present invention, the "high-purity compound (I)" is the compound (I) of which purity is not less than 99.5 w/w %.

Content of each impurity contained in the compound (I) of the present invention is not more than 0.5 w/w %, preferably not more than 0.15 w/w %, based on the content of the compound (I). Therefore, content of each impurity contained in the pharmaceutical composition using the compound (I) of the present invention is not more than 0.5 w/w %, preferably not more than 0.15 w/w %, based on the content of the compound (I).

The total content of the impurities contained in the compound (I) of the present invention is not more than 4.0 w/w %, preferably not more than 2.0 w/w %, more preferably not more than 1.0 w/w %, based on the content of the compound (I). Therefore, the total content of the impurities contained in the pharmaceutical composition using the compound (I) of the present invention is not more than 4.0 w/w %, preferably not more than 2.0 w/w %, more preferably not more than 1.0 w/w %, based on the content of the compound (I).

In the specification, the "impurities" encompass the following compounds, but are not limited to these examples.

1) The compound (III) represented by the following formula (III):

[Chem. 21]

(III)

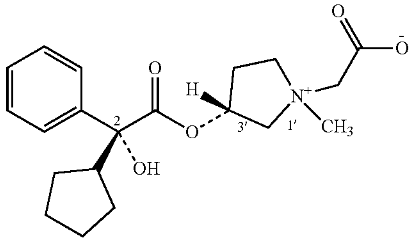

(2R, 3'R)

The compound (III) is identified as the compound produced by hydrolysis of the ethyl ester of the compound (I), and comprises a mixture of epimers for the 1'-position.

The content of the compound (III) contained in the compound (I) of the present invention is not more than 0.5 w/w %, preferably not more than 0.15 w/w %. Therefore, the content of the compound (III) contained in the pharmaceutical composition using the compound (I) of the present invention is not more than 0.5 w/w %, preferably not more than 0.15 w/w %, based on the content of the compound (I).

2) The compound (IV) represented by the following formula (IV):

[Chem. 22]

(IV)

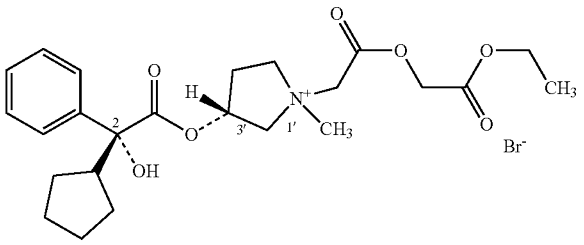

(2R, 3'R)

The compound (IV) may be produced when ethyl bromoacetate used in the aforementioned Step A contains bromoacetic acid as an impurity.

The content of the compound (IV) contained in the compound (I) of the present invention is not more than 0.5 w/w %, preferably not more than 0.15 w/w %. Therefore, the content of the compound (IV) contained in the pharmaceutical composition using the compound (I) of the present invention is not more than 0.5 w/w %, preferably not more than 0.15 w/w %, based on the content of the compound (I).

3) The compound (V) represented by the following formula (V):

[Chem. 23]

(V)

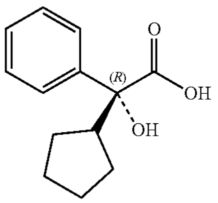

The compound (V) is identified as the compound produced by hydrolysis of the cyclopentylmandelic acid ester of the compound (I).

The content of the compound (V) contained in the compound (I) of the present invention is not more than 0.5 w/w %, preferably not more than 0.15 w/w %. Therefore, the content of the compound (V) contained in the pharmaceutical composition using the compound (I) of the present invention is not more than 0.5 w/w %, preferably not more than 0.15 w/w %, based on the content of the compound (I).

The total content of the compounds (III), (IV), and (V) contained in the compound (I) of the present invention is not more than 4.0 w/w %, preferably not more than 2.0 w/w %, more preferably not more than 1.0 w/w %. Therefore, the total content of the compounds (III), (IV), and (V) contained in the pharmaceutical composition using the compound (I) of the present invention is not more than 4.0 w/w %, preferably not more than 2.0 w/w %, more preferably not more than 1.0 w/w %, based on the content of the compound (I).

The compound (I) of the present invention described above (that is, the high-purity compound (I)) can be prepared by the preparation method comprising Step A and Step B as described in [8a]. Further, as described in [8b], Step C' and Step D may be performed after Step A and Step B.

The compounds (III), (IV), and (V), which are the impurities mentioned above, are useful as an index in the preparation of the high-purity compound (I) (including the crystalline form of the compound (I) of the present invention).

The present invention encompasses a pharmaceutical composition using the compound (I) of the present invention (including the crystalline form of the present invention) as an active ingredient (henceforth also referred to as the pharmaceutical composition of the present invention). The pharmaceutical composition of the present invention is preferably, but not particularly limited to, a topical application composition.

When the pharmaceutical composition of the present invention is a topical application composition, it can be prepared in a conventional manner, for example, according to the compositions described in Patent document 1.

The pharmaceutical composition of the present invention is preferably, but not particularly limited to, a medicament used for treatment of hyperhidrosis, more preferably a medicament used for treatment of primary axillary hyperhidrosis or primary palm hyperhidrosis. However, since the compound (I) has an anticholinergic action, the pharmaceutical composition of the present invention can be used as a medicament for treatment of various diseases relating to an action of acetylcholine.

EXAMPLES

Hereinafter, the present invention is more specifically explained with reference to examples. However, the present invention is not limited by these examples.

The chemical shift values in the solid-state $^{13}C$ nuclear magnetic resonance spectra, characteristic diffraction angles observed in powder X-ray diffractometry, characteristic endothermic peaks observed in DSC, and characteristic absorption bands observed in IR for the crystalline forms mentioned in the specification may vary depending on the measurement conditions. Therefore, the measured values for the crystalline forms mentioned in the specification may contain errors.

Preparation Example 1 <Method for Preparing Crude (R)-Cyclopentylmandelic Acid (Compound (V), (R)-CPMA)>

DL-Cyclopentylmandelic acid (CPMA, 66.0 g, 0.30 mot) was dissolved in acetonitrile (1300 mL) at 50° C. L-Tyrosine methyl ester (70.2 g, 0.36 mol) was added. The entrance slot of the reaction vessel was washed down with acetonitrile (66 mL), the reaction mixture was stirred under reflux, and further stirred with gradual cooling to room temperature, and then the precipitates were collected by filtration. After the filtration residue was washed with acetonitrile, the filtrate and the wash liquid were combined and concentrated, and water (292 mL) was added to the residue for dissolution. After the resulting aqueous solution was cooled with water, dilute sulfuric acid was added to the solution until it became around pH 1, and then the mixture was extracted with methyl t-butyl ether. The organic layer was dried over magnesium sulfate. Magnesium sulfate was removed by filtration, then the solvent was evaporated, and the resulting solid was dried to obtain crude (R)-CPMA (32.3 g, 49% yield, 96.8% c.c.) as a pale yellow solid.

Optical purity of crude (R)-CPMA was measured by high performance liquid chromatography (HPLC) under following conditions.

<Measurement of Optical Purity of (R)-CPMA>

1) Analysis Conditions

Detector: Ultraviolet absorptiometer (measurement wavelength: 220 nm)

Column: AD-RH (internal diameter: 4.6 mm, length: 15 cm, particle diameter: 5.0 μm)

Column temperature: Constant temperature around 30° C.

Flow rate: 0.9 mL/min

Injection volume: 10 μL

Eluent: water:acetonitrile:formic acid=600:400:1

2) Preparation of Sample Solution

Each sample was weighed in an amount of about 10 mg, and 10 mL acetonitrile was added to prepare a sample solution.

Preparation Example 2 <Method for Preparing (R)-cyclopentylmandelic Acid (Compound (V), (R)-CPMA)>

The crude (R)-CPMA (31.9 g, 145 mmol) prepared in Preparation Example 1 was suspended in toluene (140 mL), and (R)-phenylethylamine (20.7 g, 171 mmol) was added. The reaction mixture was stirred under reflux, and then n-heptane (1.40 mL) was added to the reaction mixture. The reaction mixture was stirred under reflux. The reaction mixture was stirred with gradual cooling to room temperature, and then the precipitates were collected by filtration. The precipitates were washed with n-heptane, and then dried. The dried precipitates were suspended in a mixture of toluene (127 mL) and n-heptane (127 mL). The suspension was dissolved under reflux, and then the solution was stirred with gradual cooling to room temperature. The precipitates were collected by filtration, washed with n-heptane, and then dried. Methyl t-butyl ether (171 mL) and water (79 mL) were added to the dried precipitates, the mixture was stirred, and dilute sulfuric acid was added until the solid was dissolved. The resulting solution was stirred, then the organic layer was separated, and the aqueous layer was extracted with methyl t-butyl ether. The organic layers were combined, and extracted with a sodium hydrogencarbonate solution. The aqueous layer was extracted with methyl t-butyl ether to wash, and then dilute sulfuric acid was added to the aqueous layer until it became acidic to obtain the suspension. The resulting suspension was extracted with methyl t-butyl ether, and the organic layer was washed with water, and then dried over magnesium sulfate. Magnesium sulfate was removed by filtration, then the solvent was evaporated, and the resulting solid was dried to obtain (R)-CPMA (22.7 g, 71% yield, >99.9% e.e.) as a pale yellow solid. The optical purity was measured by the same method as that of Preparation Example 1.

Preparation Example 3 <Method for Preparing (2R, 3'R)-3'-(2-cyclopentyl-2-hydroxy-2-phenylacetoxy)-1'-methylpyrrolidine (Compound (II), (2R,3'R)-CPMA-MP)>

(R)-CDMA (5.0 g, 2.3 mmol) prepared in Preparation Example 2 and 1,1'-carbonyldiimidazole (CDI, 4.8 g, 30 mmol) were mixed in toluene (60 mL) at 5° C., and then degassing and argon substitution were performed under reduced pressure. Sodium t-butoxide (0.4 g, 5 mmol) and (R)-1-methyl-3-pyrrolidinol ((R)-MP, 2.5 g, 25 mmol) were mixed in toluene (30 mL) in another vessel at room temperature. The resulting solution was warmed to 40° C., the reaction mixture of (R)-CPMA and CDI was added dropwise, and the resulting solution was stirred. The reaction mixture was stirred with gradual cooling to room temperature, then water was added, and the aqueous layer was removed. The organic layer was washed with water again, and dilute sulfuric acid was added to aqueous layer until it became pH 2, and the organic layer was removed. The resulting aqueous layer was washed with toluene, aqueous potassium carbonate was added to the aqueous layer until it became pH 9, and the mixture was extracted with ethyl acetate. The aqueous layer was extracted with ethyl acetate again, the organic layers were combined, washed with water, and then concentrated to obtain (2R,3'R)-CPMA-MP (6.4 g, 93% yield) as a colorless oil.

Preparation Example 4 <Method for Preparing Crystalline Form of Compound (I-a) (Form MN)>

The diastereomers of sofpironium bromide (about 900 mg) were fractionated by silica gel column chromatography using 2-ch parallel purification system Purif-Rp2. Two of Presep (registered trademark) (Luer Lock) Silica Gel (HC-N) Type L were connected, and an eluent shown in Table 1 was used.

TABLE 1

| Preparative separation conditions | | |
|---|---|---|
| Time (minute) | Dichloromethane (vol %) | Ethanol (vol %) |
| 0-35 | 90 | 10 |
| 35-45 | 90 → 86 | 10 → 14 |
| 45-55 | 86 | 14 |
| 55-60 | 86 → 80 | 14 → 20 |
| 60-80 | 80 | 20 |

The first peak was identified as the compound (I-a). The concentration product of the first peak fraction (g) was dissolved in 2-fold volume (mL) of acetonitrile at 40° C. 10-fold volume (mL) of a mixture of methyl t-butyl ether and ethyl acetate (3/2) was added to the solution, and the mixture was stirred to crystallize the compound (I-a). Further, 8-fold volume (mL) of a mixture of methyl t-butyl ether and ethyl acetate (3/2) was added to prepare a suspension. The suspension was stirred with gradual cooling to room temperature. The precipitates were collected by filtration, and washed twice with 2-fold volume (mL) of a mixture of methyl t-butyl ether and ethyl acetate (3/2). The resulting solid was dried to obtain a crystalline form of the compound (I-a) (Form MN) as a white solid (recovery rate 90%). The recovery rate is showed by dividing the weight of the solid of the resulting crystalline form with the weight of the concentration product of the fraction.

Preparation Example 5 <Method for Preparing Crystalline Form of Compound (I-b) (Form MJ)>

The second peak obtained in the preparative separation of Preparation Example 4 was identified as the compound (I-b). The concentration product of the second peak fraction (g) was dissolved in 2-fold volume of acetonitrile (mL) at 40° C., 10-fold volume (mL) of a mixture of methyl t-butyl ether and ethyl acetate (3/2) was added to the solution, and the mixture was stirred to crystallize the compound (I-b). Further, 8-fold volume (mL) of a mixture of methyl t-butyl ether and ethyl acetate (3/2) was added to prepare a suspension. The suspension was stirred for with gradual cooling to room temperature. The precipitates were collected by filtration, and washed twice with 2-fold volume (mL) of a mixture of methyl t-butyl ether and ethyl acetate (3/2). The resulting solid was dried to obtain a crystalline form of the compound (I-b) (Form MJ) as a white solid (recovery rate 88%). Definition of the recovery rate is the same as that of Preparation Example 4.

Preparation Example 6 <Study of Crystalline Forms by Crystallization Method 1, Using Sofpironium Bromide Having Various Content Ratios of Compound (I-a) And Compound (I-b)>

Sofpironium bromide (3.7 g) having a content ratio of the compound (I-a) and the compound (I-b) of 1:2, and the compound (I-a) (0.3 g) were suspended in a mixture of acetonitrile (11.6 mL) and ethyl acetate (6.6 mL), and the suspension was dissolved by heating. Ethyl acetate (11.0 mL) was added, the mixture was cooled to 40° C., and then methyl t-butyl ether (1.2 mL) and seed crystals (Form A, 2.0 mg) were added. Methyl t-butyl ether (25.2 mL) was added at once to the suspension, and the mixture was stirred at room temperature. After stirring at 5° C., the solid was collected by filtration, washed with ethyl acetate, and dried to obtain sofpironium bromide (3.8 g) having a content of the compound (I-b) of 60% (actual value of area percentage by HPLC: 58.9%) as a white solid.

By the same preparation method (crystallization method 1), sofpironium bromide having a content of the compound (I-b) of 80% (actual value of area percentage, by HPLC: 8(18%) was prepared (Preparation Example 6-2).

Preparation Example 7 <Study of Crystalline Forms, by Crystallization Method 2, Using Sofpironium Bromide Having Various Content Ratios of Compound (I-a) and Compound (I-b)>

Sofpironium bromide (3.7 g) having a content ratio of the compound (I-a) and the compound (I-b) of 1:2, and the compound (La) (0.3 g) were suspended in acetonitrile (11.6 mL) and ethyl acetate (6.6 mL), and the suspension was dissolved by heating. Ethyl acetate (11.0 mL) was added, the mixture was cooled to 40° C., then methyl t-butyl ether (1.2 mL) and seed crystals (Form A, 2.0 mg) were added, and the mixture was stirred. Methyl t-butyl ether (25.2 mL) was added dropwise over 5 hours, and the mixture was stirred at room temperature. After stirring at 5° C., the solid was collected by filtration, washed with ethyl acetate, and dried to obtain sofpironium bromide (3.2 g) having a content of the compound (I-b) of 60% (actual value of area percentage by HPLC: 59.3%) as a white solid.

Sofpironium bromides having contents of the compound (I-b) of 70%, 75%, and 80% were prepared in the same manner, respectively (Preparation Example 7-2: actual value of area percentage by HPLC 70.3%, Preparation Example 7-3: actual value of area percentage by HPLC 75.3%, Preparation Example 7-4: actual value of area percentage by HPLC 79.6%).

Example 1 <Method for Preparing Crystalline Form of Sofpironium Bromide (Form A)>

At room temperature, (2R,3'R)-CPMA-MP (2.7 g, 9 mmol) was dissolved in ethyl acetate (33 mL), ethyl bromoacetate (0.08 g, 0.5 mmol) was added, precipitation of sofpironium bromide was confirmed, bromoethyl acetate (1.5 g, 9 mmol) was further added, and then the mixture was stirred. Then, the reaction mixture was heated to 52° C., stirred, and gradually cooled to room temperature over, and then the solid was collected by filtration. The resulting solid was washed with ethyl acetate, and then dried to obtain a crystalline form of sofpironium bromide (Form A, 4.1 g, 86.6% yield) as a white solid.

Example 2 <Method for Preparing Crystalline Form of Sofpironium Bromide (Form B)>

At room temperature, sofpironium bromide of Form A (5.0 g, 11 mmol) was suspended in a mixture of acetonitrile (14.5 mL) and ethyl acetate (8.3 mL), and the suspension was heated to 50° C. to obtain a solution. Ethyl acetate (13.8 mL) was further added, and then methyl t-butyl ether (33.0 mL) was added dropwise to the resulting solution over 5 hours. The resulting suspension was stirred, gradually cooled to 5° C., and then further stirred. The resulting solid was collected by filtration, washed with ethyl acetate, and then dried to obtain a crystalline form of sofpironium bromide (Form B, 4.8 g, recovery rate 97%) as a white solid.

The crystalline form was confirmed as Forma B by powder X-ray diffraction spectrum.

Example 3 <Another Method for Preparing Crystalline Form of Sofpironium Bromide (Form B)>

At room temperature, sofpironium bromide of Form A (5.6 g, 12 mmol) was suspended in a mixture of acetonitrile (16.3 mL) and ethyl acetate (9.2 mL), and the suspension was heated to 50° C. to obtain a solution. Ethyl acetate (15.4 mL) was further added, the mixture was cooled to 40° C., and then methyl t-butyl ether (1.7 mL) and sofpironium bromide of Form B (2.8 mg, 0.006 mmol) as seed crystals were added to the resulting solution, precipitation of a crystalline form of sofpironium bromide was confirmed, and then methyl t-butyl ether (35.3 mL) was added dropwise over 5 hours, and the mixture was stirred with gradual cooling to room temperature. The reaction mixture was cooled to 5° C., and further stirred, and then the resulting solid was collected by filtration, washed with ethyl acetate, and then dried to obtain a crystalline form of sofpironium bromide (Form B, 5.4 g, recovery rate 96%) as a white solid.

The crystalline form was confirmed as Form B by powder X-ray diffraction spectrum and other spectra.

Example 4 <Another Method for Preparing Crystalline Form of Sofpironium Bromide (Form B)>

Ethyl bromoacetate (92 kg) and ethyl acetate (29 kg) were mixed to obtain an ethyl bromoacetate solution. Separately, (2R,3'R)-CPMA-MP (159 kg) was dissolved in ethyl acetate (1722 kg), then a bromoacetate solution (6 kg) was added, and the precipitation of sofpironium bromide was confirmed. The ethyl bromoacetate solution (115 kg) was further added and stirred. Thereafter, the mixture was heated to 50° C. with stirring, cooled slowly to room temperature, and then the solid was collected by filtration. The resulting solid was washed with ethylacetate and dried to give the crystalline form of sofpironium bromide (222 kg) as a white solid.

The obtained sofpironium bromide (222 kg) was suspended in a mixed solution of acetonitrile (443 kg) and ethyl acetate (290 kg) at room temperature, heated to 55° C., and then activated carbon (7 kg) was added and stirred. After removing the solid by filtration, the solid was washed with a mixture of acetonitrile (61 kg) and ethyl acetate (40 kg). The washings and filtrates were combined, ethyl acetate (550 kg) was added, cooled to 40° C., and then methyl t-butyl ether (49 kg) and Form B of sofpironium bromide as seeds (1.1 kg) were added to the resulting solution.

After the resulting suspension was warmed to 50° C., methyl t-butyl ether (1035 kg) was added dropwise over 5 hours, and the resulting suspension was stirred with slow cooling to 5° C. Acetonitrile (17 kg), ethyl acetate (32 kg) and methyl tert-butyl ether (39 kg) were added to the suspension, and the solid was collected by filtration. The resulting solid was washed with ethyl acetate and dried to give the crystalline form of sofpironium bromide (Form B, yield: 200 kg, 2-step yield: 90.1%) as a white solid.

The crystalline form was confirmed as Form B by powder X-ray diffraction spectrum.

Example 5 <Another Method for Preparing Crystalline Form of Sofpironium Bromide (Form B)>

Step 1: Resolution of α-Cyclopentylmandelic Acid

α-Cyclopentylmandelic acid (22.8 kg, 103.5 mol) was dissolved in acetonitrile at 80° C., L-Tyrosine methyl ester (22.2 kg) was added to the solution, and the mixture was heated at reflux for 70 minutes. The mixture was cooled to room temperature, and the precipitated solid (salt of (S)-α-cyclopentylmandelic acid with L-tyrosine methyl ester) was collected and discarded. The mother liquor was concentrated under reduced pressure to about 46 L and the salt of (R)-α-cyclopentylmandelic acid and L-tyrosine methyl ester precipitated as a thick slurry. The slurry was then diluted with water, concentrated HCl and extracted with ethyl acetate. The organic solution was washed with brine and solvent swapped into heptane at 75° C. After seeding and cooling to 0° C., the solid was collected by filtration. Finally, heptane washing and drying of the filter cake gave 8.5 kg, 37% yield, of the desired (R)-α-cyclopentylmandelic acid as an off-white solid.

Step 2: Mitsunobu Reaction and N-Alkylation

To a stirred solution of (R)-α-cyclopentylmandelic acid (8.5 kg, 38.6 mol), triphenylphosphine (10.1 kg), and (S)-1-methyl-3-pyrrolidinol (3.7 kg) in anhydrous 2-methyltetrahydrofuran (2-Me THF) were added with Diisopropyl Azodicarboxylate (DIAD) (7.8 kg) at 5° C. over 1-1.5 hour. After stirring at ambient temperature for 1 hour, the mixture was diluted with methyl t-butyl ether (MTBE) and cooled to 0° C. to afford a precipitate of triphenylphosphoine oxide which was subsequently filtered. The product containing filtrate was solvent swapped into acetonitrile (40 kg, about 50.9 L) and stirred at 20° C. for 4 hours with ethyl bromoacetate (9.7 kg) to provide a crude BBI-4000 solution. This solution was treated with Cuno carbon cartridges and MTBE was added into the carbon-treated Sofpironium bromide solution with seeding to provide 13.95 kg (77% yield) of Sofpironium bromide solid after filtration and drying.

Sofpironium bromide (13.9 kg) was dissolved in acetonitrile (33.4 kg, about 42.5 L) at 60° C. and cooled to 30° C. The clear solution was treated with Cuno carbon cartridges; polish filtered, and stirred for 7 hours with MTBE (80 kg, about 108 L) with seeding. The precipitated solid was collected by filtration and rinsed with mixed solvent of acetonitrile (7 kg, about 8.91 L) and MTBE (25 kg, about 33.7 L), dried under vacuum to yield 11.6 kg of white solid (mp 144-146° C., purity 99.8% by HPLC). The crystalline form was confirmed as Form B by powder X-ray diffraction spectrum.

Example 6 <Method for Preparing Crystalline Form of Compound (I) (Form CO)>

The compound (I-a) (50 mg) and the compound (I-b) (150 mg) obtained in Preparation Example 4 and 5 were combined, and suspended in a mixture of acetonitrile (0.58 mL), ethyl acetate (0.88 mL), and methyl t-butyl ether (0.06 mL), and then heated to 50° C. The aforementioned suspension was stirred at 50° C. for 15 hours, and then stirred with gradual cooling to room temperature. The resulting precipitates were collected by filtration, washed twice with ethyl acetate (2 mL), and then dried to obtain a crystalline form of the compound (I) (Form CO, 121 mg, recovery rate 61%) as a white solid. The obtained compound (I) contains compound (Ia) and compound (Ib) at a ratio of 1:3.

The crystalline form was confirmed as Form CO by powder X-ray diffraction spectrum and other spectra.

Reference Example 1 <Method for Preparing Intramolecular Salt of (2R,3'R)-3'-(2-cyclopentyl-2-hydroxy-2-phenylacetyl)-1'-methyl-1'-carboxymethylpyrrolidinium (compound (III))>

[Chem. 24]

(III)

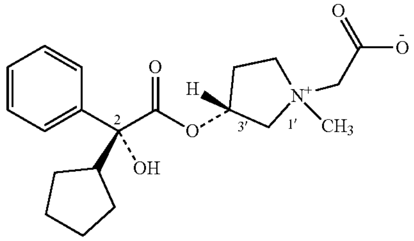

(2R, 3'R)

Sofpironium bromide (15 g, 3.2 mmol) was dissolved in aqueous sodium hydroxide (0.1 mol/L, 318 mL), and the solution was stirred at room temperature for 3.5 hours. The resulting solution was lyophilized, and then the residue was extracted with dichloromethane. The resulting dichloromethane solution was concentrated, and then the residue was purified by silica gel column chromatography (eluent: dichloromethane/methanol=90/10) to obtain the compound (III) (5.4 g, 47% yield) as a white solid.

Reference Example 2 <Method for Preparing (2R,3'R)-3'-(2-cyclopentyl-2-hydroxy-2-phenylacetyl)-1'-methyl-1'-ethoxycarbonylmethoxycarbonylmethylpyrrolidinium Bromide (Compound (IV))>

[Chem. 25]

(IV)

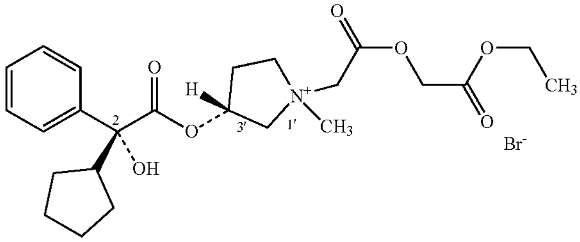

(2R, 3'R)

(2R,3'R)-CPMA-MP (4.3 g, 14 mol) was dissolved in ethyl acetate (50 mL), and 2-ethoxy-2-oxyethyl 2-bromoacetate (3.7 g, 16.4 mmol) was added at room temperature. The reaction mixture was stirred for 16 hours, and concentrated. The residue was purified by silica gel column chromatography (mobile phase: dichloromethane/ethanol) to obtain a viscous white solid as a crude product of the compound (IV) (6.3 g). The resulting crude product of the compound (IV) was dissolved in acetonitrile (10 mL), ethyl acetate (15 mL) was added, and the mixture was heated to 50° C. The reaction mixture was cooled to 40° C., and methyl t-butyl ether (100 mL) was added to obtain a suspension. The suspension was gradually cooled to room temperature, and then the resulting precipitates were collected by filtration, washed with methyl t-butyl ether, and then dried at 50° C. for 5 hours under reduced pressure to obtain the compound (IV) (5.8 g, 78% yield for 2 steps) as a white solid.

$^1$H-NMR (400 MHz, $CDCl_3$) δ: 1.25-1.73 (9H, m), 2.11-2.27 (1H, m), 2.43 (2H, s), 2.80-3.08 (2H, m), 3.15 (1H, s), 3.69 (2H, s), 3.91-4.02 (1H, m), 4.12-4.56 (6H, m), 4.65-4.77 (2H, m), 4.77-4.96 (1.33H, m), 5.28-5.45 (0.67H, m), 5.52-5.61 (1H, m), 7.20-7.30 (1H, m), 7.30-7.39 (2H, m), 7.54-7.62 (2H, m)

Test Example 1-1 <Powder X-Ray Diffractometry of Crystalline Forms of Sofpironium Bromide Prepared by Crystallization Method 1>

Sofpironium bromide is a mixture of diastereomers (compound (I-a) and compound (I-b)), but it was unknown how the content ratio thereof influences the characteristics and physicochemical properties of a crystalline form of the mixture.

Therefore, each diastereomer and various sofpironium bromides having different content ratio of the compound (I-a) and the compound (I-b) (sofpironium bromides having contents of the compound (I-b) of 60%, 70%, 75%, or 80%) were subjected to recrystallization using a mixed solvent of acetonitrile, ethyl acetate, and methyl t-butyl ether (crystallization method 1 or crystallization method 2), and then to various instrumental analyses.

In Test Example 1-1, powder X-ray diffraction of each crystalline form obtained in Preparation Example 4 (Form MN), Preparation Example 5 (Form MJ), Preparation Example 6, and Preparation Example 6-2 mentioned above was measured, according to the following method. Diffraction angle 2θ values of the same crystalline forms usually correspond with each other with a margin of ±0.2° or ±0.1°.

Each sample (0.1 g) was filled on a glass sample plate. This sample plate was attached to a standard sample holder, and the diffraction pattern was determined under the following conditions with a powder X-ray diffractometer (RINT2200 Ultima II/PC, Rigaku Corporation). Separately, a silicon powder diffraction standard reference material was analyzed.

TABLE 2

| Item | Measurement conditions |
|---|---|
| Anticathode | Copper |
| Tube current of X-ray tube | 40 mA |
| Tube voltage of X-ray tube | 40 kV |
| Scanning speed | 2°/min |
| Time constant | 0.5 second |

FIG. 1 shows the diffraction pattern of the crystalline form (Form MN) of the compound (I-a). The characteristic diffraction angles are shown in the following table.

TABLE 3

| 2θ |
|---|
| 7.1 |
| 16.9 |
| 21.4 |
| 22.3 |
| 23.0 |
| 24.5 |

Figure 2:
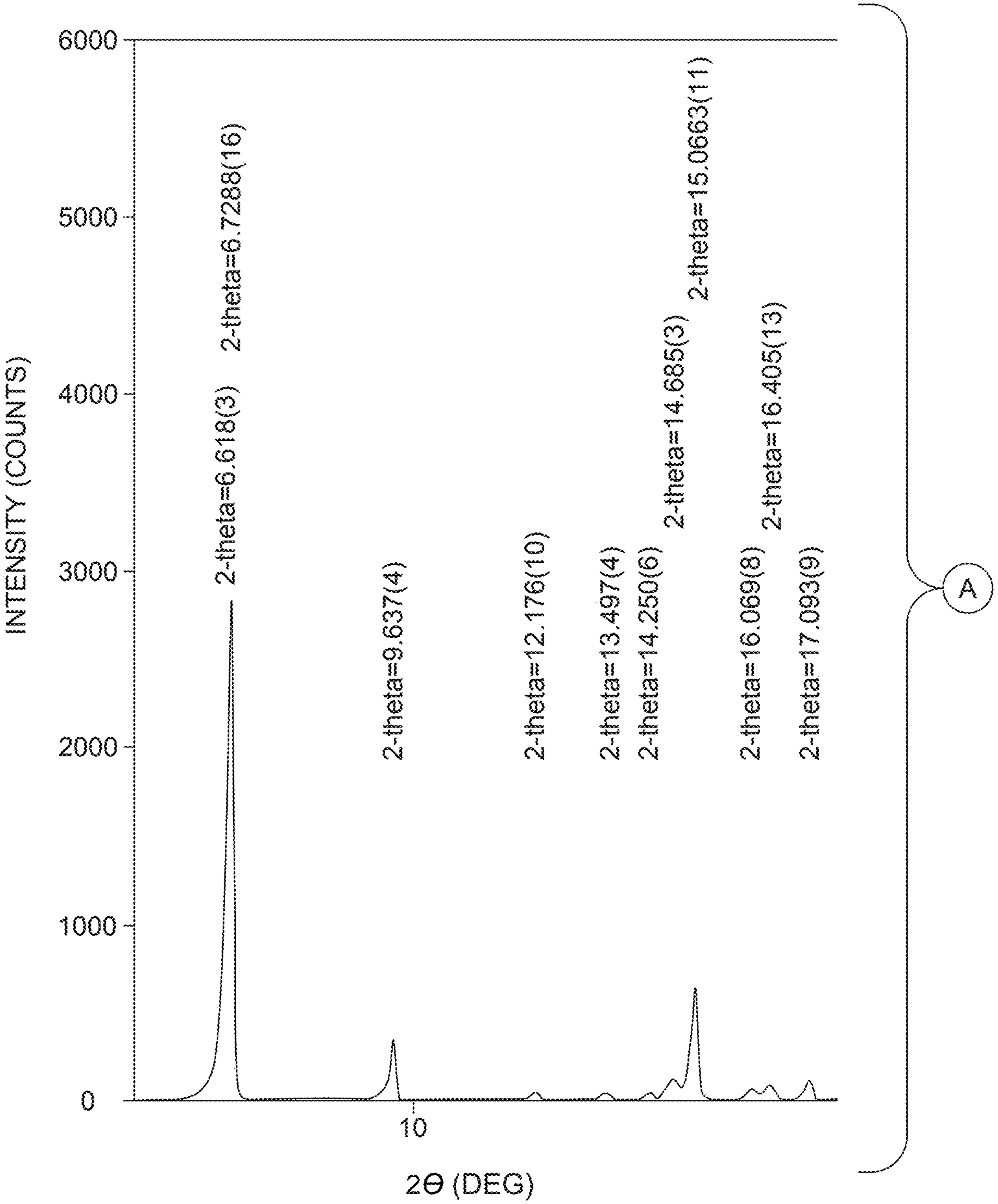
FIG. 2 Powder X-ray diffraction spectrum of the crystalline form (Form MJ) of the compound (I-b) prepared in Preparation Example 5.

FIG. 2 shows the diffraction pattern of the crystalline form (Form MJ) of the compound (I-b). The characteristic diffraction angles are shown in the following table.

TABLE 4

| 2θ |
|---|
| 6.7 |
| 9.6 |
| 15.1 |
| 19.2 |
| 20.1 |
| 21.7 |

High intensities were observed for Form MN at the peak of diffraction angle 2θ of 7.1° and for Form MJ at the peak of diffraction angle 20 of 6.7°, and those peaks were characteristic for each crystalline form. Therefore, it became clear that observation of peaks at 2θ=7.1±0.1° and 2θ=6.7±0.1° in various crystalline forms of sofpironium bromide enables confirmation of the presence of Form MN and Form MJ.

The characteristic peaks of each crystalline form determined in Test Example 1-1 mentioned above are shown in Table 5.

TABLE 5

| Preparation Example | Contentratio of compound (I-a) (%) | Contentratio of compound (I-b) (%) | Characteristic diffraction angle (2θ)* 6.7 ± 0.1° | 7.1 ± 0.1° |
|---|---|---|---|---|
| Preparation Example 4 (Form MN) | 100 | 0 | | Observed |
| Preparation Example 6 | 40 | 60 | Observed | Observed |
| Preparation Example 6-2 | 20 | 80 | Observed | Observed |
| Preparation Example 5 (Form MJ) | 0 | 100 | Observed | |

*"Observed" means that a peak was observed at the corresponding diffraction angle. The blank means that the peak was not clearly observed.

For both of the sofpironium bromides having the contents ratio of the compound (I-b) of 60% and 80%, the peak at the diffraction angle 2θ=7.1±0.1° characteristic to Form MN and the peak at the diffraction angle 2θ=6.7±0.1° characteristic to Form MJ were observed. For the intensities of the peaks relatively changed depending on the ratio of the diastereomers, it is considered that the sofpironium bromides prepared by the aforementioned crystallization method 1 (Preparation Example 6 and Preparation Example 6-2) comprise a mixture of Form MN and Form MJ.

Test Example 1-2 <Powder X-Ray Diffractometry of Crystalline Forms of Sofpironium Bromide Prepared by Crystallization Method 2>

In Test Example 1-2, powder X-ray diffraction was measured, similar to the method described in Test Example 1-1 for each of the crystalline forms obtained in Preparation Example 4 (Form MN). Preparation Example 5 (Form MJ), Preparation Example 7, Preparation Example 7-2, Preparation Example 7-3, and Preparation Example 7-4 mentioned above. The characteristic peaks observed in each measurement are shown in Table 6.

TABLE 6

| Preparation Example | Content ratio of compound (I-a) (%) | Content ratio of compound (I-b) (%) | Characteristic diffraction angle (2θ)* 5.9 ± 0.1° | 7.1 ± 0.1° | 7.6 ± 0.1° |
|---|---|---|---|---|---|
| Preparation Example 4 (Form MN) | 100 | 0 | | Observed | |
| Preparation Example 7 | 40 | 60 | Observed | Observed | Observed |
| Preparation Example 7-2 | 30 | 70 | Observed | Observed | Observed |
| Preparation Example 7-3 | 25 | 75 | Observed | | Observed |

*"Observed" means that a peak was observed at the corresponding diffraction angle. The blank means that the peak was not clearly observed.

For the sofpironium bromides of Preparation Example 7 and Preparation Example 7-2, the peak at the diffraction angle 2θ=7.1±0.1° characteristic to the crystalline form of the compound (I-a) (Form MN) was confirmed. The peak at 2θ=7.1±0.1° was identified as a peak characteristic to Form MN, the sofpironium bromides of Preparation Example 7 and Preparation Example 7-2 contained Form MN. Further, for the sofpironium bromides of Preparation Example 7 and Preparation Example 7-2, the peak at 2θ=5.9±0.1° and the peak at 2θ=7.6±0.1° were also observed. These peaks are not detected with strong intensity for Form MN and Form MJ. Therefore, it is considered that the sofpironium bromides of Preparation Example 7 and Preparation Example 7-2 contained a crystalline form other than Form MN and Form MJ.

The peak characterizing Form MN (2θ=7.1±0.1°) and the peak characterizing Form MJ (2θ=6.7±0.1°) were not observed for the sofpironium bromide of Preparation Example 7-3 (content of the compound (I-b) was 75%), whilst the peaks at 2θ=5.8±0.1° and 2θ=7.6±0.1° were observed. On the basis of these results, it is considered that the sofpironium bromide of Preparation Example 7-3 comprised a novel crystalline form of sofpironium bromide, and it is a novel cocrystal (Form CO) having a content ratio of the compound (I-a) and the compound (I-b) of 1:3.

For the sofpironium bromide of Preparation Example 7-4 (content ratio of the compound (I-b) was 80%), the peak of Form CO and the peak considered to be derived from a crystalline form of the compound (I-b) were observed, whereas the peak characterizing Form MN (2θ=7.1±0.1°) was not observed (data are not shown in the table).

Then, a powder X-ray diffraction pattern of the crystalline form of sofpironium bromide prepared in Example 6, and the crystalline form of sofpironium bromide prepared in Preparation Example 7-3 were compared.

Figure 3:
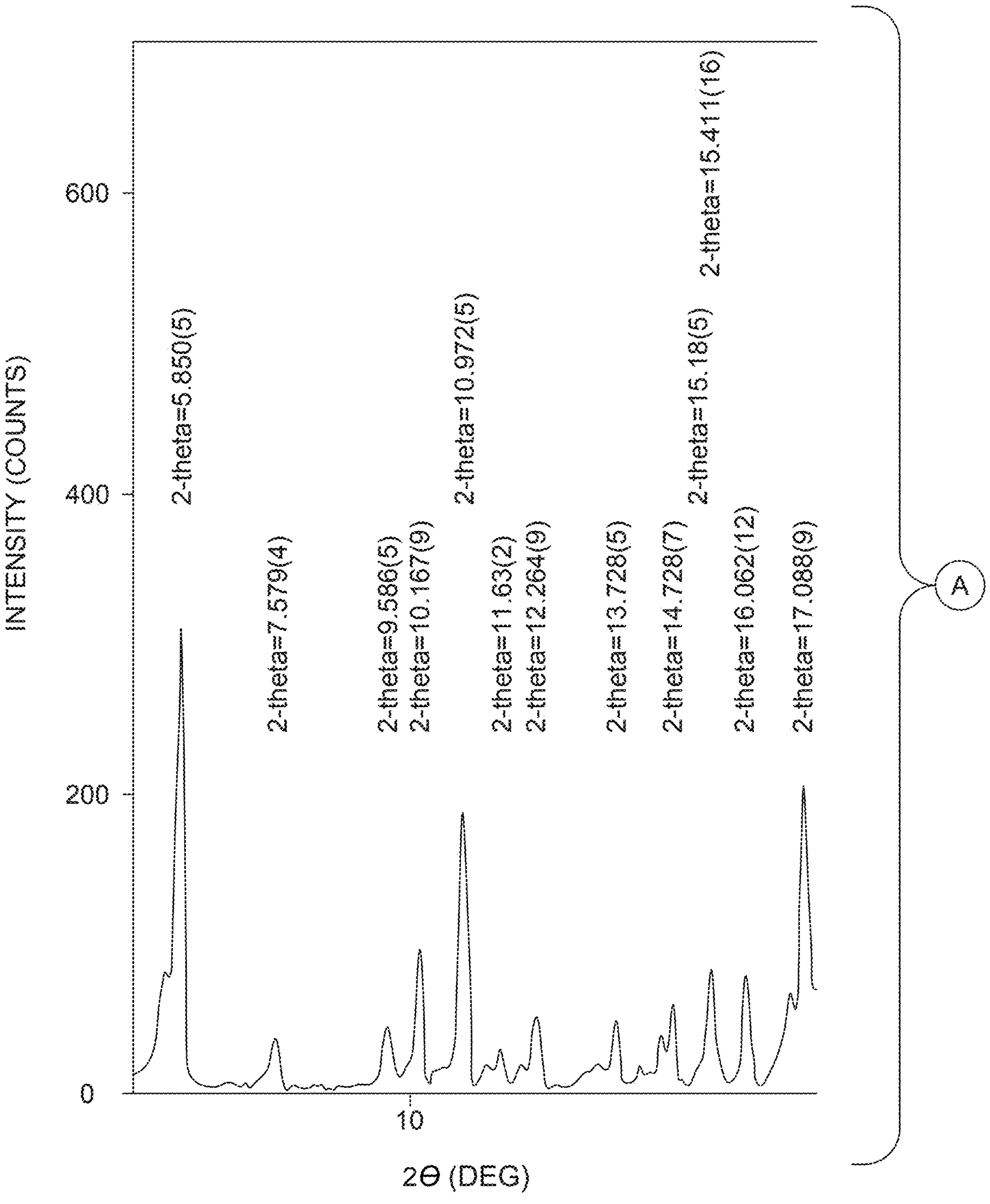
FIG. 3 Powder X-ray diffraction spectrum of the crystalline form (Form CO) of sofpironium bromide prepared in Example 6.

FIG. 3 shows the diffraction pattern of Form CO prepared in Example 6. The characteristic diffraction angles are shown in Table 7.

TABLE 7

| 2θ |
|---|
| 5.9 |
| 7.6 |
| 11.0 |
| 19.6 |
| 21.6 |
| 22.2 |

As a result of comparison of the crystalline form of Example 6, and the crystalline form of Preparation Example 7-3 on the basis of powder X-ray diffraction, it was found that diffraction patterns of the both were identified. That is, presence of a cocrystal (Form CO) constituted by 25% of the compound (I-a) and 75% of the compound (I-b) was confirmed.

The sofpironium bromides of Preparation Example 7 and Preparation Example 7-2 showed both the peak originating in Form CO and the peak originating in Form MN. Accordingly, they are considered to be a mixture of the crystals of Form CO and Form MN.

On the other hand, Form CO was not observed in Test Example 1-1 (Preparation Example 6, and Preparation Example 6-2). It was thus demonstrated that selection of the conditions of preparation method (for example, recrystallization method) is very important for the preparation of Form CO.

Specifically, it became clear that, for the preparation of Form CO, the step of adding methyl t-butyl ether dropwise over a long period of time (for example, dropping over 1 hours or longer), and/or the step of stirring the suspension of a crystalline form of sofpironium bromide in a solvent containing methyl t-butyl ether for a long period of time (for example, 13 hours) is important.

Test Example 2 <Solid-State $^{13}C$ Nuclear Magnetic Resonance Spectrometry (Solid-State $^{13}C$-NMR) of Crystalline Forms>

Each sample of Form B, Form MN, Form MJ, and Form CO was filled in a 4 mm (phi) zirconia rotor, and solid-state $^{13}C$ nuclear magnetic resonance spectrum thereof was determined by using polydimethylsiloxane as the standard substance under the following conditions.

<Conditions of Solid-State $^{13}C$ Nuclear Magnetic Resonance Spectrometry>

TABLE 8

| Item | Conditions |
|---|---|
| Measurement method | CP/MAS |
| Measured nuclear frequency | 100 MHz |
| Spectral bandwidth | 40 kHz |
| Pulse width | 3.5 μs (90° pulse) |
| Contact time | 4 ms |
| Sample rotation number | 17 kHz |

The results are shown in FIGS. 4 to 8.

Figure 4:
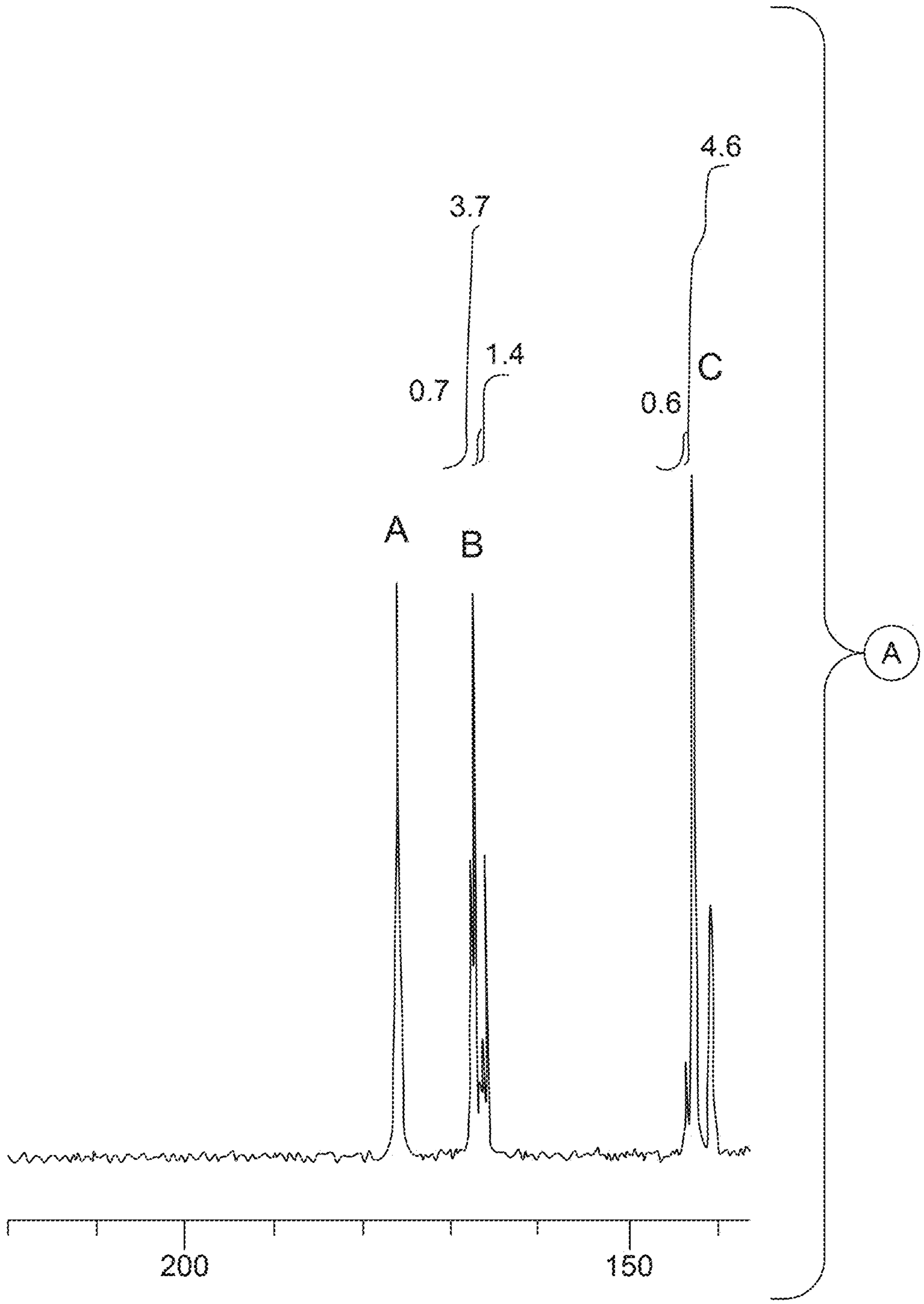
FIG. 4 Solid-state $^{13}C$ nuclear magnetic resonance spectrum of the crystalline form (Form B) of sofpironium bromide prepared in Example 3.

FIG. 4 shows the solid-state $^{13}C$ nuclear magnetic resonance spectrum of the crystalline form of the compound (I) (Form B). The characteristic peaks are shown in the Table 9.

TABLE 9

| Peak (ppm) |
|---|
| 13.1 |
| 14.6 |
| 15.2 |
| 25.5 |
| 26.9 |
| 28.8 |
| 32.3 |
| 43.9 |
| 46.0 |
| 48.5 |
| 50.1 |
| 50.5 |
| 51.5 |
| 52.2 |
| 61.4 |

TABLE 9-continued

| Peak (ppm) |
|---|
| 62.3 |
| 63.2 |
| 63.8 |
| 67.6 |
| 70.5 |
| 71.4 |
| 73.1 |
| 74.1 |
| 80.1 |
| 80.5 |
| 81.0 |
| 83.0 |
| 125.4 |
| 126.8 |
| 128.8 |
| 130.2 |
| 131.4 |
| 140.8 |
| 142.8 |
| 143.7 |
| 166.1 |
| 166.6 |
| 167.4 |
| 167.9 |
| 175.8 |
| 176.3 |

The content ratio of the compound (I-a) and the compound (I-b) in Form B used in this test was 33:67.

Figure 5:
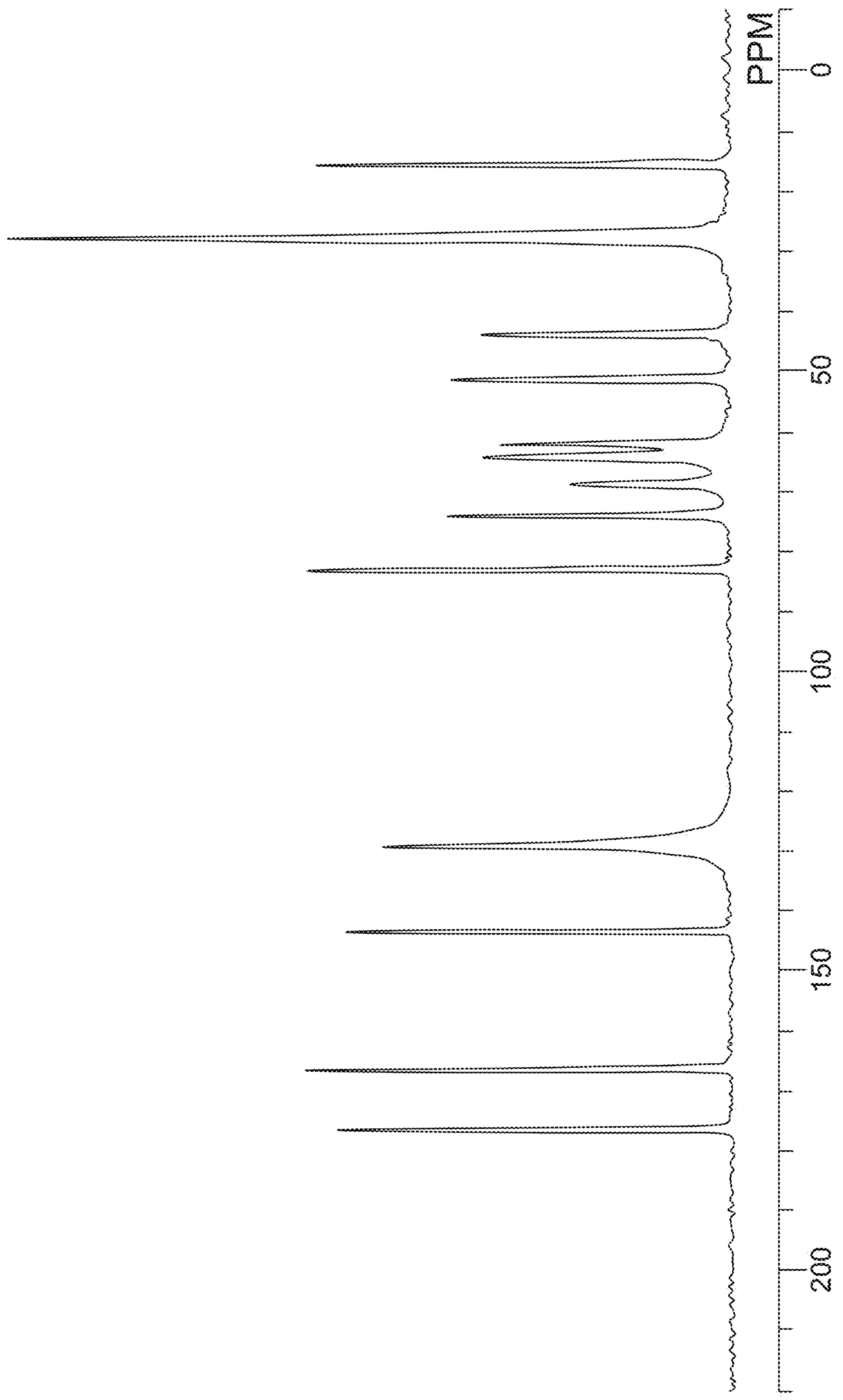
FIG. 5 Solid-state $^{13}C$ nuclear magnetic resonance spectrum of the crystalline form (Form MN) of sofpironium bromide prepared in Preparation Example 4.

FIG. 5 shows the solid-state $^{13}C$ nuclear magnetic resonance spectrum of the crystalline form of the compound (I-a) (Form MN). The characteristic peaks are shown in Table 10.

TABLE 10

| Peak (ppm) |
|---|
| 15.5 |
| 27.8 |
| 43.9 |
| 51.4 |
| 62.2 |
| 64.2 |
| 69.0 |
| 74.0 |
| 83.0 |
| 129.2 |
| 143.6 |
| 166.6 |
| 176.6 |

Figure 6:
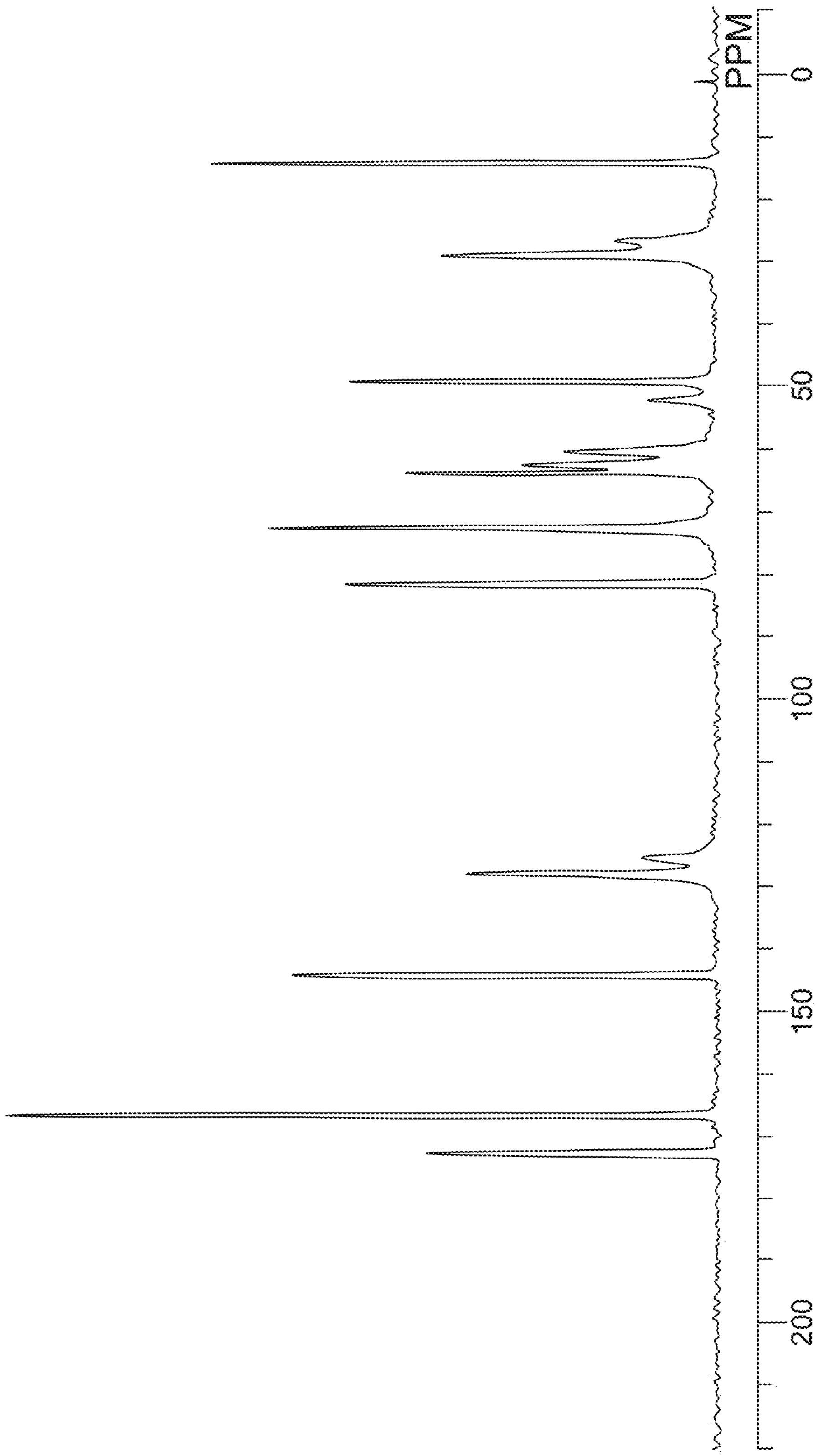
FIG. 6 Solid-state $^{13}C$ nuclear magnetic resonance spectrum of the crystalline form (Form MJ) of sofpironium bromide prepared in Preparation Example 5.

FIG. 6 shows the solid-state $^{13}C$ nuclear magnetic resonance spectrum of the crystalline form of the compound (I-b) (Form MJ). The characteristic peaks are shown in Table 11.

TABLE 11

| Peak (ppm) |
|---|
| 14.5 |
| 26.9 |
| 29.2 |
| 49.4 |
| 52.3 |
| 60.5 |
| 62.7 |
| 63.9 |
| 72.8 |
| 81.7 |
| 125.7 |
| 128.2 |

TABLE 11-continued

| Peak (ppm) |
|---|
| 144.5 |
| 166.8 |
| 172.8 |

Figure 7:
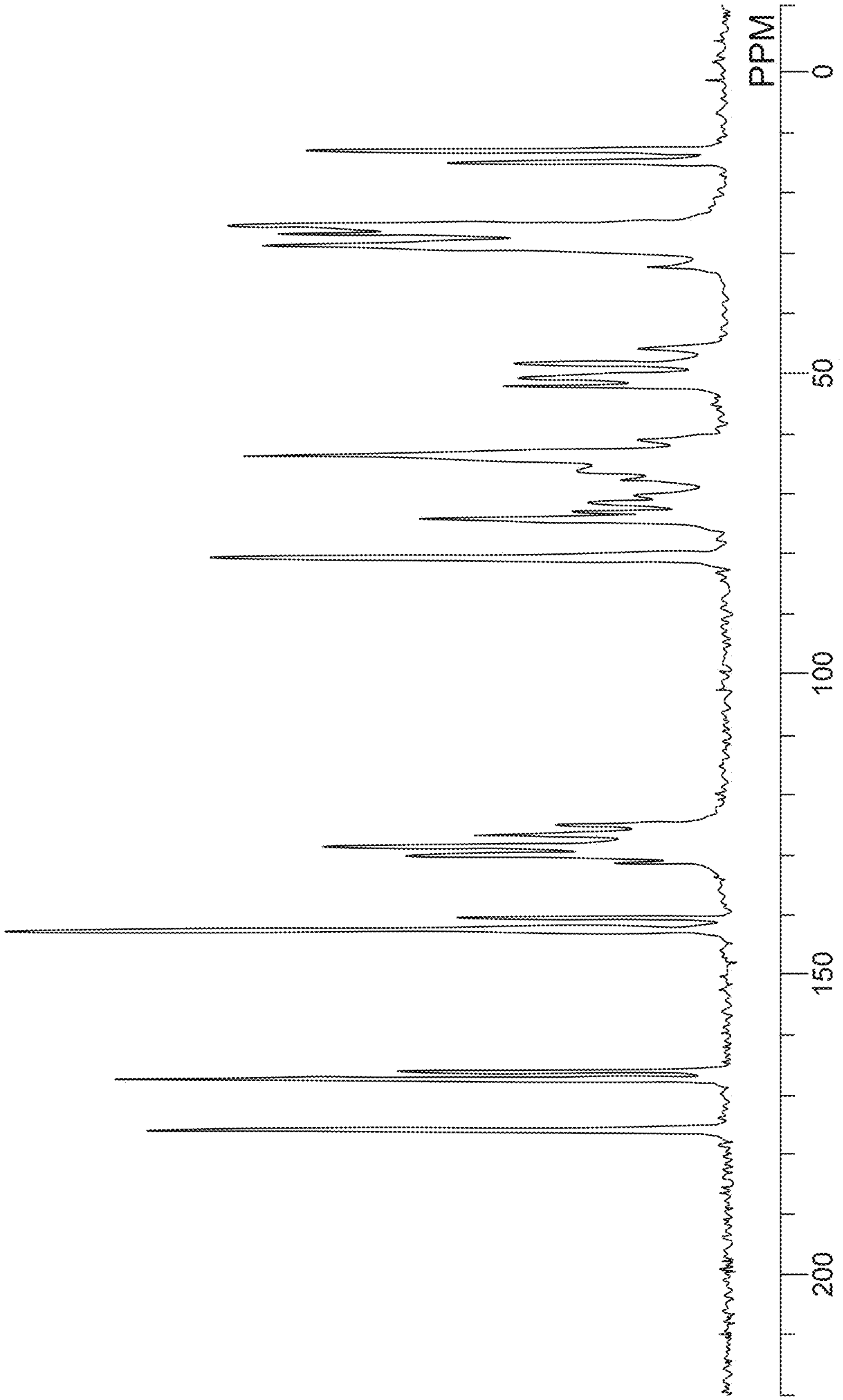
FIG. 7 Solid-state $^{13}C$ nuclear magnetic resonance spectrum of the crystalline form (Fora CO) of sofpironium bromide prepared in Example 6.

FIG. 7 shows the solid-state $^{13}C$ nuclear magnetic resonance spectrum of the crystalline form of the compound (I) (Form CO). The characteristic peaks are shown in Table 12.

TABLE 12

| Peak (ppm) |
|---|
| 13.0 |
| 14.5 |
| 15.1 |
| 25.5 |
| 26.8 |
| 28.7 |
| 32.2 |
| 46.0 |
| 48.4 |
| 50.1 |
| 50.5 |
| 51.4 |
| 52.2 |
| 61.3 |
| 63.1 |
| 63.7 |

TABLE 12-continued

| Peak (ppm) |
|---|
| 67.5 |
| 70.4 |
| 71.6 |
| 73.1 |
| 74.1 |
| 80.1 |
| 80.5 |
| 80.9 |
| 125.3 |
| 126.8 |
| 128.7 |
| 130.1 |
| 131.3 |
| 140.8 |
| 142.7 |
| 166.0 |
| 167.4 |
| 167.9 |
| 175.7 |
| 176.2 |

The solid-state $^{13}C$ nuclear magnetic resonance spectrum of Form B shown in FIG. 4 is extremely complicated, and many peaks were observed. However, the spectrum characteristic to Form B observed around 140 ppm agreed with the spectrum characteristic to Form CO and Form MN as shown in Table 13, and therefore the crystalline form of Form B was confirmed as a mixture of Form CO and Form MN.

TABLE 13

| Example/ Preparation Example | Crystalline form | Content ratio of compound (I-a) (%) | Content ratio of compound (I-b) (%) | Characteristic peak (ppm)* 140.8 | 142.7-142.8 | 143.6-143.7 | 144.5 |
|---|---|---|---|---|---|---|---|
| Example 3 | Form B | 33 | 67 | Observed | Observed | Observed | |
| Preparation Example 4 | Form MN | 100 | 0 | | | Observed | |
| Preparation Example 5 | Form MJ | 0 | 100 | | | | Observed |
| Example 6 | Form CO | 25 | 75 | Observed | Observed | | |

*"Observed" means that a peak was observed at the corresponding chemical shift value. The blank means that the peak was not observed.

In the solid-state $^{13}C$ nuclear magnetic resonance spectrometry (CP/MAS method), the measurement is performed by transferring magnetization of $^{1}H$ nuclei to $^{13}C$ nuclei by cross polarization. The efficiency of transferring magnetization of $^{1}H$ nuclei to $^{13}C$ nuclei varies depending on positions, molecular motility and the like of $^{13}C$ nuclei and $^{1}H$ nuclei. The integration data obtained in the solid-state $^{13}C$ nuclear magnetic resonance spectrometry (CP/MAS method) is not quantitative, and an abundance ratio of compounds cannot be obtained from the integrated intensity ratio of peaks directly.

However, it is considered that the CP efficiency does not significantly change among $^{13}C$ nuclei in similar environments, and the abundance ratio of crystalline forms can be tentatively estimated from the signal intensities.

Form CO comprises cocrystal of the compound (I-a) and the compound (I-b) having a content ratio of 1:3 as elucidated in Test Example 1. Accordingly, the content ratio of Form CO and Form MN in Form B, of which the content ratio of the compound (I-b) is 67%, is theoretically 89:11.

Figure 8:
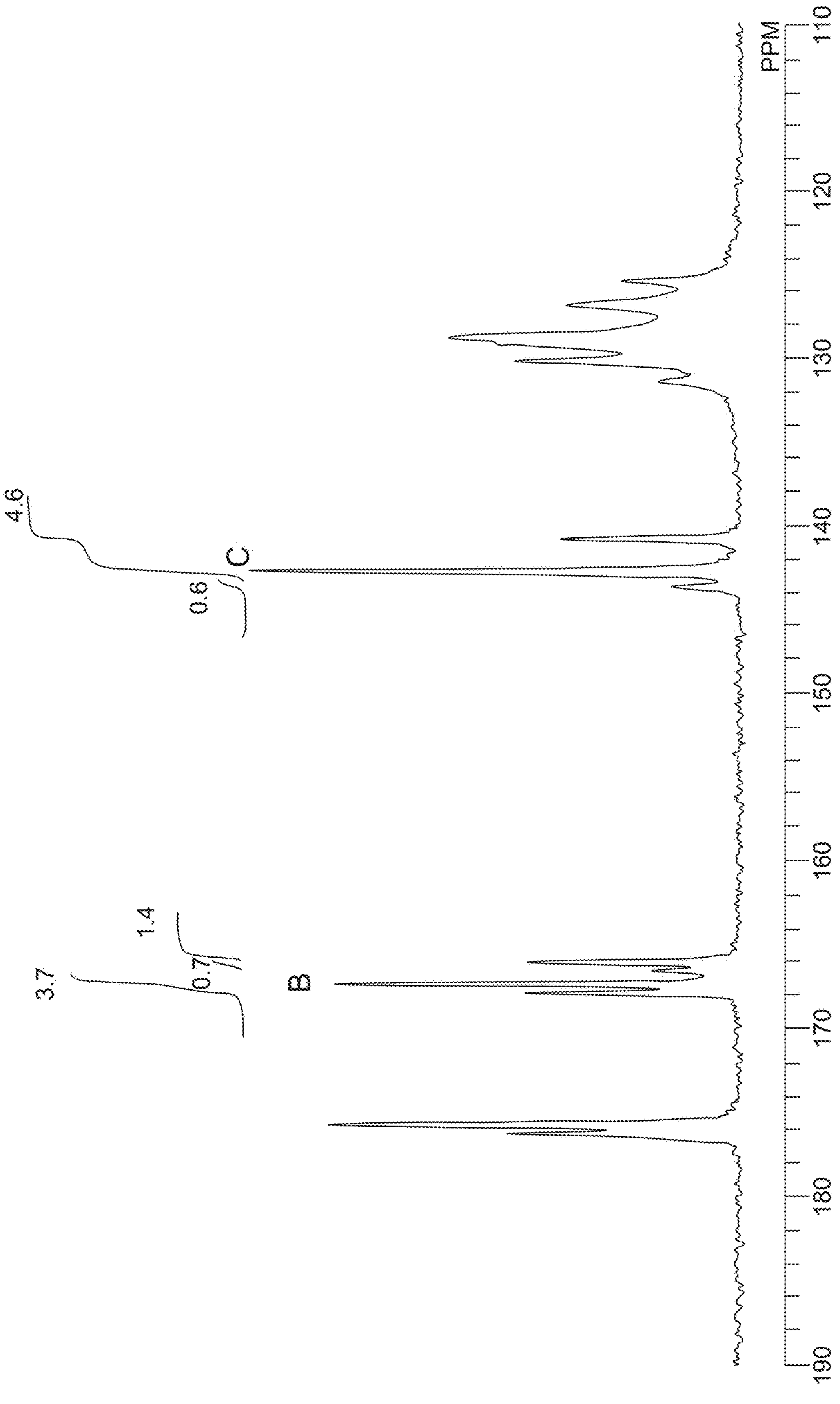
FIG. 8 The solid-state $^{13}C$ nuclear magnetic resonance spectrum shown in FIG. 4 enlarged for 110 to 190 ppm, FIG. 9 Powder X-ray diffraction spectrum of the crystalline forte (Form A) of sofpironium bromide prepared in Example 1.

The enlarged chart of solid-state $^{13}C$ nuclear magnetic resonance spectrum of Form B shown in FIG. 8 shows integration data of both the peak originating in Form CO and the peak originating in Form MN, and for example, the ratio of the peak area originating in Form CO and Form MN was 4.6:0.6 (about 88:12) around 140 ppm.

On the basis of the results mentioned above, it became clear that the crystalline form of Form B is a crystal mixture of Form CO and Form MN.

Test Example 3 <Purity Test of Crystalline Forms (Analogous Substances)>

Purities of the crystalline forms obtained in the aforementioned examples were measured by using high performance liquid chromatography (HPLC) under following conditions.

1) Analysis Conditions

Detector: Ultraviolet absorptiometer (measurement wavelength 220 nm)

Column: Luna (2) CIS (internal diameter 4.6 mm, length 15 cm, particle diameter 3.0 μm)

Column temperature: Constant temperature around 50° C.

Flow rate: 1.2 mL/min

Injection volume: 15 μL

Eluent A: water:methanol:acetoniltrile:trifluoroacetic acid=700:200:100:1

Eluent B: methanol:acetonitrile:water:trifluoroacetic acid=6500:2500:1000:7

Feeding of eluent: Concentration gradient was controlled by changing the mixing ratio of eluent A and eluent B as follows.

TABLE 14

| Time after injection (minute) | Eluent A (vol %) | Eluent B (vol %) |
|---|---|---|
| 0-5 | 90 | 10 |
| 5-15 | 90 → 70 | 10 → 30 |
| 15-35 | 70 → 5 | 30 → 95 |
| 35-42 | 5 | 95 |
| 42-42.01 | 5 → 90 | 95 → 10 |
| 42.01-53 | 90 | 10 |

2) Preparation of Sample Solution

Each sample was weighed in an amount of about 30 mg, and 10 mL of a mixture of water, acetonitrile and trifluoroacetic acid (500:500:1) was added to prepare a sample solution.

When the relative retention time of the compound (I-b) was defined to be 1, the relative retention time of the compound (I-a) was 0.9. As for impurities, the relative retention time of the compound (III) was 0.6 and 0.7, the relative retention time of compound (IV) was 1.2, and the relative retention time of the compound (V) was 1.3.

All the crystalline forms obtained in Example 1 (Form A), Example 3 (Form B), and Example 6 (Form CO) showed a purity not lower than 99.5 w/w %, and contents of the compounds MO, (IV), and (V) as impurities not higher than 0.5 w/w %. As for the peaks of impurities other Than the compounds (III), (IV), and (V), contents thereof were lower than the quantification limit.

Therefore, it was revealed that the compound (I) of the present invention (including crystalline form of the compound (I)) prepared by the aforementioned methods has high purity.

Test Example 4 <Powder X-Ray Diffraction Pattern Analysis of Form A and Form B>

Figure 10:
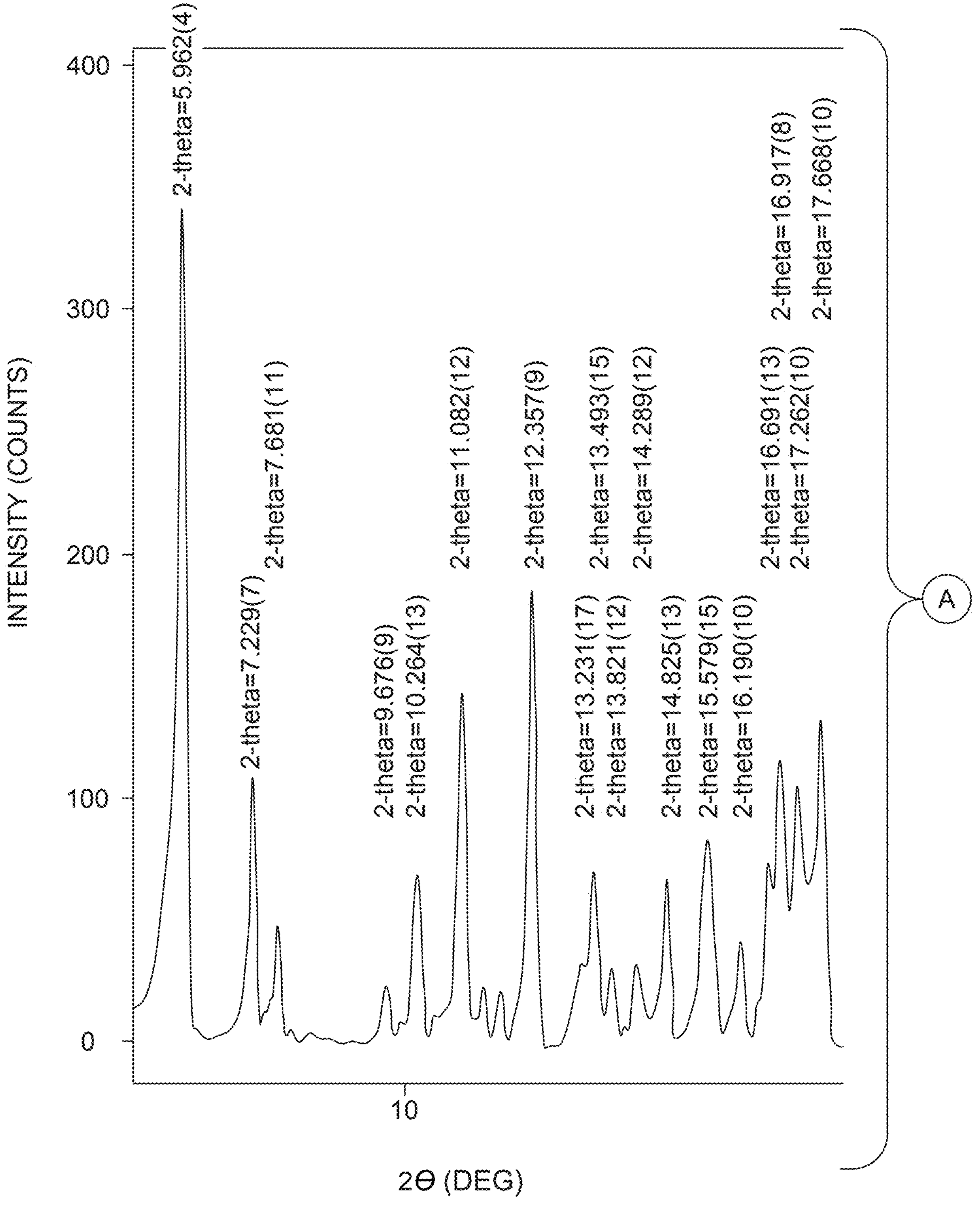
FIG. 10 Powder X-ray diffraction spectrum of the crystalline form (Form B) of sofpironium bromide prepared in Example 3.
Figure 11:
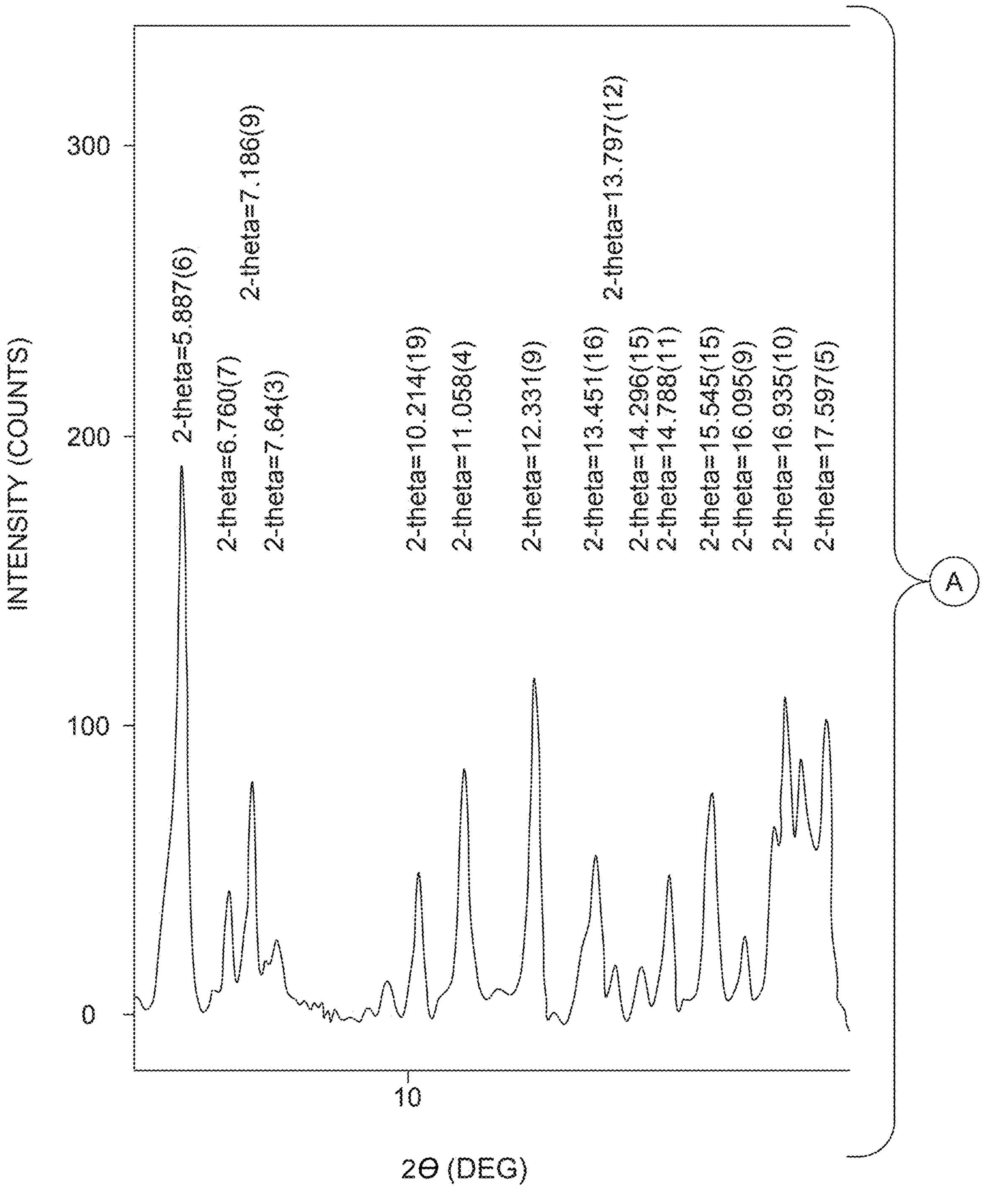
FIG. 11 Powder X-ray diffraction spectrum of the crystalline form (Form B) of sofpironium bromide prepared in Example 5.
Figure 12:
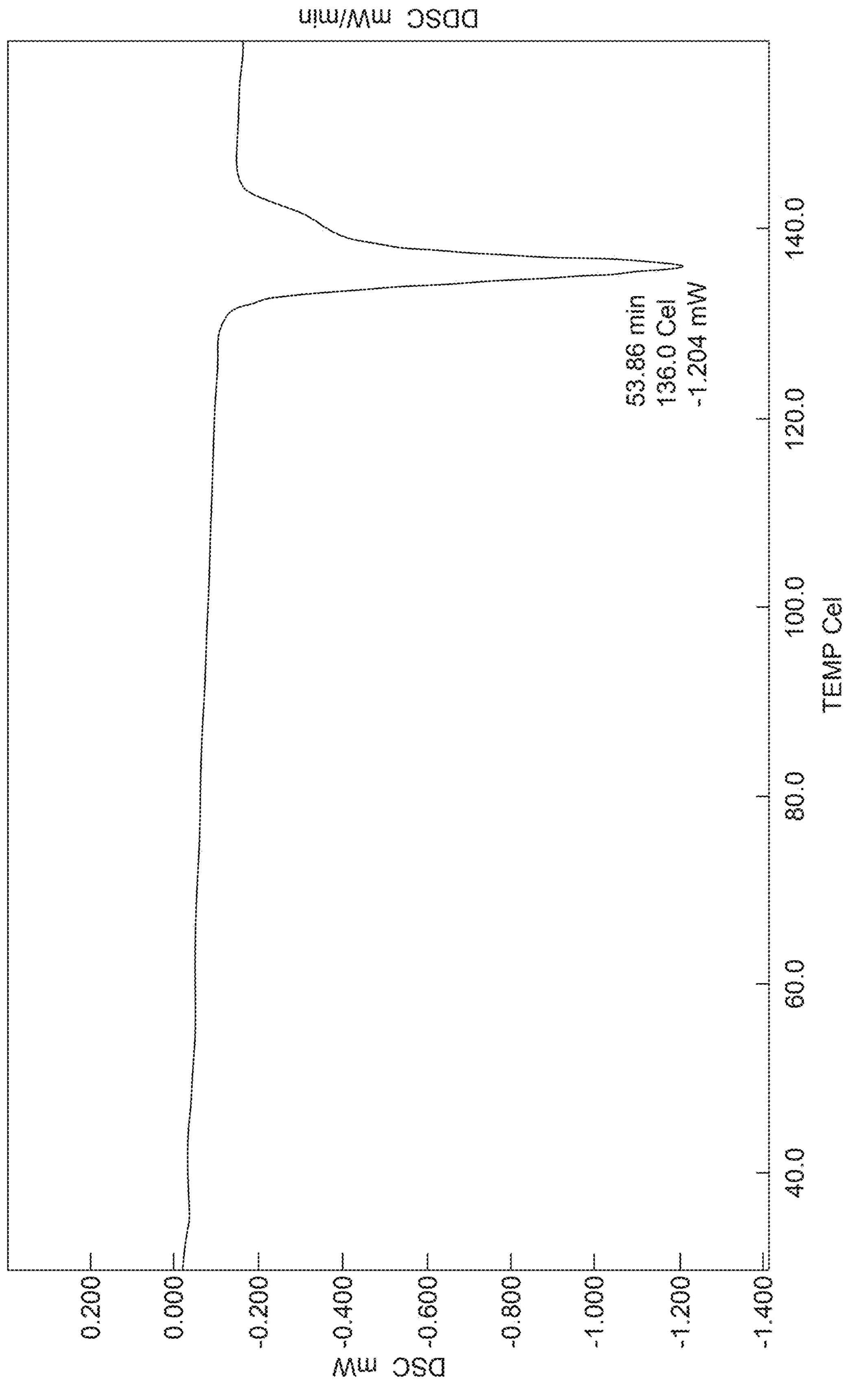
FIG. 12 Differential scanning calorimetry (DSC) chart of the crystalline form (Form A) of sofpironium bromide prepared in Example 1.
Figure 13:
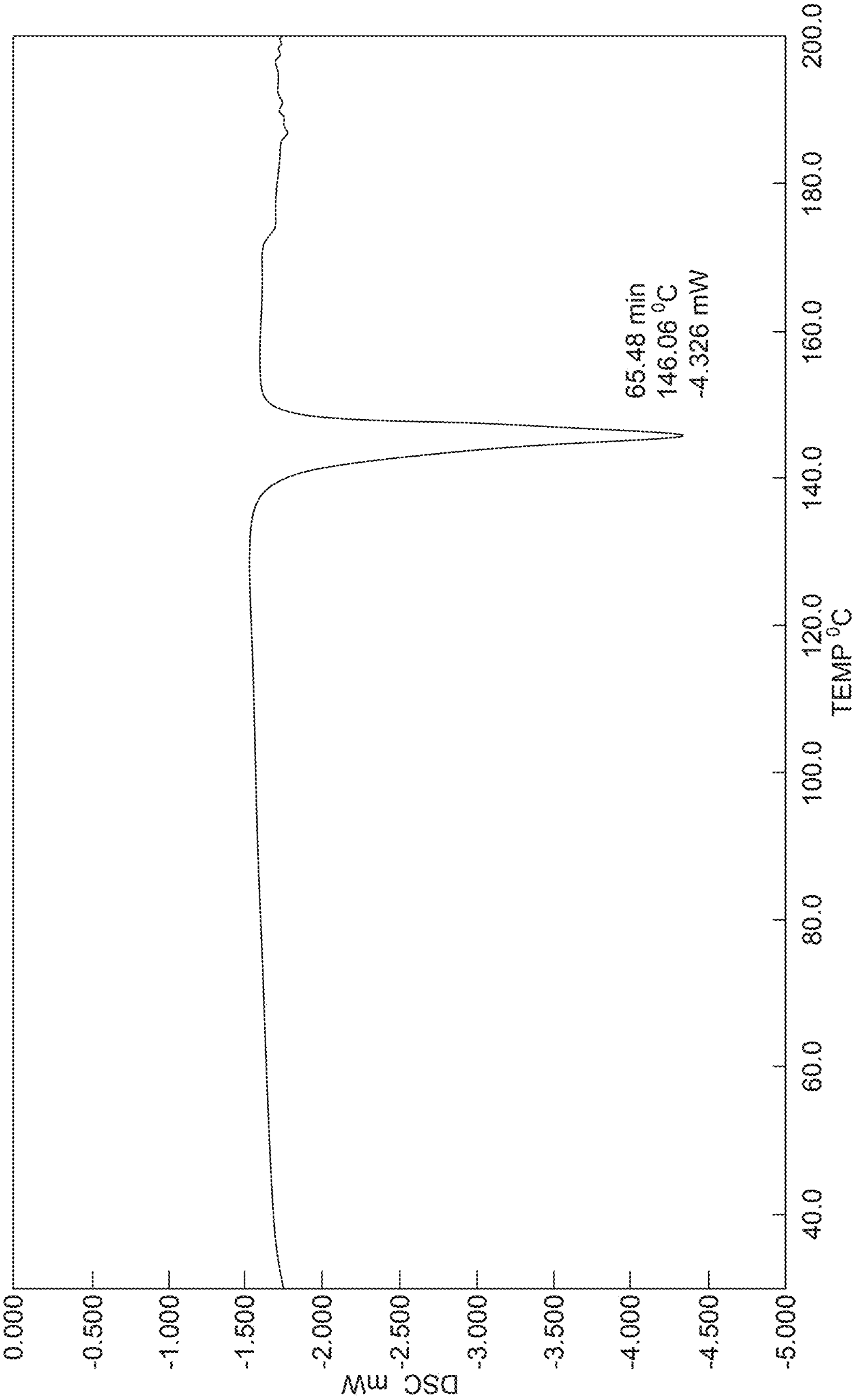
FIG. 13 Differential scanning calorimetry (DSC) chart of the crystalline form (Form B) of sofpironium bromide prepared in Example 3.
Figure 14:
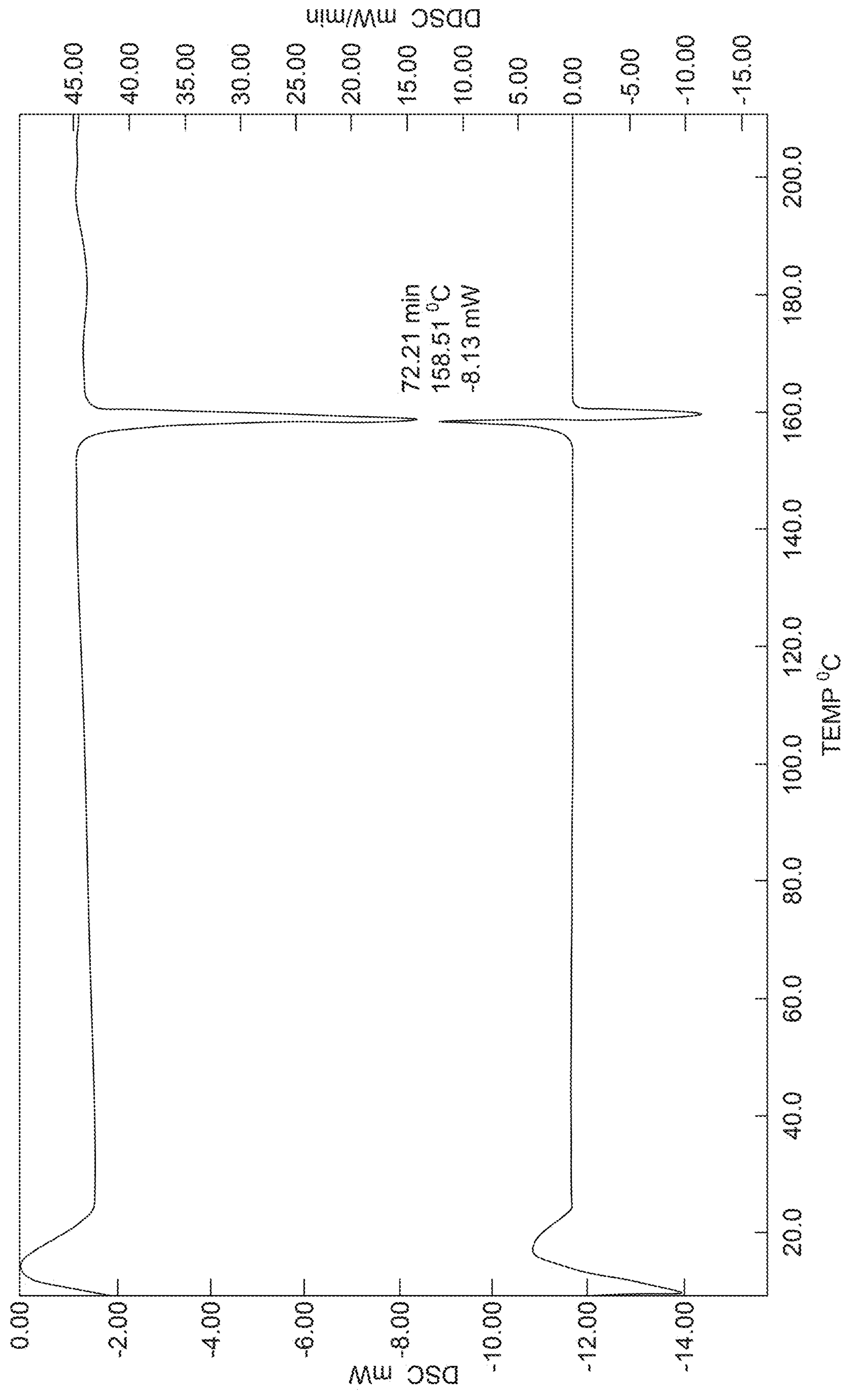
FIG. 14 Differential scanning calorimetry (DSC) chart of the crystalline form (Form MN) of sofpironium bromide prepared in Preparation Example 4.
Figure 15:
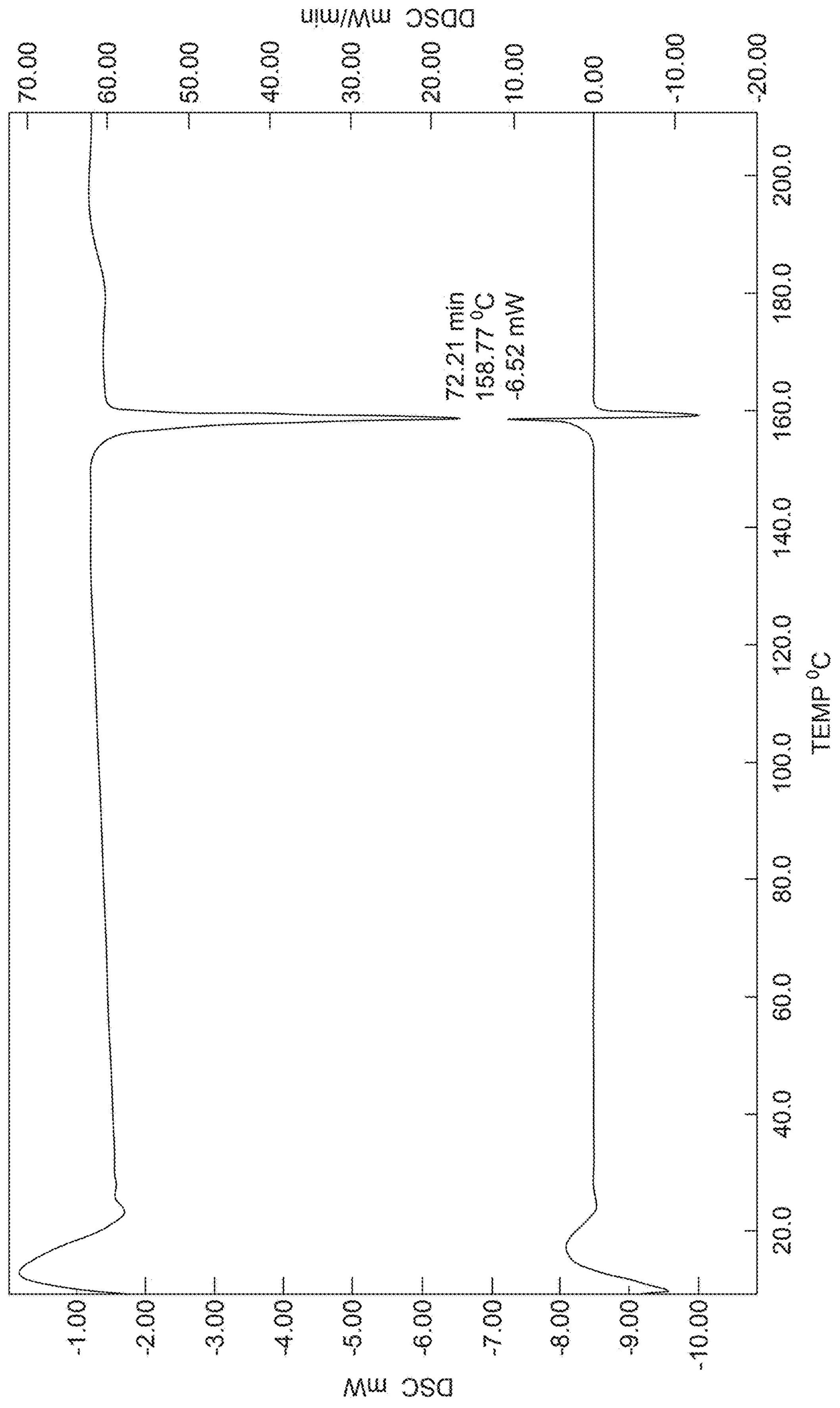
FIG. 15 Differential scanning calorimetry (DSC) chart of the crystalline form (Form MJ) of sofpironium bromide prepared in Preparation Example 5.
Figure 16:
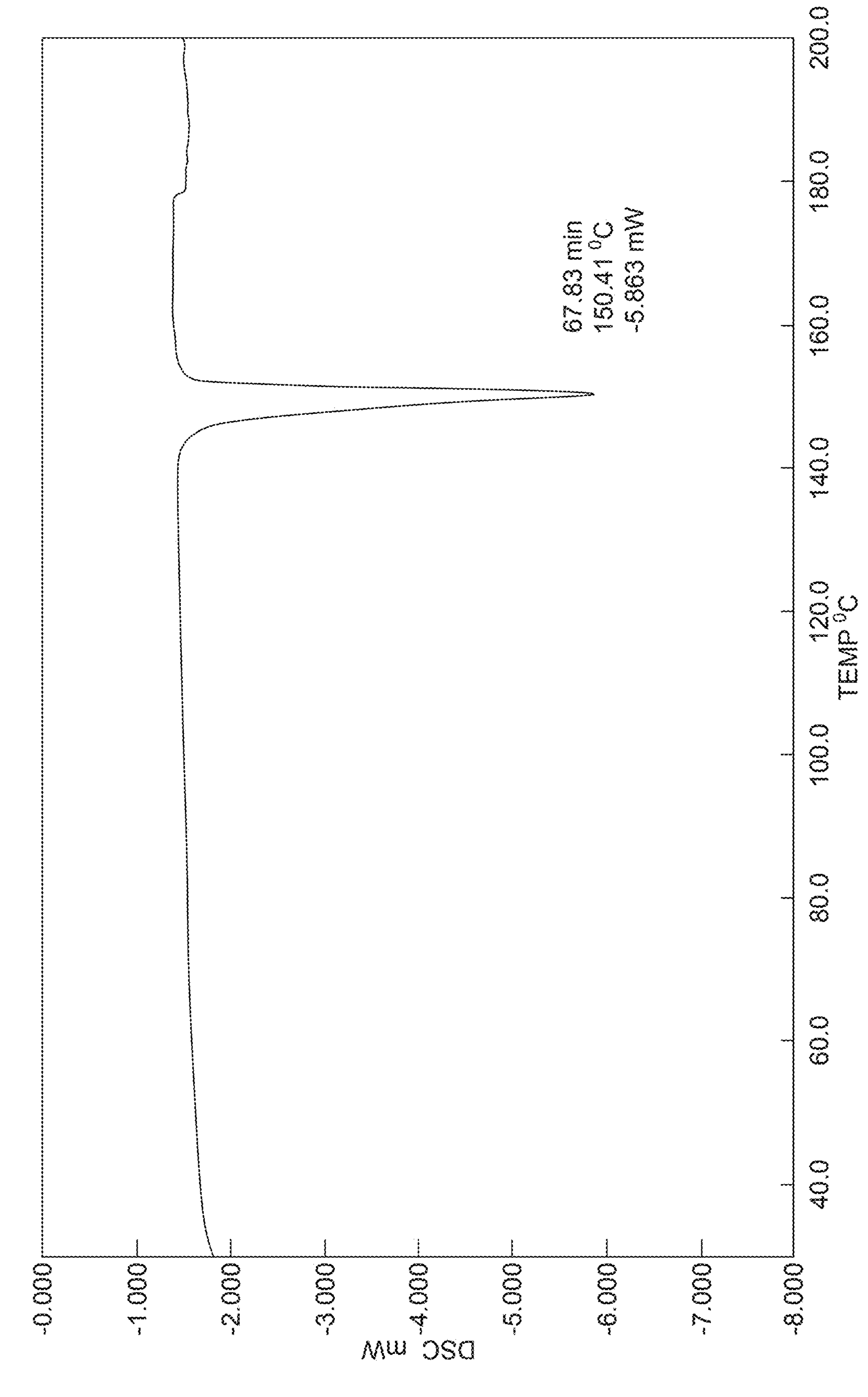
FIG. 16 Differential scanning calorimetry (DSC) chart of the crystalline form (Form CO) of sofpironium bromide prepared in Example 6.

According to the method described in Test Example 1-1, powder X-ray diffraction pattern of Form A and Form B was measured. Diffraction angles 2θ of the same crystalline forms usually agree with each other with a margin of ±0.2° or ±0.1°. The results are shown in FIGS. 9 to 11.

Figure 9:
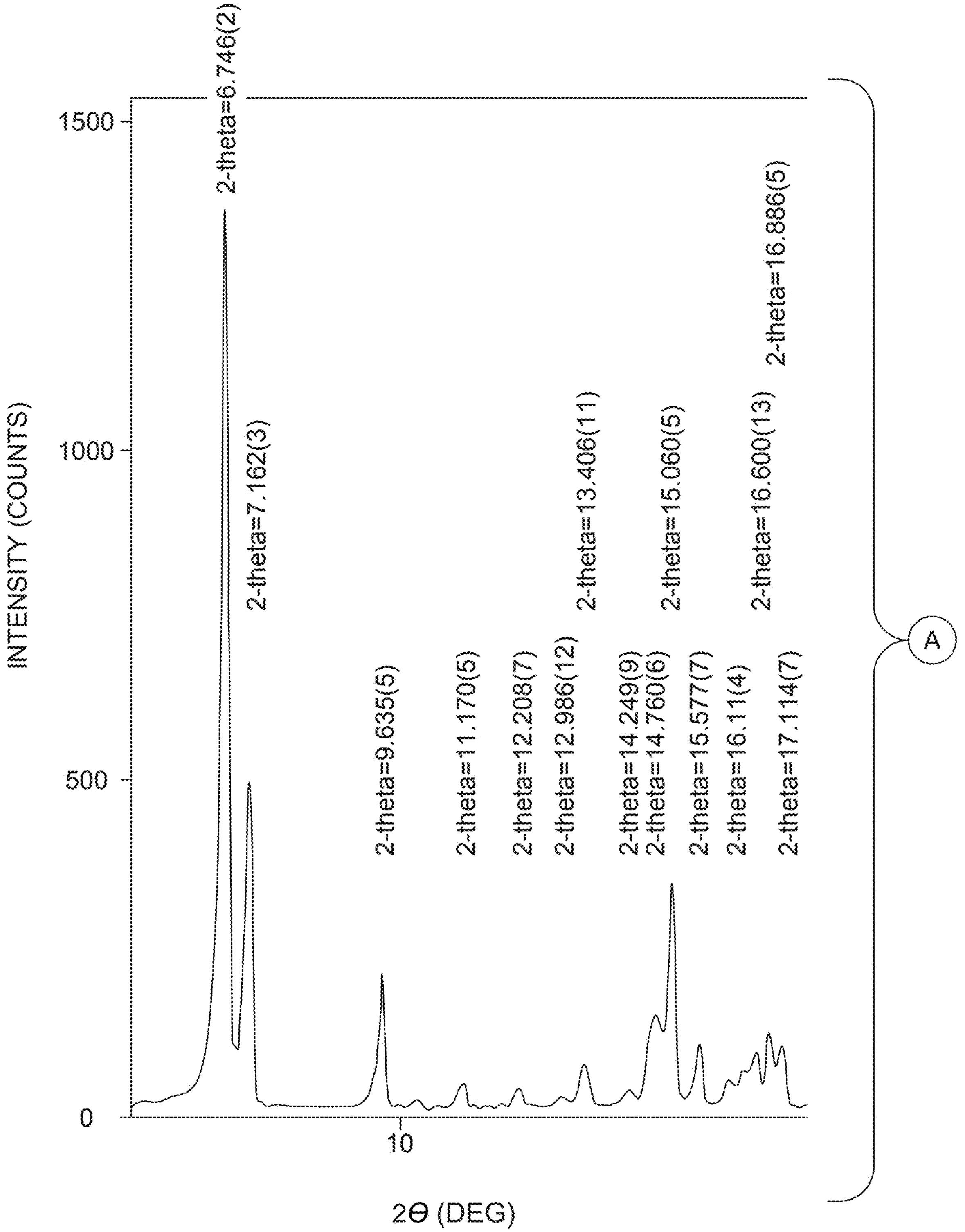

FIG. 9 shows the diffraction pattern of the crystalline form of the compound (I) (Form A). The characteristic diffraction angles are shown in Table 15.

TABLE 15

| 2θ |
|---|
| 6.7 |
| 7.2 |
| 9.6 |
| 15.1 |
| 19.2 |
| 20.1 |
| 22.3 |
| 24.5 |

In the powder X-ray diffraction pattern analysis of the crystalline form of Form A, the peak at the diffraction angle 2θ=7.1±0.1° characteristic to Form MN and the peaks at diffraction angle 2θ=6.7±0.1° characteristic to Form MJ were observed. Therefore, Form A comprises a crystal mixture of Forms MN and Form MJ.

The content ratio of the compound (I-a) and the compound (I-b) contained in Form A used in this test was within the range of 40:60 to 25:75.

FIG. 10 shows the diffraction pattern of the crystalline form of the compound (I) (Form B). The characteristic diffraction angles are shown in Table 16.

TABLE 16

| 2θ |
|---|
| 5.9 |
| 7.2 |
| 7.7 |
| 10.3 |
| 11.1 |
| 12.4 |
| 22.3 |
| 24.6 |

In the powder X-ray diffraction pattern analysis of the crystalline form of Form B, both the peak at the diffraction angle 2θ=7.1±0.1° characteristic to Form MN, and the peaks at the diffraction angles 2θ=5.9±0.0° and 2θ=7.6±0.1° characteristic to Form CO were observed. Therefore, Form B comprises a crystal mixture of Form MN and Form CO.

The content ratio of the compound (I-a) and the compound (I-b) contained in Form B used in this test was within the range of 40:60 to 25:75.

Test Example 5 <Thermal Analysis (DSC) of Crystalline Forms>

According to the thermal analysis method described in Japanese Pharmacopoeia (17th Edition), each sample was weighed in an amount of 5 to 6 mg on an aluminum pan (drop lid), and measured at a heating rate of 2° C./minute in the range of 30 to 230° C. under a nitrogen flow (50 mL per minute). α-Alumina was used as standard substance.

As an alternative method, according to the thermal analysis method described in Japanese Pharmacopoeia (17th Edition), each sample was weighed in an amount of l to 2 mg on an aluminum pan (easy sealing type), and measured at a heating rate of 2° C./minute in the range of 30 to 165° C. under a nitrogen flow (50 mL per minute). α-Alumina was used as standard substance.

The results are shown in FIGS. 12 to 16.

TABLE 17

| Crystalline form | DSC endothermic peak | Peak shape |
|---|---|---|
| Form A | 136° C. | Single sharp endothermic peak |
| From B | 146° C. | Single sharp endothermic peak |
| From MN | 159° C. | Single sharp endothermic peak |
| Form MJ | 159° C. | Single sharp endothermic peak |
| Form CO | 150° C. | Single sharp endothermic peak |

The value of the endothermic peak of Form A was lower than those of Form MN and Form MJ. The value of the endothermic peak of Form B was lower than those of Form MN and Form CO.

In general, the melting point of a compound containing impurities is lower than the melting point of the corresponding pure substance. It is considered that Form MN, Form MJ, and Form CO serve as an impurity for each other in the crystalline form of Form A or Form B, and therefore each endothermic peak of Form A and Form B was observed at a value lower than those of Form MN, Form MJ and Form CO.

The content ratios of the compound (I-a) and the compound (I-b) contained in Form A and Form B used in this test were within the range of 40:60 to 25:75.

Test Example 6 <Infrared Absorption Spectrometry (IR) of Crystalline Forms>

Each sample was analyzed according to the potassium bromide disk method of the infrared absorption spectrometry described in Japanese Pharmacopoeia (17th Edition), The results are shown in FIGS. 17 to 21.

Figure 17:
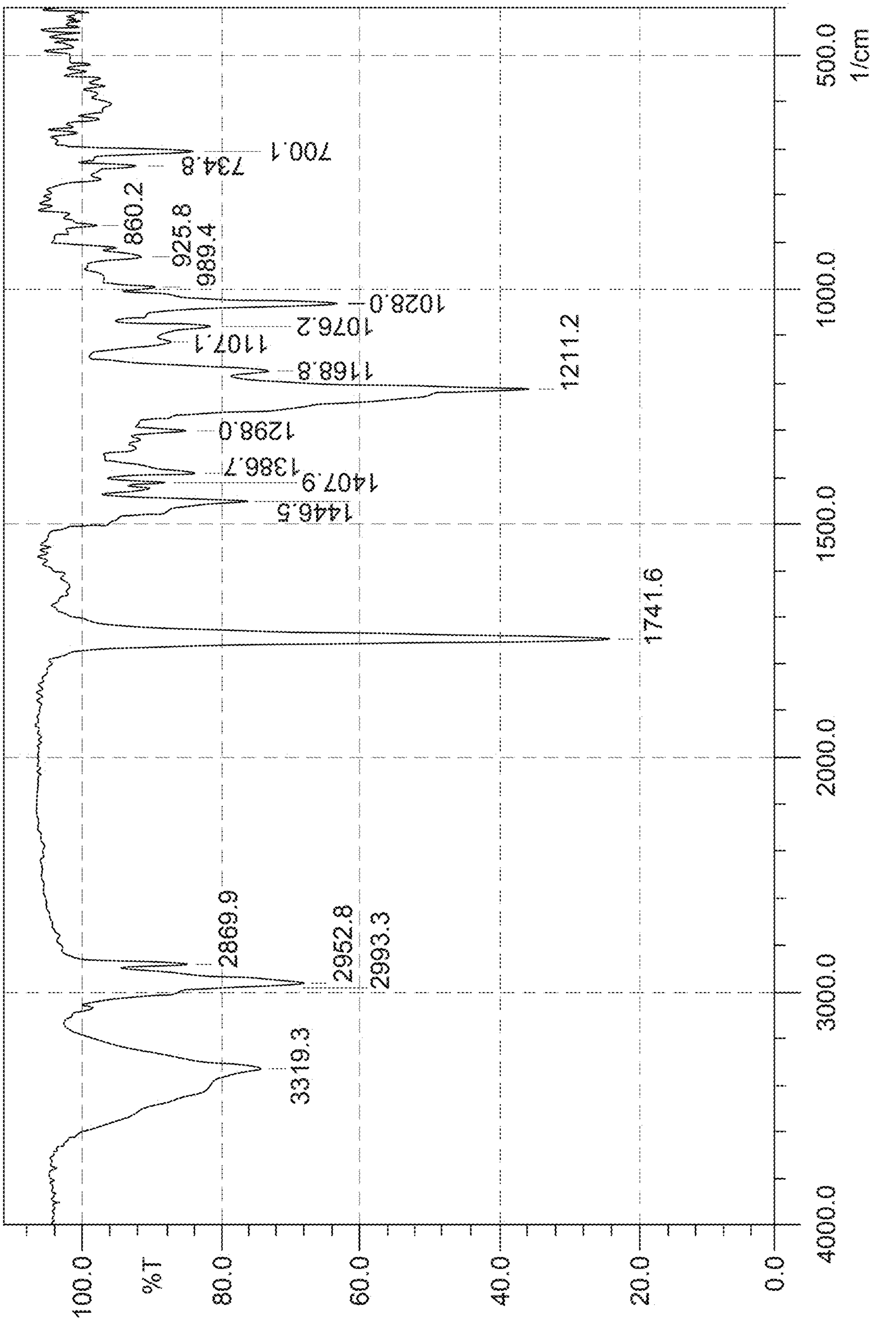
FIG. 17 Infrared absorption spectrum of the crystalline form (Form A) of sofpironium bromide prepared in Example 1.

FIG. 17 is the IR chart of the crystalline form of the compound (I) (Form A). The characteristic peaks are shown in Table 18.

TABLE 18

| Peak ($cm^{-1}$) |
|---|
| 3319 |
| 2953 |
| 1742 |
| 1447 |
| 1211 |
| 1028 |

Figure 18:
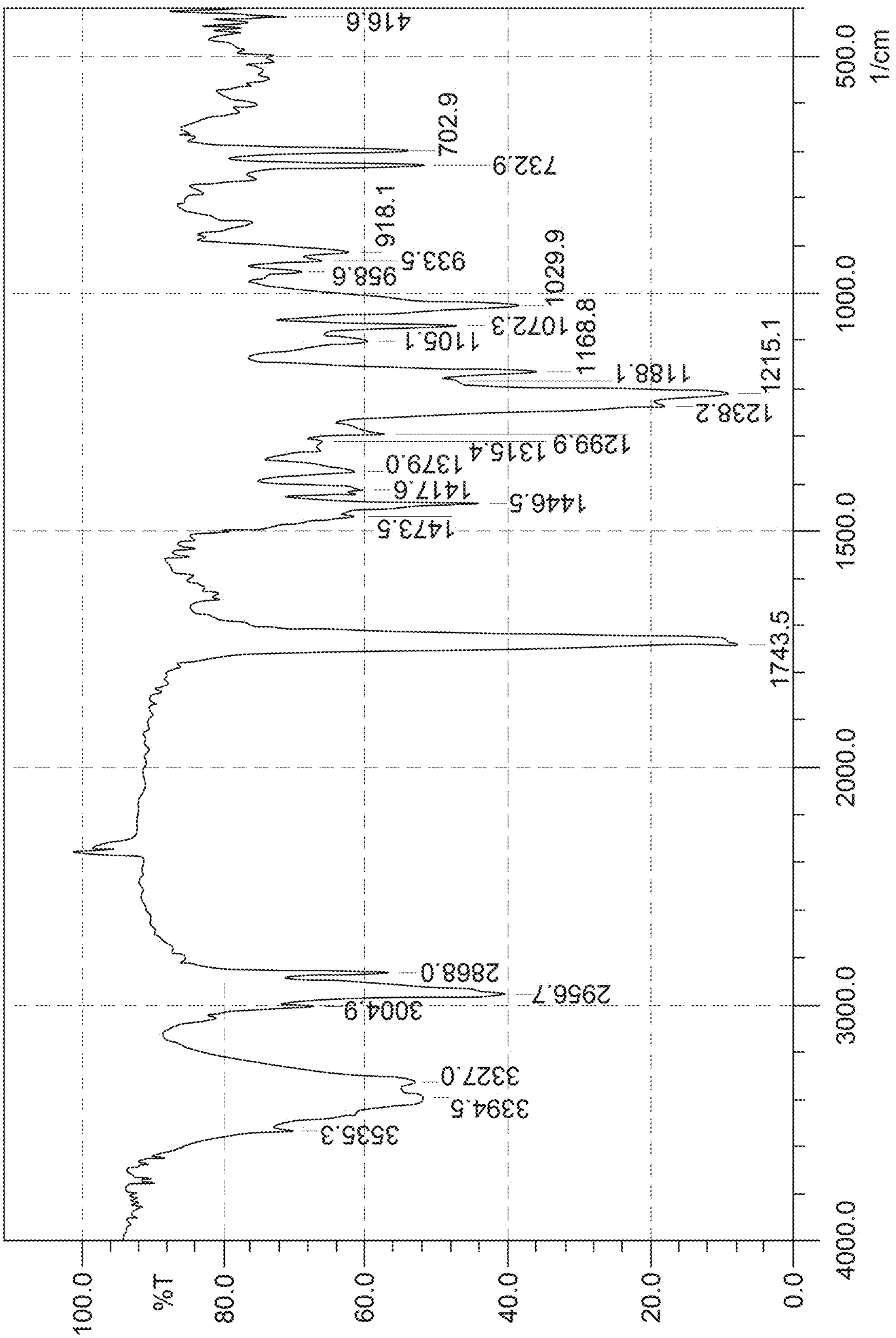
FIG. 18 Infrared absorption spectrum of the crystalline form (Form B) of sofpironium bromide prepared in Example 3.

FIG. 18 is the IR chart of the crystalline form of the compound (I) (Form B). The characteristic peaks are shown in Table 19.

TABLE 19

| Peak ($cm^{-1}$) |
|---|
| 3395 |
| 3327 |
| 2957 |
| 1744 |
| 1447 |
| 1215 |

Figure 19:
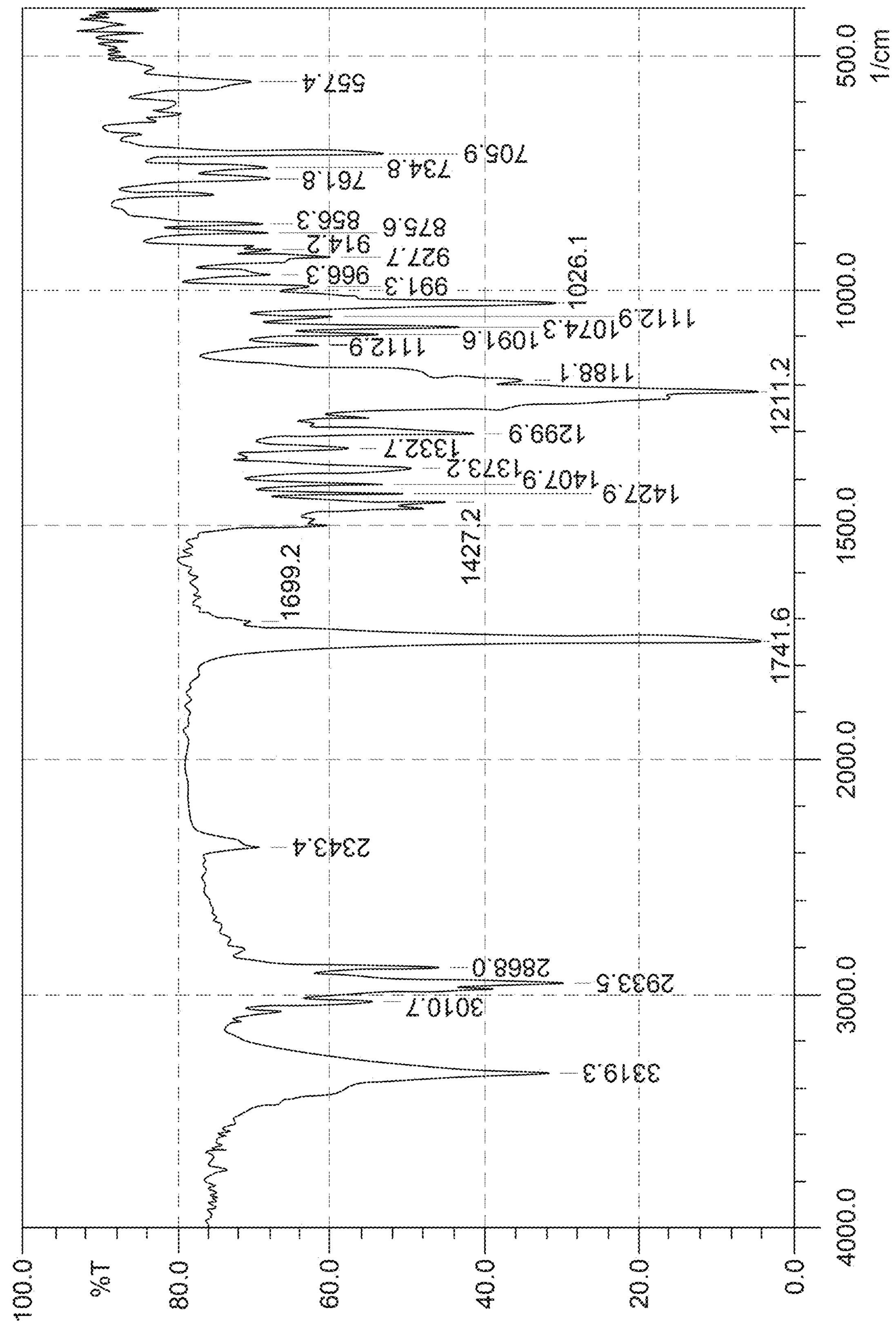
FIG. 19 Infrared absorption spectrum of the crystalline form (Form MN) of sofpironium bromide prepared in Preparation Example 4.

FIG. 19 is the IR chart of the crystalline form of the compound (I-a) (Form MN). The characteristic peaks are shown in Table 20.

TABLE 20

| Peak ($cm^{-1}$) |
|---|
| 3319 |
| 2934 |
| 1742 |
| 1448 |
| 1211 |
| 1026 |

Figure 20:
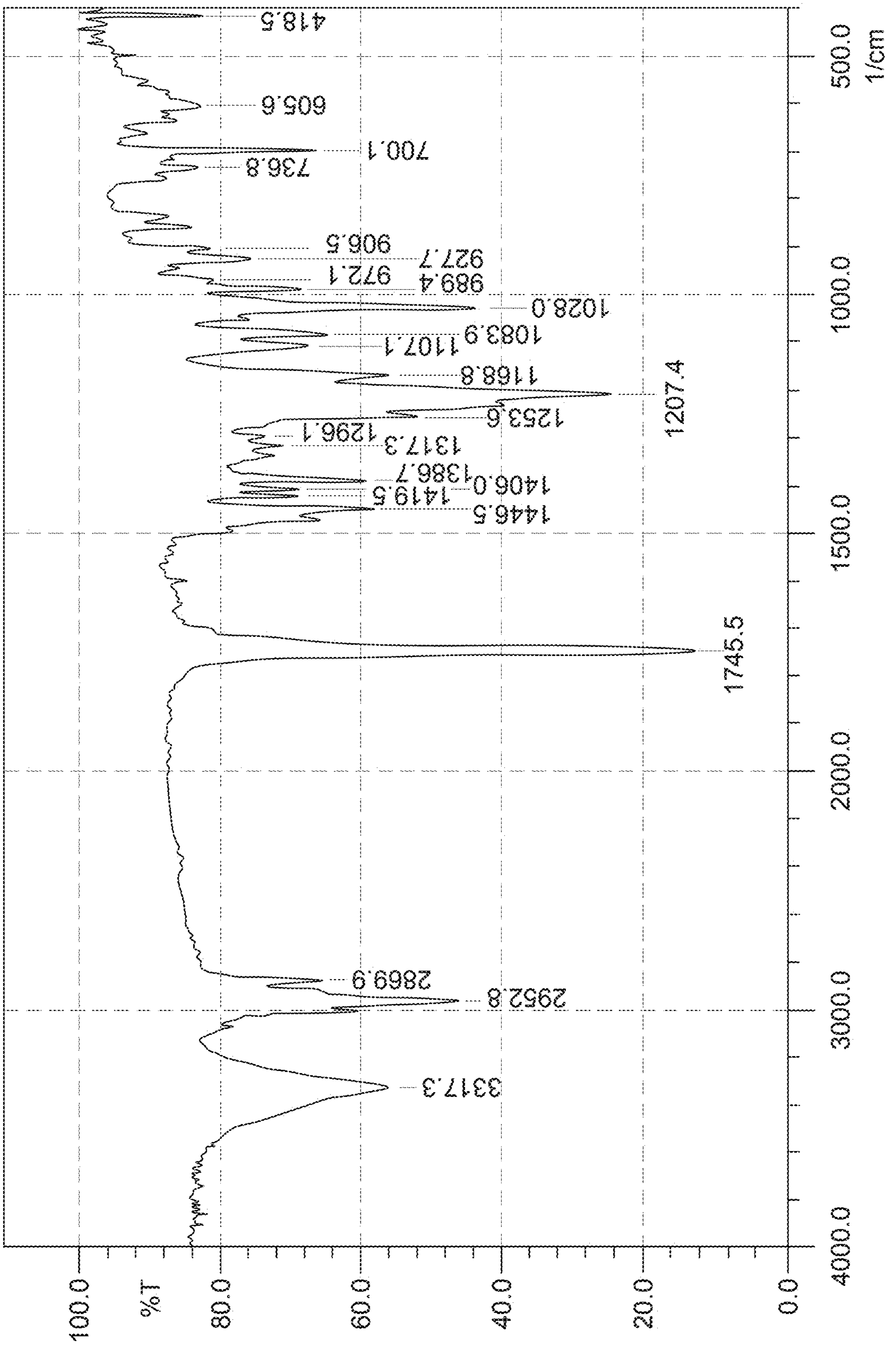
FIG. 20 Infrared absorption spectrum of the crystalline form (Form MJ) of sofpironium bromide prepared in Preparation Example 5.

FIG. 20 is the IR chart of the crystalline form of the compound (I-b) (Form MJ). The characteristic peaks are shown in Table 21.

TABLE 21

| Peak ($cm^{-1}$) |
|---|
| 3317 |
| 2953 |
| 1746 |
| 1447 |
| 1207 |
| 1028 |

Figure 21:
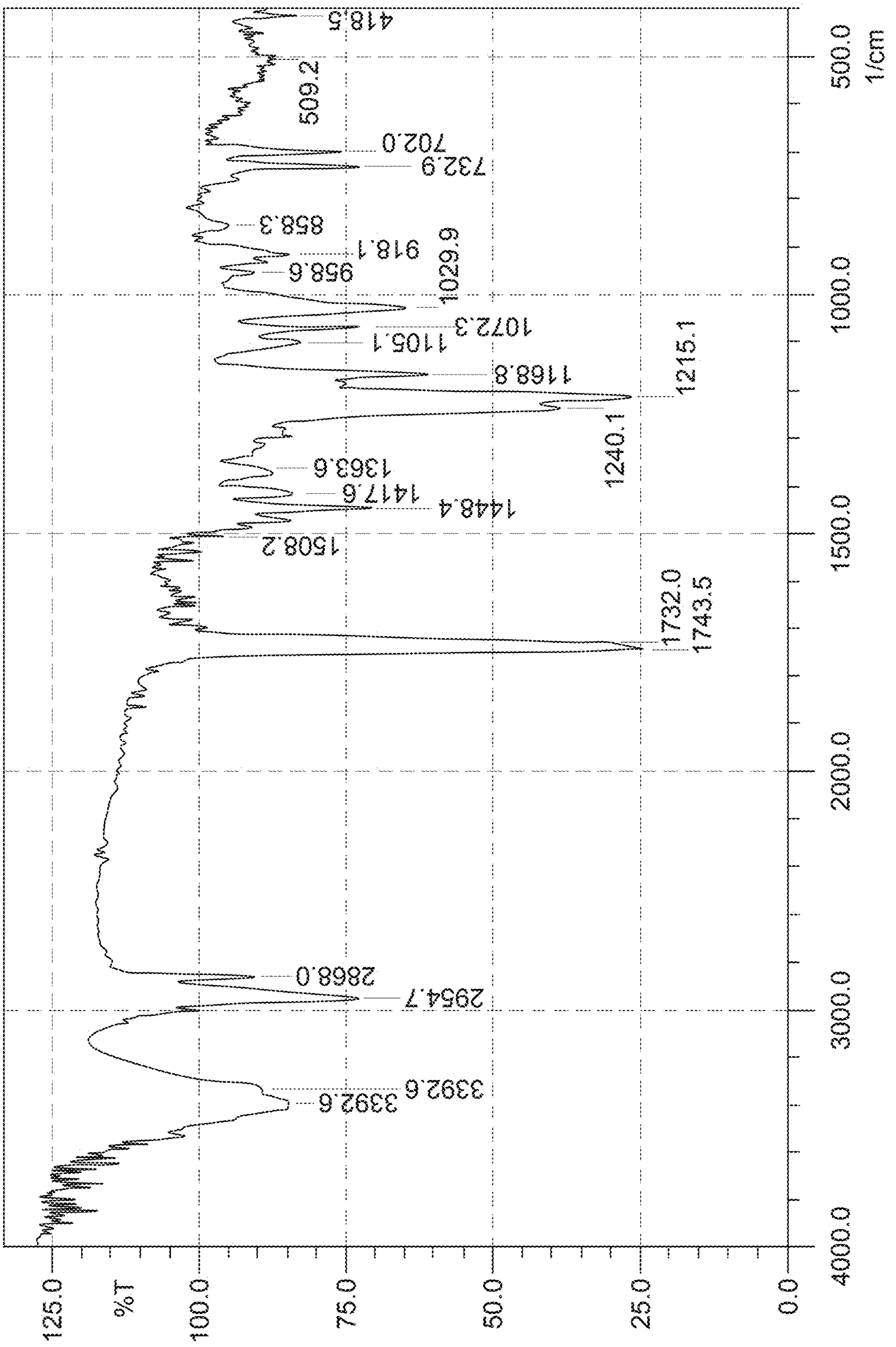
FIG. 21 Infrared absorption spectrum of the crystalline form (Form CO) of sofpironium bromide prepared in Example 6.

FIG. 21 is the IR chart of the crystalline form of the compound (I) (Form CO). The characteristic peaks are shown in Table 22.

TABLE 22

| Peak ($cm^{-1}$) |
|---|
| 3393 |
| 2955 |
| 1744 |
| 1448 |
| 1215 |
| 1030 |

The content ratios of the compound (I-a) and the compound (I-b) contained in Form A and Form B used in this test were within the range of 40:60 to 25:75.

Test Example 7 <Hygroscopic Property And Stability Test of Crystalline Forms (Dynamic Vapor Sorption: DVS)>

Each sample was dried under reduced pressure (in the presence of silica gel, 40° C., 1 hour), and weighed in an amount of about 20 mg on a sample pan, and the sorption-desorption isotherm (0 to 95% RH) was determined by using a dynamic vapor sorption analyzer under the following conditions.

<Conditions for Pre-Drying of Instruments>

TABLE 23

| Item | Conditions |
|---|---|
| Nitrogen pressure | 0.1 MPa |
| Temperature | 40° C. |
| Time | 3 hours |

<Conditions for Sorption-Desorption Isotherm Measurement>

TABLE 24

| Item | Conditions |
|---|---|
| Nitrogen pressure | 0.1 MPa |
| Solvent | Water |
| Temperature | 25° C. |
| Sorption isotherm | 0 to 95% R.H |
| Humidity level interval | 5% RH |

TABLE 25

| Crystalline form | Hygroscopicity (weight change)* | Crystal transition** |
|---|---|---|
| Form A | Not observed | Observed |
| From B | Not observed | Not observed |
| From MN | Not observed | Not observed |
| Form MJ | Not observed | Observed |
| Form CO | Not observed | Not observed |

*In this column of hygroscopicity, "Observed" means that the weight increased by more than 3% after the test, and "Not observed" means that the weight increased by 3% or less.
**In this column of crystal transition, "Observed" means that change of crystalline form was observed after the test, and "Not observed" means that the same crystalline form as observed before the test was maintained even after the test.

As shown by the results of Test Example 7, all the crystalline forms did not show hygroscopic property. However, crystal transition was observed when Form A and Form MJ were subjected to a cycle that humidity is increased from 0% RH to 95% RH, and returned to 0% RH. On the other hand, crystal transition was not observed for Form B, Form MN and Form CO even after they were subjected to the same conditions.

On the basis of these results, it was found that Form MN and Form CO do not cause crystal transition under humidified conditions, and are stable crystalline forms. It was also found that Form B is a crystalline form having a more suitable profile for a drug substance of medicaments as it contains Form MN and Form CO.

The content ratios of the compound (I-a) and the compound (I-b) contained in Form A and Form B used in this test were within the range of 40:60 to 25:75.

Test Example 8 <Humidity Stability Test of Form B>

Form B was stored at 25±2° C. and 93% RH for 4 weeks, and the appearance, purity, and a crystalline form thereof were observed from the start of the storage. The results are shown in the following table.

The purity test was carried out by the same method as that of Test Example 3. In this test, the term "impurities" is used to include the aforementioned compounds (III), (IV), and (V), as well as the other analogous substances, decomposition products, impurities, and contaminants. The crystalline form was determined by powder X-ray diffraction pattern.

TABLE 26

| Test item | At the time of start | After 1 week | After 2 weeks | After 4 weeks |
|---|---|---|---|---|
| Property (appearance) | White powder | White powder | White powder | White powder |
| Purity test (impurities) | N.D.* | N.D.* | N.D.* | N.D.* |
| Crystalline form | Form B | — | — | Form B |

*Lower than quantification limit (0.03%)

As can be seen from the results of Test Example 8, Form B gave no change in the appearance, purity, and crystalline form even after the storage at 25±2° C. and 93% RH for 4 weeks. Therefore, it was found that Form B is a stable crystalline form under the humidified conditions, and is a superior crystalline form for a drug substance of medicaments. Similarly, it also became clear that Form MN and Form CO constituting Form B are also superior crystalline forms for drug substance of medicaments.

The content ratio of the compound (I-a) and the compound (I-b) contained in Form B used in this test was within the range of 40:60 to 25:75.

Test Example 9 <Relative Comparison of Stabilities of Form A and Form B (60° C.)>

Stabilities of Form A and Form B was compared relatively. Each sample of Form A and Form B was stored at 60±2° C. for 4 weeks in a dark place. The results are shown in the following table. In the table, each value indicating the results of the purity test represents the ratio (%) of the impurities contained in the compound (I). Specifically, each value represents the ratio (%) of the total area of all the peaks other than the peaks of the compound (I-a) and compound (I-b) observed when the analysis was performed with the analysis conditions used in Test Example 3.

As shown in Test Example 7, Form A causes crystal transition under humidified conditions. The crystalline form after such crystal transition occurred is referred to as "Form A (after crystal transition)", and stability thereof was similarly measured.

In this test, the term "impurities" is used to include the aforementioned compounds (III), (IV), and (V), as well as the other analogous substances, decomposition products, impurities, and contaminants. The numerical values indicating isomer ratios are values obtained by dividing the peak area of the compound (I-a) with the sum of the peak areas of the compound (I-a) and the compound (I-b) for each case, which areas were obtained by analyzing with the analysis conditions of Test Example 3.

The content ratios of the compound (I-a) and the compound (I-b) contained in Form A and Form B used in this test were within the range of 40:60 to 25:75.

TABLE 27

| | | Measurement time | | | |
|---|---|---|---|---|---|
| Test item | Crystalline form | At the time of start | After 1 week | After 2 weeks | After 4 weeks |
| Purity test (impurities) | Form A | N.D.* | N.D.* | N.D.* | N.D.* |
| | Form B | N.D.* | N.D.* | N.D.* | N.D.* |
| | Form A (after crystal transition) | 0.03% | 0.03% | 0.03% | 0.03% |
| Isomer ratio | Form A | 0.34 | 0.34 | 0.35 | 0.35 |
| | Form B | 0.34 | 0.35 | 0.34 | 0.35 |

*Lower than quantification limit (0.03%)

As shown in the table mentioned above, both of Form A and Form B showed a purity higher than 99.9% at the time of the start and after 4 weeks passed, and thus the impurities did not increase even after 4 weeks passed. Further, during the test period, significant change of the isomer ratio of the compound (I-a) and the compound (I-b) was not observed.

On the other hand, for Form A (after crystal transition), 0.03% of impurity (compound (III)) was detected from the beginning, although it did not show increase of impurities.

On the basis of the results of Test Examples 7 to 9, it was revealed that, while both Form A and Form B are stable crystals, Form A causes crystal transition under humidified conditions, and invites contamination with some impurities. On the other hand, it was also revealed that Form B is stable so that it does not show such a phenomenon, and has a more suitable profile for a drug substance, of medicaments.

On the basis of the results mentioned above, it was revealed that the crystalline forms of sofpironium bromide of the present invention containing Form CO (for example, Form B) do not have a hygroscopic property, whilst have high purity, and are physicochemically stable crystalline forms, and therefore these crystalline forms have the best profile for a drug substance of medicaments.

INDUSTRIAL APPLICABILITY

The crystalline forms of the sofpironium bromide of the present invention are physicochemically stable, and have a profile suitable for a drug substance of medicaments.

Sofpironium bromide obtained by the preparation method of the present invention has high purity, and can be easily prepared in an industrial scale.

The invention claimed is:

1. A stable crystal Form MN of a compound shown as formula I-a (I-a)

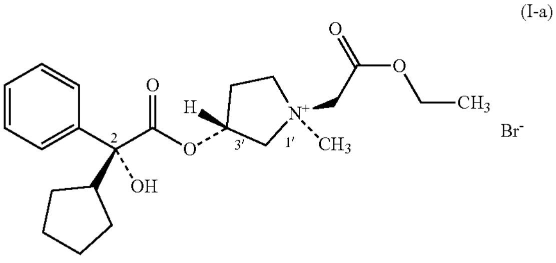

(2R, 3'R, 1'R)

characterized by showing peaks at 7.1±0.1, 21.4±0.1, 22.3±0.1, and 24.5±0.1 as diffraction angles 2θ in a powder X-ray diffraction spectrum.

2. The crystal Form MN of claim 1, wherein the crystal is not hygroscopic.

3. The crystal Form MN of claim 1, wherein the crystal form is a physicochemically stable crystalline form.

4. The crystal Form MN of claim 1, wherein the purity of the crystal form is not less than 98% w/w based on the content of the compound (I), wherein the compound (I) is represented by the formula (I)

(I)

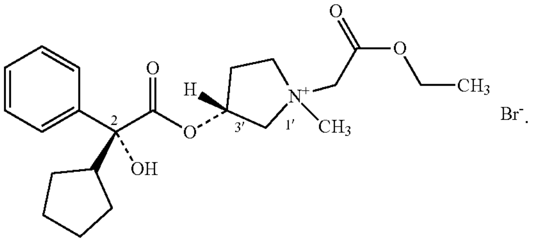

(2R, 3'R)

5. The crystal Form MN of claim 1, wherein a content of each compound represented by formulae III, IV and V (III)

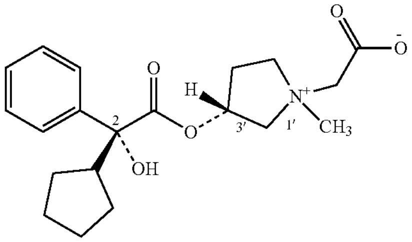

(2R, 3'R)

(IV)

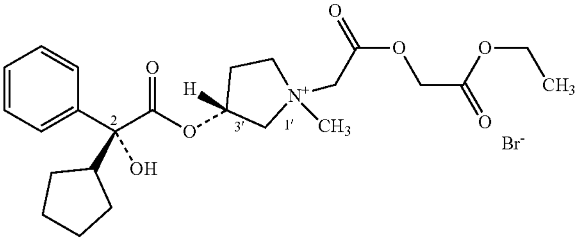

(2R, 3'R)

(V)

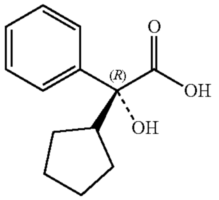

is not more than 0.5% w/w based on a content of compound (I), wherein the compound (I) is represented by the formula (I)

(I)

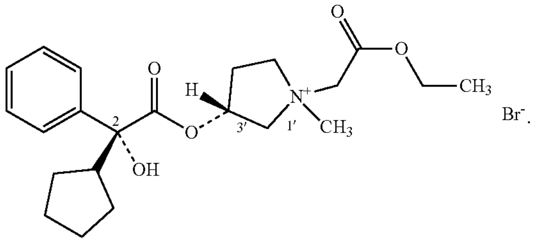

(2R, 3′R)

6. The crystal Form MN of claim 1, wherein the total content of impurities is not more than 2.0% w/w based on a content of compound (I), wherein the compound (I) is represented by the formula (I)

(I)

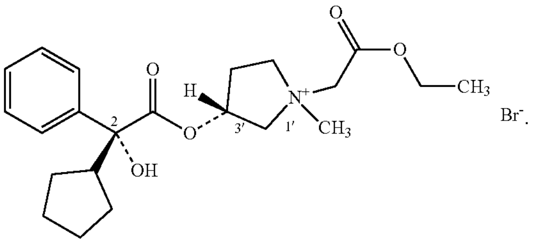

(2R, 3′R)

7. A stable topical pharmaceutical composition comprising:

a pharmaceutically effective amount of the crystal Form MN of claim 1 as an active pharmaceutical agent in a pharmaceutically acceptable carrier.

* * * * *